(12) United States Patent
Marcus et al.

(10) Patent No.: US 11,872,272 B2
(45) Date of Patent: *Jan. 16, 2024

(54) IL-15-BASED FUSIONS TO IL-12 AND IL-18

(71) Applicant: Altor Bioscience LLC, Culver City, CA (US)

(72) Inventors: Warren D. Marcus, Miramar, FL (US); Robert Newman, Miramar, FL (US); Bai Liu, Cooper City, FL (US); Lijing You, Miramar, FL (US); Lin Kong, Miramar, FL (US); Peter Rhode, Miami, FL (US); Hing C. Wong, Weston, FL (US)

(73) Assignee: Altor Bioscience, LLC, Culver City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/168,428

(22) Filed: Feb. 13, 2023

(65) Prior Publication Data

US 2023/0248813 A1 Aug. 10, 2023

Related U.S. Application Data

(63) Continuation of application No. 17/820,980, filed on Aug. 19, 2022, now Pat. No. 11,612,645, which is a continuation of application No. 17/486,683, filed on Sep. 27, 2021, now Pat. No. 11,571,470, which is a continuation of application No. 15/913,837, filed on Mar. 6, 2018, now Pat. No. 11,129,883.

(60) Provisional application No. 62/467,623, filed on Mar. 6, 2017.

(51) Int. Cl.
| | | |
|---|---|---|
| *A61K 39/00* | (2006.01) | |
| *C12N 15/62* | (2006.01) | |
| *C07K 14/54* | (2006.01) | |
| *A61K 47/68* | (2017.01) | |
| *C07K 16/28* | (2006.01) | |
| *A61P 35/00* | (2006.01) | |
| *C07K 14/715* | (2006.01) | |

(52) U.S. Cl.
CPC .... *A61K 39/00114* (2018.08); *A61K 47/6811* (2017.08); *A61P 35/00* (2018.01); *C07K 14/54* (2013.01); *C07K 14/5434* (2013.01); *C07K 14/5443* (2013.01); *C07K 14/715* (2013.01); *C07K 16/283* (2013.01); *C12N 15/62* (2013.01); *C07K 2319/30* (2013.01)

(58) Field of Classification Search
CPC .......... A61K 39/00114; A61K 38/20
See application file for complete search history.

(56) References Cited

U.S. PATENT DOCUMENTS

| | | | |
|---|---|---|---|
| 5,116,964 | A | 5/1992 | Capon et al. |
| 5,541,087 | A | 7/1996 | Lo et al. |
| 5,620,939 | A | 4/1997 | Haisa et al. |
| 5,891,680 | A | 4/1999 | Lieschke et al. |
| 8,163,879 | B2 | 4/2012 | Wong et al. |
| 8,492,118 | B2 | 7/2013 | Wong et al. |
| 8,507,222 | B2 | 8/2013 | Wong et al. |
| 8,940,289 | B2 | 1/2015 | Wong et al. |
| 9,255,141 | B2 | 2/2016 | Wong et al. |
| 9,328,159 | B2 | 5/2016 | Wong et al. |
| 9,428,573 | B2 | 8/2016 | Wong et al. |
| 9,464,127 | B2 | 10/2016 | Wong et al. |
| 9,925,247 | B2 | 3/2018 | Liu et al. |
| 10,150,805 | B2 | 12/2018 | Wong et al. |
| 10,450,359 | B2 | 10/2019 | Wong et al. |
| 11,129,883 | B2 | 9/2021 | Marcus et al. |
| 11,168,138 | B2 | 11/2021 | Li et al. |
| 11,571,470 | B2 | 2/2023 | Marcus et al. |
| 11,612,645 | B2 | 3/2023 | Marcus et al. |
| 2004/0219096 | A1 | 11/2004 | De Waal Malefyt et al. |
| 2005/0063945 | A1 | 3/2005 | Paul |
| 2008/0300188 | A1 | 12/2008 | Yang et al. |
| 2010/0303811 | A1 | 12/2010 | Ochi |
| 2012/0177595 | A1 | 7/2012 | Wong et al. |
| 2014/0242025 | A1 | 8/2014 | Wong et al. |
| 2015/0017121 | A1 | 1/2015 | Becher et al. |
| 2015/0374790 | A1 | 12/2015 | Lill et al. |
| 2019/0022187 | A1 | 1/2019 | Liu et al. |
| 2019/0023766 | A1 | 1/2019 | Wong et al. |
| 2019/0048055 | A1 | 2/2019 | Shrestha et al. |
| 2019/0330309 | A1 | 10/2019 | Soon-Shiong et al. |

FOREIGN PATENT DOCUMENTS

| | | |
|---|---|---|
| JP | 2006-514057 | 4/2006 |
| JP | 2011-045375 | 3/2011 |
| WO | WO 94/04689 | 3/1994 |
| WO | WO 94/29350 | 12/1994 |
| WO | WO 96/32478 | 10/1996 |
| WO | WO 97/34631 | 9/1997 |
| WO | WO 2005/046449 | 5/2005 |
| WO | WO 2012/040323 | 3/2012 |
| WO | WO 2013/053775 | 4/2013 |
| WO | WO 2018/165208 | 9/2018 |

OTHER PUBLICATIONS

Official Action for Canadian Patent Application No. 3055318, dated Sep. 20, 2023 4 pages.
Benton et al. (Apr. 8, 1977) "Screening λgt Recombinant Clones by Hybridization to Single Plaques in Situ", Science, 196(4286):180-182.
Berrien-Elliott et al., "Human Cytokine-Induced Memory-Like Natural Killer Cells," Journal of Innate Immunity, Apr. 30, 2015, vol. 7(6), pp. 563-571.

(Continued)

*Primary Examiner* — Prema M Mertz
(74) *Attorney, Agent, or Firm* — Sheridan Ross P.C.

(57) ABSTRACT

The invention features multi-specific fusion protein complexes with one domain comprising IL-15 or a functional variant and a binding domain specific to IL-12 or IL-18.

7 Claims, 21 Drawing Sheets
(17 of 21 Drawing Sheet(s) Filed in Color)
Specification includes a Sequence Listing.

(56) References Cited

OTHER PUBLICATIONS

Capon et al. (Feb. 9, 1989) "Designing CD4 Immunoadhesins for AIDS Therapy", Nature, 337(6207):525-531.
Cerwenka et al. (Feb. 2016, e-published on Jan. 25, 2016) "Natural Killer Cell Memory in Infection, Inflammation and Cancer", Nature Reviews Immunology, 16(2):112-123.
Chamow et al. (Feb. 1996) "Immunoadhesins: Principles and Applications", Trends Biotechnology, 14:52-60.
Chang et al. (Jan. 2013) "Donor Lymphocyte Infusions for Relapse After Allogeneic Transplantation. When, If and for Whom?", Blood Reviews, 27(1):55-62.
Chirifu et al. (Sep. 2007, e-published on Jul. 22, 2007) "Crystal Structure of the IL-15-IL-15Rα Complex, a Cytokine-Receptor Unit Presented in Trans", Nature Immunology, 8(9):1001-1007.
Database Genbank (Dec. 19, 1995) "Human Interleukin-15 Receptor Alpha Chain Precursor (IL15RA) mRNA, Complete cds", GenBank Accession No. U31628.1, 2 pages.
Database Genbank (May 20, 2005) "Mus Musculus Interleukin 15 Receptor, Alpha Chain, mRNA (cDNA clone Image:4457379), Complete cds", GenBank Accession No. BC095982.1, 2 pages.
Database Genbank (Sep. 14, 1995) "Mus Musculus Interleukin 15 (IL15) mRNA, Complete cds", GenBank Accession No. U14332.1, 2 pages.
Database Genbank (Sep. 21, 1994) "Human Interleukin 15 (IL15) mRNA, complete cds", GenBank Accession No. U14407.1, 2 pages.
Davis (1985) "Molecular Genetics of the T Cell-receptor Beta Chain", Annual Review of Immunology, 3:537-560.
Dubois et al., The Journal Immunology, 2016; vol. 197, pp. 168-178.
Ellison et al. (Jul. 10, 1982) "The Nucleotide Sequence of a Human immunoglobulin Cyl Gene", Nucleic Acids Research, 10(13):4071-4079.
Fehninger et al. (Dec. 2016) "Harnessing NK Cell Memory for Cancer immunotherapy", Trends in Immunology, 37(12):877-888.
Fleer (Oct. 1992) "Engineering Yeast for High Level Expression", Current Opinion in Biotechnology, 3(5):486-496.
Frankel et al. (Oct. 2000) "Cell Surface Receptor-Targeted Therapy of Acute Myeloid Leukemia: A Review", Cancer Biotherapy & Radiopharmaceuticals, 15(5):459-476.
Gerber et al. (May/Jun. 2009) "Antibody Drug-Conjugates Targeting the Tumor Vasculature—Current And Future Developments", mAbs, 1(3):247-253.
Gillies, Stephen D., et al. "Antibody-IL-12 fusion proteins are effective in SCID mouse models of prostate and colon carcinoma metastases." The Journal of Immunology 160.12 (1998): 6195-6203.
Graham et al. (Jul. 1977) "Characteristics of a Human Cell Line Transformed by DNA from Human Adenovirus Type 5", Journal of General Virology, 36(1):59-72.
Grunstein et al. (Oct. 1975) "Colony Hybridization: A Method for the Isolation of Cloned DNAs That Contain a Specific Gene", Proceedings of the National Academy of Sciences of the United States of America, 72(10):3961-3965.
Guillerey et al. (2016, e-published on Aug. 19, 2016) "Targeting Natural Killer Cells in Cancer immunotherapy", Nature immunology, 17:1025-1036.
Guo et al. (2013) "Therapeutic Cancer Vaccines: Past, Present and Future", Advances in Cancer Research, 119:421-475.
Han et al. (Dec. 2011, e-published on Oct. 22, 2011) "IL-15:IL-15 Receptor Alpha Superagonist Complex: High-Level Co-Expression in Recombinant Mammalian Cells, Purification and Characterization", Cytokine, 56(3):804-810.
Hu et al. (Feb. 2018, e-published on Sep. 7, 2017) "Chimeric Antigen Receptor (CAR)-Transduced Natural Killer Cells in Tumor immunotherapy", Acta Pharmacologica Sinica, 39:167-176.
Irving et al. (Apr. 3, 2017) "Engineering Chimeric Antigen Receptor T-Cells for Racing in Solid Tumors: Don't Forget the Fuel", Frontiers in immunology, 8(267):19 pages.
Kim et al. (Mar. 13, 2001) "Site-Specific Mutations in The Mature Form of Human IL-18 with Enhanced Biological Activity and Decreased Neutralization by IL-18 Binding Protein", PNAS, 98(6):3304-3309.
Kimmel (1987) "Identification and Characterization of Specific Clones: Strategy for Confirming the Validity of Presumptive Clones", Methods in Enzymology, 152:507-511.
Leong et al. (Feb. 4, 2003) "Optimized Expression and Specific Activity of IL-12 by Directed Molecular Evolution", PNAS, 100(3):1163-1168.
Leong, Jeffrey W., et al. "Preactivation with IL-12, IL-15, and IL-18 induces CD25 and a functional high-affinity IL-2 receptor on human cytokine-induced memory-like natural killer cells." Biology of Blood and Marrow Transplantation, 20.4 (2014): 463-473.
Liew et al. (Nov. 1, 2002) "Role of Interleukin 15 and Interleukin 18 in Inflammatory Response", Annals of the Rheumatic Diseases, 61(suppl 2):100-102.
Mikayama et al. Proc. Natl. Acad. Sci. USA (1993) vol. 90, pp. 10056-10060.
Moskaug et al. (Sep. 15, 1989) "Translocation of Diphtheria Toxin A-Fragment to the Cytosol. Role of The Site of Interfragment Cleavage", Journal of Biological Chemistry, 264(26):15709-15713.
Ni et al. (2012) "Sustained Effector Function of IL-12/15/18-Preactivated NK Cells against Established Tumors", Journal of Experimental Medicine, 209(13):2351-2365.
Ni et al., "Toward the next generation of NK cell-based adoptive cancer immunotherapy," OncoImmunology, Apr. 2013, vol. 2(4), pp. e23811-1-e23811-3.
Novellino et al. (e-published on Aug. 7, 2004) "A Listing of Human Tumor Antigens Recognized by T Cells: Mar. 2004 Update", Cancer Immunology, immunotherapy, 54(3):187-207.
Oleksiewicz et al. (e-published on Jun. 13, 2012) "Anti-bacterial Monoclonal Antibodies: Back to the Future?", Archives of Biochemistry and Biophysics, 526(2):124-131.
Olsnes et al. (1982) "Chimeric Toxins", Pharmacology and Therapeutics, 15(3):355-381.
Pardoll (Apr. 2012) "The Blockade of Immune Checkpoints in Cancer immunotherapy", Nature Reviews Cancer, 12(4):252-264.
Parmiani et al. (2007) "Unique Human Tumor Antigens: immunobiology and Use in Clinical Trials", The Journal of Immunology, 178(4):1975-1979.
Pastan et al. (1992) "Recombinant Toxins as Novel Therapeutic Agents", Annual Review Biochemistry, 61:331-354.
Pastan et al. (Dec. 5, 1986) "immunotoxins", Cell, 47:641-648.
Rager et al. (Sep. 5, 2011) "Cellular Therapy Following Allogeneic Stem-Cell Transplantation", Therapeutic Advances in Hematology, 2(6):409-428.
Roddie et al. (Jan. 27, 2011) "Donor Lymphocyte Infusion Following Allogeneic Hematopoietic Stem Cell Transplantation", Expert Opinion on Biological Therapy, 11(4):473-487.
Romee et al. (Sep. 21, 2016) "Cytokine-Induced Memory-like Natural Killer Cells Exhibit Enhanced Responses against Myeloid Leukemia", Science Translational Medicine,8(357):13 pages.
Rueff et al. (Jun. 2014) "Lymphocyte Subset Recovery and Outcome after Autologous Hematopoietic Stem Cell Transplantation for Plasma Cell Myeloma", Biology of Blood and Marrow Transplantation, 20(6):896-899.
Sliwkowski et al. (Sep. 13, 2013) "Antibody Therapeutics in Cancer", Science, 341(6151):1192-1198.
Thaventhiran et al. (Oct. 17, 2012) "T Cell Co-inhibitory Receptors: Functions and Signalling Mechanisms", Journal of Clinical & Cellular immunology, 12 pages.
Tomalia (1993) "Starburst/Cascade Dendrimers: Fundamental Building Blocks for a New Nanoscopic Chemistry Set", Aldrichimica Acta, 26(4):91-101.
Urlaub et al. (Jul. 1980) "Isolation of Chinese Hamster Cell Mutants Deficient in Dihydrofolate Reductase Activity", PNAS, 77(7):4216-4220.
Voet et al. Biochemistry John Wiley & Sons, Inc., (1990), pp. 126-128 and 228-234.
Wahl et al. (1987) "Molecular Hybridization of Immobilized Nucleic Acids: Theoretical Concepts and Practical Considerations", Methods in Enzymology, 152:399-407.

(56) References Cited

OTHER PUBLICATIONS

Waldmann (Aug. 2006) "The Biology of Interleukin-2 and Interleukin-15: Implications for Cancer Therapy and Vaccine Design", Nature Reviews Immunology, 6(8):595-601.
Wang et al. (2015, e-published on Sep. 8, 2014) "T Cell-Based Targeted immunotherapies for Patients with Multiple Myeloma", International Journal of Cancer, 136:1751-1768.
Weidle et al. (Jul.-Aug. 2013) "The Emerging Role of New Protein Scaffold-based Agents for Treatment of Cancer", Cancer Genomics and Proteomics, 10(4):155-168.
Whitlow et al. (Apr. 1991) "Single-Chain Fv Proteins and their Fusion Proteins", Methods: A Companion to Methods in Enzymology, 2(2):97-105.
Wong et al. (Nov. 2013) "The IL-15-based Superagonist ALT-803 Promotes the Antigen-Independent Conversion of Memory CD8+ T Cells into innate-like Effector Cells with Antitumor Activity", OncoImmunology, 2(11): e26442—3 pages.
Wu et al. (Aug. 2010) "IL-15R Alpha-IgG1-Fc Enhances IL-2 and IL-15 Anti-Tumor Action Through NK and CD8+ T Cells Proliferation and Activation", Journal of Molecular Cell Biology, 2(4):217-222.
Xu, Wenxin, et al. "Efficacy and mechanism-of-action of a novel superagonist interleukin-15: interleukin-15 receptor? Su/Fc fusion complex in syngeneic murine models of multiple myeloma." Cancer research 73.10 (2013): 3075-3086.
Yoon et al. (2000) "Charged Residues Dominate a Unique Interlocking Topography in the Heterodimeric Cytokine Interleukin-12", The EMBO Journal, 19(14):3530-3541.
Zhu et al. (Sep. 15, 2009) "Novel Human Interleukin-15 Agonists", Journal of Immunology, 183(6):3598-3607.
International Search Report issued in counterpart International Application No. PCT/US2018/021220, dated Jun. 18, 2019, 5 pages.
Written Opinion issued in counterpart International Application No. PCT/US2018/021220, dated Sep. 10, 2019, 9 pages.
International Preliminary Report on Patentability received for PCT International Application No. PCT/US2018/021220, dated Sep. 19, 2019, 11 pages.
Official Action for Canadian Patent Application No. 3055318, dated Oct. 6, 2021 5 pages.
Official Action for Canadian Patent Application No. 3055318, dated Aug. 26, 2022 4 pages.
Extended European Search Report for European Patent Application No. 18764359.8, dated Dec. 14, 2020, 7 pages.
Supplemental Search Report for European Patent Application No. 18764359.8, dated Jan. 19, 2021, 5 pages.
Official Action for Japanese Patent Application No. 2019-548419, dated Jan. 4, 2022 7 pages.
Official Action (with English machine translation) for Japanese Patent Application No. 2019-548419, dated Jul. 7, 2022 6 pages.
Official Action for U.S. Appl. No. 15/913,837, dated Aug. 5, 2019 12 pages, Restriction Requirement.
Official Action for U.S. Appl. No. 15/913,837, dated Dec. 6, 2019 16 pages.
Final Action for U.S. Appl. No. 15/913,837, dated May 5, 2020 20 pages.
Official Action for U.S. Appl. No. 15/913,837, dated Jun. 19, 2020 23 pages.
Final Action for U.S. Appl. No. 15/913,837, dated Dec. 23, 2020 12 pages.
Notice of Allowance for U.S. Appl. No. 15/913,837, dated May 18, 2021 8 pages.
Official Action for U.S. Appl. No. 17/486,683, dated Sep. 23, 2022 13 pages, Restriction Requirement.
Notice of Allowance for U.S. Appl. No. 17/486,683, dated Nov. 7, 2022 9 pages.
Official Action for U.S. Appl. No. 17/820,980, dated Oct. 11, 2022 10 pages, Restriction Requirement.
Official Action for U.S. Appl. No. 17/820,980, dated Nov. 16, 2022 8 pages, 2nd Restriction Requirement.
Notice of Allowance for U.S. Appl. No. 17/820,980, dated Jan. 23, 2023 10 pages.
Official Action (with English machine translation) for Chinese Patent Application No. 201880016721.8, dated Feb. 3, 2023 18 pages.
Official Action (with English machine translation) for Chinese Patent Application No. 201880016721.8, dated Jul. 13, 2023 8 pages.
Official Action (with English machine translation) for Korean Patent Application No. 10-2019-7029313, dated May 19, 2023 7 pages.

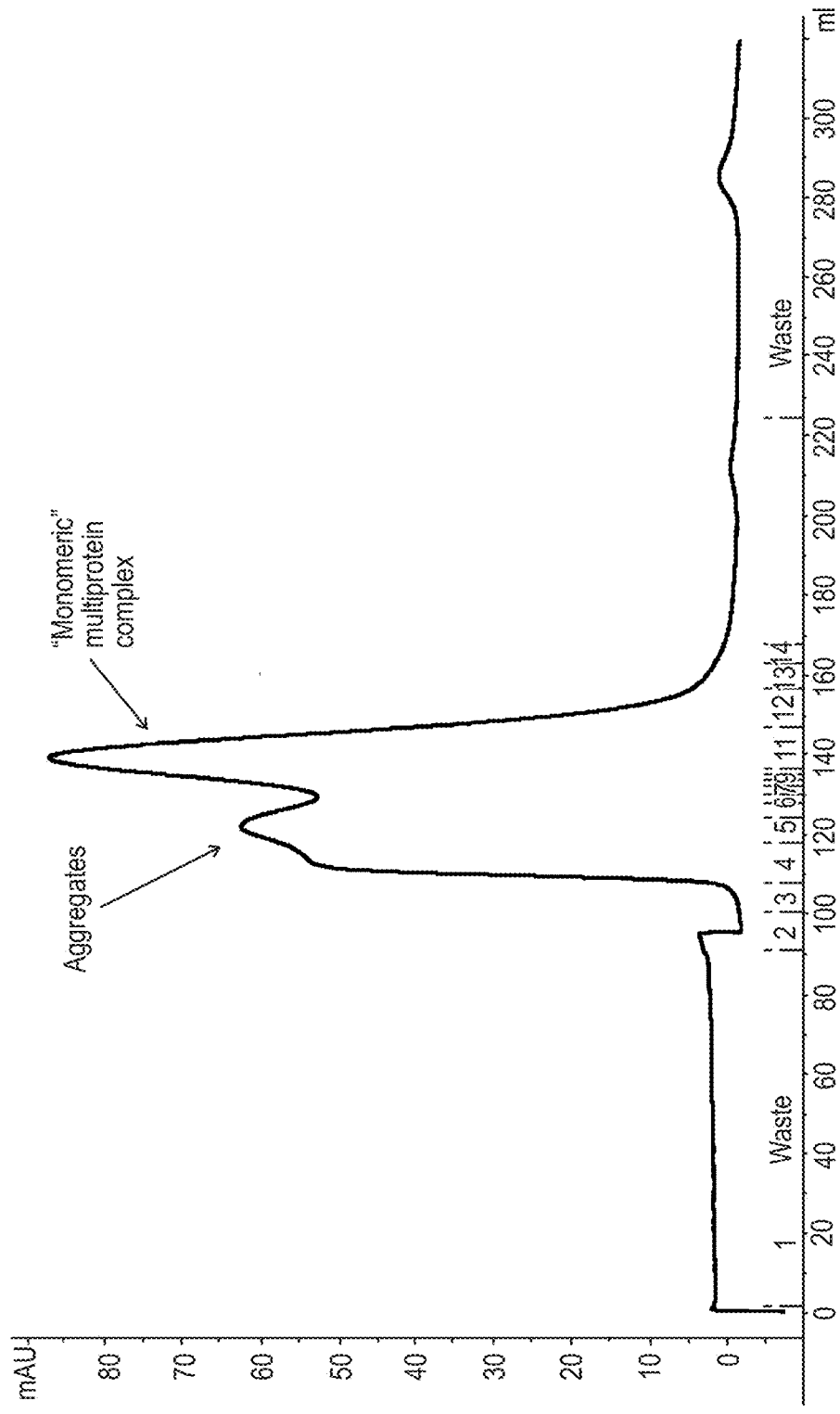

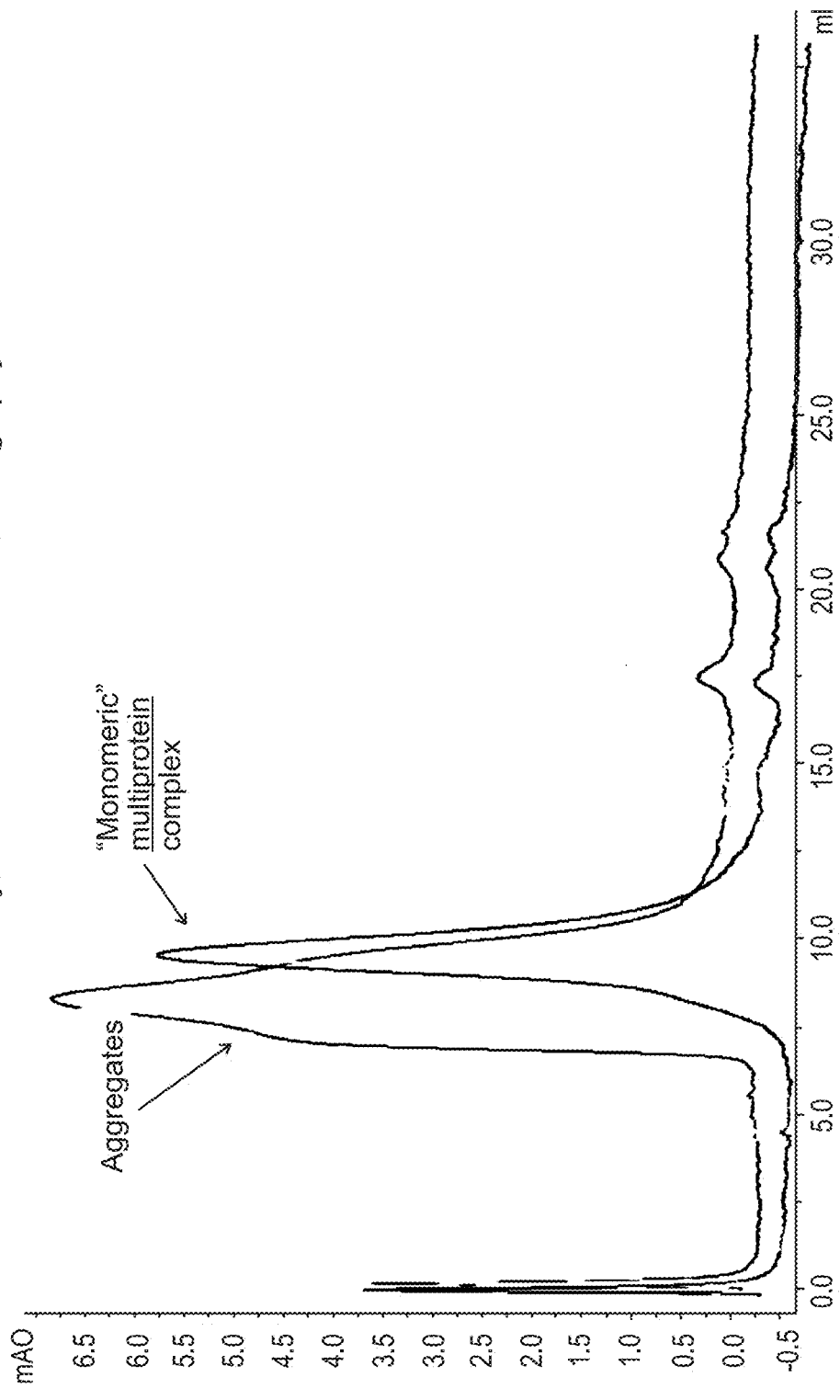

IL-15-BASED FUSIONS TO IL-12 AND IL-18

CROSS-REFERENCE TO RELATED APPLICATIONS

This application is a continuation of U.S. patent application Ser. No. 17/820,980, filed Aug. 19, 2022, now U.S. Pat. No. 11,612,645, which is a continuation of U.S. patent application Ser. No. 17/486,683, filed Sep. 27, 2021, now U.S. Pat. No. 11,571,470, which is continuation of U.S. patent application Ser. No. 15/913,837, filed Mar. 6, 2018, now U.S. Pat. No. 11,129,883, which claims the benefit of U.S. provisional application 62/467,623, filed Mar. 6, 2017, each of which is incorporated by reference in their entireties.

REFERENCE TO SEQUENCE LISTING

The instant application contains a Sequence Listing which has been submitted electronically in XML format and is hereby incorporated by reference in its entirety. Said XML file, created on Aug. 19, 2022, is named 8774ALT-14-1-1_Seq_listing.xml and is 21,000 bytes in size.

FIELD OF THE INVENTION

This invention relates generally to the field of multimeric fusion molecules.

BACKGROUND OF THE INVENTION

Prior to the invention described herein, there was a pressing need to develop new strategies to augment immune responses and provide therapeutic benefit to patients with neoplasia or infectious diseases.

SUMMARY OF THE INVENTION

The invention is based, at least in part, on the surprising discovery that multi-specific interleukin-15 (IL-15)-based fusion protein complexes enhance the stimulation of immune cells and promote their activity against disease cells, thereby resulting in reduction or prevention of disease. These IL-15-based fusion protein complexes may also show increased binding to disease and target antigens. Provided herein are multi-specific IL-15-based fusion protein complexes comprising IL-12 and IL-18 binding domains (FIGS. 1A, 1B). Specifically, described herein are fusion protein complexes comprising an IL-15N72D:IL-15RαSu-Ig Fc scaffold fused to IL-12 and/or IL-18 binding domains. As described in detail below, when characterized using human immune cells, these fusion protein complexes exhibit binding and biological activity of each of the IL-15, IL-12 and IL-18 cytokines. Additionally, these fusion protein complexes induce cytokine-induced memory-like (CIML) natural killer (NK) cells with elevated activation markers, increased cytotoxicity against tumor cells and enhanced production of IFN-γ.

As such, the fusion protein complex as a single molecule binds to and signals via multiple cytokine receptors on NK cells to provide the responses previously observed only with a combination of multiple individual cytokines. Additionally, these fusion protein complexes comprise the Fc region of Ig molecules, which can form a dimer to provide a soluble multi-polypeptide complex, bind Protein A for the purpose of purification and interact with Fcγ receptors on NK cells and macrophages, thereby providing advantages to the fusion protein complex that are not present in the combination of individual cytokines. Mammalian cell expression-based methods for making these fusion protein complexes suitable for large scale production of clinical grade material are described herein. Additional methods for making and using CIML NK cells induced by the fusion protein complex of the invention are also provided.

Accordingly, provided is an isolated soluble fusion protein complex comprising at least two soluble proteins. For example, the first protein comprises an WL-15 polypeptide, e.g., a variant IL-15 polypeptide comprising an N72D mutation (IL-15N72D). The second protein comprises a soluble IL-15 receptor alpha sushi-binding domain (IL-15RαSu) fused to an immunoglobulin Fc domain (IL-15RαSu/Fc). A third component of the isolated soluble fusion protein complex comprises a binding domain of IL-12, wherein the IL-12 binding domain is fused to the either the IL-15N72D or the IL-15RαSu/Fc protein. A forth component of the isolated soluble fusion protein complex comprises a binding domain of IL-18, wherein the IL-18 binding domain is fused to the either the IL-15N72D or the IL-15RαSu/Fc protein. In some cases, the IL-12 and/or IL-18 binding domains are fused to both the IL-15N72D and IL-15RαSu/Fc proteins. In other cases, either the IL-12 or IL-18 binding domain is fused to the IL-15N72D or the IL-15RαSu/Fc proteins and another binding domain is fused to the other protein. In other cases, the complex comprises an IL-18 binding domain fused to the IL-15N72D:IL-15RαSu-Ig Fc scaffold without IL-12 or an IL-18 binding domain fused to the IL-15N72D:IL-15RαSu-Ig Fc scaffold without IL-12. The fusions may be made at the N- or C-terminus of the proteins. The IL-12 protein may comprise a heterodimer of the p40 and p35 IL-12 subunits. Alternatively, the IL-12 protein may comprise a single-chain format in which the p40 and p35 subunits are linked by a flexible polypeptide linker. The single-chain IL-12 may comprise either the C-terminus of p40 linked to the N-terminus of p35 or the C-terminus of p35 linked to the N-terminus of p40. An exemplary fusion protein complex comprises an IL-18 polypeptide covalently linked to an IL-15N72D and a single-chain IL-12 polypeptide covalently linked to an IL-15RαSu/Fc fusion protein. Alternatively, the fusion protein complex comprises a single-chain IL-12 polypeptide covalently linked to an IL-15N72D and an IL-18 polypeptide covalently linked to an IL-15RαSu/Fc fusion protein (FIGS. 1A, 1B).

Exemplary first proteins comprise the amino acid sequences set forth in SEQ ID NO: 2 and SEQ ID NO: 6. Exemplary second proteins comprise the amino acid sequences set forth in SEQ ID NO: 4 and SEQ ID NO: 8. Exemplary nucleic acid sequences encoding the first protein comprise the sequences set forth in SEQ ID NO: 1 and SEQ ID NO: 5. Exemplary nucleic acid sequences encoding the second protein comprise the sequences set forth in SEQ ID NO: 3 and SEQ ID NO: 7. In one aspect, the nucleic acid sequence(s) further comprises a promoter, translation initiation signal, and leader sequence operably linked to the sequence encoding the fusion protein. Also provided are DNA vectors comprising the nucleic acid sequences described herein. For example, the nucleic acid sequence is in a vector for replication, expression, or both.

Also provided is a soluble fusion protein complex comprising a first soluble fusion protein complex covalently linked to a second soluble fusion protein complex. For example, the soluble fusion protein complexes of the invention are multimerized, e.g., dimerized, trimerized, or otherwise multimerized (e.g., 4 complexes, 5 complexes, etc.). For example, the multimers are homomultimers or heteromultimers. The soluble fusion protein complexes are joined by covalent bonds, e.g., disulfide bonds, chemical cross-linking agents. In some cases, one soluble fusion protein is covalently linked to another soluble fusion protein by a disulfide bond linking the Fc domain of the first soluble protein to the Fc domain of the second soluble protein.

The Fc domain or functional fragment thereof includes an Fc domain selected from the group consisting of IgG Fc domain, human IgG1 Fc domain, human IgG2 Fc domain, human IgG3 Fc domain, human IgG4 Fc domain, IgA Fc domain, IgD Fc domain, IgE Fc domain, and IgM Fc domain; mouse IgG2A domain, or any combination thereof. Optionally, the Fc domain includes an amino acid change that results in an Fc domain with altered complement or Fc receptor binding properties or altered dimerization or glycosylation profiles. Amino acid changes to produce an Fc domain with altered complement or Fc receptor binding properties or altered dimerization or glycosylation profiles are known in the art. For example, a substitution of leucine residues at positions 234 and 235 of the IgG1 CH2 (numbering based on antibody consensus sequence) (i.e., . . . P E L L G G . . . ) with alanine residues (i.e., . . . P E A A G G . . . ) results in a loss of Fc gamma receptor binding, whereas the substitution of the lysine residue at position 322 of the IgG1 CH2 (numbering based on antibody consensus sequence) (i.e., . . . K C K S L . . . ) with an alanine residue (i.e., . . . K C A S L . . . ) results in a loss of complement activation. In some examples, such mutations are combined.

In some aspects, the IL-12 or IL-18 binding domains is covalently linked to an IL-15 polypeptide (or functional fragment thereof) by a polypeptide linker sequence. Similarly, the IL-12 or IL-18 binding domain is covalently linked to an IL-15Rα polypeptide (or functional fragment thereof) by a polypeptide linker sequence. Optionally, the IL-15Rα polypeptide (or functional fragment thereof) is covalently linked to the Fc domain (or functional fragment thereof) by a polypeptide linker sequence. Each polypeptide linker sequence can be selected independently. Optionally, the polypeptide linker sequences are the same. Alternatively, they are different.

Optionally, the soluble fusion protein complexes of the invention are provided wherein at least one of the soluble fusion proteins comprise one or more binding domain or detectable labels. Such binding domains may comprise antibodies, soluble T cell receptors, ligands, soluble receptor domains or functional fragments thereof. IL-15-based fusion protein complexes comprising such binding domains have been previously described in U.S. Pat. No. 8,492,118, incorporated herein by reference. Detectable labels include, but are not limited to, biotin, streptavidin, an enzyme or catalytically active fragment thereof, a radionuclide, a nanoparticle, a paramagnetic metal ion, or a fluorescent, phosphorescent, or chemiluminescent molecule, or any combination thereof.

The invention provides methods for making the soluble fusion protein complexes of the invention. The method includes the steps of: a) introducing into a first host cell a DNA vector with appropriate control sequences encoding the first protein, b) culturing the first host cell in media under conditions sufficient to express the first protein in the cell or the media, c) purifying the first protein from the host cells or media, d) introducing into a second host cell a DNA vector with appropriate control sequences encoding the second protein, e) culturing the second host cell in media under conditions sufficient to express the second protein in the cell or the media, f) purifying the second protein from the host cells or media, and g) mixing the first and second proteins under conditions sufficient to allow binding between IL-15 domain of a first protein and the soluble IL-15Rα domain of a second protein to form the soluble fusion protein complex.

In some cases, the method further includes mixing the first and second protein under conditions sufficient to allow formation of a disulfide bond between the polypeptides expressed from the expression vectors.

Alternatively, methods for making soluble fusion protein complexes of the invention are carried out by a) introducing into a host cell a DNA vector with appropriate control sequences encoding the first protein and a DNA vector with appropriate control sequences encoding the second protein, b) culturing the host cell in media under conditions sufficient to express the proteins in the cell or the media and allow association between IL-15 domain of a first protein and the soluble IL-15Rα domain of a second protein to form the soluble fusion protein complex, and c) purifying the soluble fusion protein complex from the host cells or media.

In one aspect, the method further includes mixing the first and second protein under conditions sufficient to allow formation of a disulfide bond between the polypeptides expressed from the expression vectors.

Also provided are methods for making soluble fusion protein complexes comprising a) introducing into a host cell a DNA vector with appropriate control sequences encoding the first and second proteins, b) culturing the host cell in media under conditions sufficient to express the proteins in the cell or the media and allow association between IL-15 domain of a first protein and the soluble IL-15Rα domain of a second protein to form the soluble fusion protein complex, and to allow formation of a disulfide bond between the polypeptides, and c) purifying the soluble fusion protein complex from the host cells or media.

Optionally, the method further includes mixing the first and second protein under conditions sufficient to allow formation of a disulfide bond between the polypeptides expressed from the expression vectors.

In some cases, the method further includes purification of the fusion protein complex by Protein A affinity chromatography, size exclusion chromatography, ion exchange chromatography and/or other standard methods (including viral inactivation and/or filtration) sufficient to generate a sufficiently pure fusion protein complex suitable for use as a clinical reagent or therapeutic.

In certain aspects of the soluble fusion protein complexes of the invention, the IL-15 polypeptide is an IL-15 variant having a different amino acid sequence than native IL-15 polypeptide. The human IL-15 polypeptide is referred to herein as huIL-15, hIL-15, huILL5, hIL15, IL-15 wild type (wt), and variants thereof are referred to using the native amino acid, its position in the mature sequence and the variant amino acid. For example, huIL15N72D refers to human IL-15 comprising a substitution of N to D at position 72. In one aspect, the IL-15 variant functions as an IL-15 agonist as demonstrated, e.g., by increased binding activity for the IL-15RβγC receptors compared to the native IL-15 polypeptide. Alternatively, the IL-15 variant functions as an IL-15 antagonist as demonstrated by e.g., decreased binding activity for the IL-15RαγC receptors compared to the native IL-15 polypeptide.

Methods of enhancing immune function are carried out by a) contacting a plurality of cells with a soluble fusion protein complex of the invention, wherein the plurality of cells further include immune cells comprising the IL-15R chains recognized by the IL-15 domain, the IL-12R chains recognized by the IL-12 domain and/or the IL-18R chains recognized by the IL-18 domain, and b) activating the immune cells via signaling of the IL-15R, IL-12R and/or IL-18R. In one aspect, the method of enhancing immune function further includes activation the immune cells via signaling of a combination of at least two or all of the IL-15R, IL-12R and IL-18R by the soluble fusion protein complex. Exemplary methods for enhancing immune function include activation of NK cells via signaling of the IL-15R, IL-12R and IL-18R by the soluble fusion protein complex. Such methods include activation of NK cells resulting in increased activation markers (i.e., CD25, CD69), elevated cytotoxicity against diseased cells or increased production of IFN-γ. In some aspects, methods include induction of CIML NK cells by the soluble fusion protein complex of the invention.

Methods for killing a target cell are carried out by a) contacting a plurality of cells with a soluble fusion protein complex of the invention, wherein the plurality of cells further include immune cells comprising the IL-15R chains recognized by the IL-15 domain, the IL-12R chains recognized by the IL-12 domain and/or the IL-18R chains recognized by the IL-18 domain, and the target disease cells, b) activating the immune cells via signaling of the IL-15R, IL-12R and/or IL-18R, and c) killing the target disease cells by the activated immune cells. In one aspect, the method includes activation the immune cells via signaling of a combination of at least two or all of the IL-15R, IL-12R and IL-18R by the soluble fusion protein complex. Exemplary methods include activation of NK cells, in particular CIML NK cells, via signaling of the IL-15R, IL-12R and IL-18R by the soluble fusion protein complex. Such methods include activation of NK cells resulting in activation markers (i.e., CD25, CD69), elevated cytotoxicity against target cells.

The invention also provides methods for preventing or treating disease in a patient, the method including the steps of: a) mixing immune cells comprising the IL-15R chains recognized by the IL-15 domain, the IL-12R chains recognized by the IL-12 domain and/or the IL-18R chains recognized by the IL-18 domain with a soluble fusion protein complex of the invention, b) activating the immune cells via signaling of the IL-15R, IL-12R and/or IL-18R, c) administering (or adoptively transfer) to the patient the activated immune cells, and d) damaging or killing the disease cells via the activated immune cells sufficient to prevent or treat the disease in the patient. In one aspect, the method includes activation the immune cells via signaling of a combination of at least two or all of the IL-15R, IL-12R and IL-18R by the soluble fusion protein complex. Exemplary methods include activation of NK cells, in particular, CIML NK cells, via signaling of the IL-15R, IL-12R and IL-18R by the soluble fusion protein complex. Other aspects of the method include use of immortalized immune cells, such as NK-92, aNK, haNK or taNK cells, which may be irradiated prior to transfer. In some embodiments of the invention, the patient is pretreated or preconditioned to facilitate engraftment or survival of the adoptively transferred cells. Examples of preconditioning include treatment with cyclophosphamide and fludarabine. Additionally, the patient may be treated with agents that promote activation, survival, or persistence of the adoptively transferred cells pre- and/or post-cell transfer. Examples of such treatment include use of IL-2, IL-15, ALT-803 or other immunostimulatory agents. Other therapeutic approaches of known in the field of adoptive cell therapy (i.e., including but not limited to allogeneic, autologous, haploidentical, DLI, stem cell, CAR T, NK92-based and CAR NK therapies) may also be used in the methods herein.

Also provided are methods for preventing or treating disease in a patient, the method including the steps of: a) administering to the patient a soluble fusion protein complex of the invention, b) activating the immune cells in the patient via signaling of the IL-15R, IL-12R and/or IL-18R, and c) damaging or killing the disease cells via the activated immune cells sufficient to prevent or treat the disease in the patient.

Administration of the fusion protein complexes of the invention induces an immune response in a subject. For example, administration of the fusion protein complexes of the invention induces an immune response against cells associated with neoplasia or infectious disease. In one aspect, the fusion protein complex of the invention increases immune cell proliferation, activation markers, cytotoxicity against target cells, and/or production of pro inflammatory cytokines.

The invention provides methods of stimulating immune responses in a mammal by administering to the mammal an effective amount of the soluble fusion protein complex of the invention. The invention also provides methods of suppressing immune responses in a mammal by administering to the mammal an effective amount of the soluble fusion protein complex of any one of the invention.

Methods for treating a neoplasia or infectious disease in a subject in need thereof are carried out by administering to a subject an effective amount of activated immune cells or a pharmaceutical composition comprising a soluble fusion protein complex described herein. For example, methods for treating solid or hematological malignancies in a subject in need thereof are carried out by administering to a subject an effective amount of CIML NK cells activated ex vivo by the soluble fusion protein complex of the invention, thereby treating the malignancy. Exemplary soluble fusion protein complexes comprise the amino acid sequences set forth in SEQ ID NO: 2 and SEQ ID NO: 6 and in SEQ ID NO: 4 and SEQ ID NO: 8.

Suitable neoplasias for treatment with the methods described herein include a glioblastoma, prostate cancer, acute myeloid leukemia, B-cell neoplasm, multiple myeloma, B-cell lymphoma, B cell non-Hodgkin's lymphoma, Hodgkin's lymphoma, chronic lymphocytic leukemia, acute myeloid leukemia, cutaneous T-cell lymphoma, T-cell lymphoma, a solid tumor, urothelial/bladder carcinoma, melanoma, lung cancer, renal cell carcinoma, breast cancer, gastric and esophageal cancer, head and neck cancer, prostate cancer, pancreatic cancer, colorectal cancer, ovarian cancer, non-small cell lung cancer, and squamous cell head and neck carcinoma.

An exemplary infection for treatment using the methods described herein include infections with human immunodeficiency virus (HIV) or cytomegalovirus (CMV). The methods described herein are also useful to treat bacterial infections (e.g., gram positive or gram negative bacteria) (See, e.g., Oleksiewicz et al. 2012. Arch Biochem Biophys. 526: 124-31, incorporated herein by reference).

Cell therapies of the invention comprise administration of an effective amount of activated immune cells. For example, an effective amount of activated NK cells is between $1\times10^4$ cells/kg and $1\times10^{10}$ cells/kg, e.g., $1\times10^4$, $1\times10^5$, $1\times10^6$, $1\times10^7$, $1\times10^8$, $1\times10^9$, and $1\times10^{10}$ cells/kg, or such amounts that can be isolated by leukapheresis. Alternatively, activated immune cells are administered as a fixed dose or based on body surface area (i.e., per $m^2$). Cells can be administered after ex vivo activation or cryogenically preserved and administered after thawing (and washing as needed).

The pharmaceutical composition comprising a fusion protein complex is administered in an effective amount. For example, an effective amount of the pharmaceutical composition is between about 1 µg/kg and 100 µg/kg, e.g., 1, 5, 10, 15, 20, 25, 30, 35, 40, 45, 50, 55, 60, 65, 70, 75, 80, 85, 90, 95, or 100 µg/kg. Alternatively, the fusion protein complex is administered as a fixed dose or based on body surface area (i.e., per m$^2$).

The adoptively transferred immune cells or pharmaceutical composition comprising the fusion protein complex is administered at least one time per month, e.g., twice per month, once per week, twice per week, once per day, twice per day, every 8 hours, every 4 hours, every 2 hours, or every hour. Suitable modes of administration for the adoptively transferred immune cells include systemic administration, intravenous administration, or local administration. Suitable modes of administration for the pharmaceutical composition include systemic administration, intravenous administration, local administration, subcutaneous administration, intramuscular administration, intratumoral administration, inhalation, and intraperitoneal administration.

In an aspect, the present disclosure provides an isolated soluble fusion protein complex comprising at least two soluble proteins, where the first soluble protein comprises an interleukin-15 (IL-15) polypeptide domain and the second soluble protein comprises a soluble IL-15 receptor alpha sushi-binding domain (IL-15RαSu) fused to an immunoglobulin Fc domain, where one of the first or second soluble protein further comprises an IL-18 binding domain or functional fragment thereof, where one of the first or second soluble protein further comprises an IL-12 binding domain or functional fragment thereof and wherein the IL-15 domain of the first soluble protein binds to the IL-15RαSu domain of the second soluble protein to form a soluble fusion protein complex.

In an embodiment, the IL-15 polypeptide is an IL-15 variant comprising an N72D mutation (IL-15N72D).

In an embodiment, the IL-12 binding domain comprises the p40 and p35 subunits of IL-12. In an embodiment, the p40 and p35 subunits of IL-12 are linked by a flexible polypeptide linker into a single-chain format.

In an embodiment, the first soluble protein comprises the amino acid sequence set forth in one of SEQ ID NOs: 2 or 6.

In an embodiment, the second soluble protein comprises the amino acid sequence set forth in one of SEQ ID NOs: 4 or 8.

In an embodiment, a first soluble fusion protein complex may be covalently linked to a second soluble fusion protein complex.

In an embodiment, the first soluble fusion protein complex is covalently linked to the second soluble fusion protein complex by a disulfide bond linking the Fc domain of the first soluble fusion protein complex to the Fc domain of the second soluble fusion protein complex.

In an embodiment, the first or second soluble protein further comprises a binding domain that recognizes a disease antigen.

In an embodiment, the first or second soluble protein further comprises a binding domain that recognizes an immune checkpoint or signaling molecule.

In an embodiment, the disease antigen is associated with neoplasia or infectious disease.

In an embodiment, the first soluble protein is encoded by the sequence set forth in one of SEQ ID NOs: 1 or 5. In an embodiment, the nucleic acid sequence further comprises a promoter, translation initiation signal, and leader sequence operably linked to the sequence encoding the soluble protein.

In an embodiment, the second soluble protein may be encoded by the nucleic acid sequence set forth in one of SEQ ID NOs: 3 or 7. In an embodiment, the nucleic acid sequence further comprises a promoter, translation initiation signal, and leader sequence operably linked to the sequence encoding the soluble protein.

In an embodiment, a DNA vector may comprise any of the above enumerated nucleic acid sequences.

In an embodiment, a method for enhancing immune function, the method comprising: a) contacting a plurality of cells with any of the above soluble fusion protein complexes, where the plurality of cells further comprises immune cells comprising the IL-15R chains recognized by the IL-15 domain, the IL-12R chains recognized by the IL-12 domain and/or the IL-18R chains recognized by the IL-18 domain, and b) activating the immune cells via signaling of the IL-15R, IL-12R and/or IL-18R.

In an aspect, the present disclosure provides a method for killing a target cell, comprising: a) contacting a plurality of cells with any of the above soluble fusion protein complexes, where the plurality of cells further include immune cells comprising the IL-15R chains recognized by the IL-15 domain, the IL-12R chains recognized by the IL-12 domain and/or the IL-18R chains recognized by the IL-18 domain, and the target disease cells, b) activating the immune cells via signaling of the IL-15R, IL-12R and/or IL-18R, and c) killing the target disease cells by the activated immune cells.

In an embodiment, the target cells are tumor cells or infected cells.

In an aspect, the present disclosure provides a method of enhancing immune responses in a subject, comprising: a) contacting a plurality of cells with any of the above soluble fusion protein complexes, where the plurality of cells further include immune cells comprising the IL-15R chains recognized by the IL-15 domain, the IL-12R chains recognized by the IL-12 domain and/or the IL-18R chains recognized by the IL-18 domain, b) activating the immune cells via signaling of the IL-15R, IL-12R and/or IL-18R, c) administering (or adoptively transfer) to the patient the activated immune cells; and d) enhancing immune responses in the patient.

In an aspect, the present disclosure provides a method of preventing or treating disease in a patient, comprising: a) contacting a plurality of cells with a soluble fusion protein complex, wherein the plurality of cells further include immune cells comprising the IL-15R chains recognized by the IL-15 domain, the IL-12R chains recognized by the IL-12 domain and/or the IL-18R chains recognized by the IL-18 domain, b) activating the immune cells via signaling of the IL-15R, IL-12R and/or IL-18R, c) administering (or adoptively transfer) an effective amount of the activated immune cells to the patient, and d) damaging or killing the disease cells via the activated immune cells sufficient to prevent or treat the disease in the patient.

In an embodiment, the disease is a neoplasia or infectious disease.

In an aspect, the present disclosure provides a method of enhancing immune responses in a subject comprising administering to the subject an effective amount of any of the above soluble fusion protein complexes.

In an aspect, the present disclosure provides a method for treating a neoplasia or infectious disease in a subject in need thereof comprising administering to said subject an effective amount of a pharmaceutical composition comprising any of the above soluble fusion protein complexes, thereby treating said neoplasia or infectious disease.

In an embodiment, the neoplasia is selected from the group consisting of a glioblastoma, prostate cancer, hematological cancer, B-cell neoplasms, multiple myeloma, B-cell lymphoma, B cell non-Hodgkin lymphoma, Hodgkin's lymphoma, chronic lymphocytic leukemia, acute myeloid leukemia, cutaneous T-cell lymphoma, T-cell lymphoma, a solid tumor, urothelial/bladder carcinoma, melanoma, lung cancer, renal cell carcinoma, breast cancer, gastric and esophageal cancer, prostate cancer, pancreatic cancer, colorectal cancer, ovarian cancer, non-small cell lung carcinoma, and squamous cell head and neck carcinoma.

In an embodiment, the immune cells are NK cells or cytokine induced memory like (CIML) NK cells.

In an embodiment, the effective amounts of the activated immune cells are between $1\times10^4$ cells/kg and $1\times10^{10}$ cells/kg.

In an embodiment, the immune cells are administered at least one time per week.

In an embodiment, the effective amount is between about 1 and 100 µg/kg said fusion protein complex.

In an embodiment, the fusion protein complex is administered at least one time per week.

In an embodiment, the fusion protein complex increases immune cell proliferation, activation markers, cytotoxicity against target cells, and/or production of pro inflammatory cytokines, including IFN-γ.

Preferably, the fusion protein complex increases serum levels of interferon gamma (IFN-γ), and/or stimulates CD4$^+$ and CD8$^+$ T cells and NK cells to kill diseased cells or tumor cells in a subject.

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

By "agent" is meant a peptide, nucleic acid molecule, or small compound.

By "TxM" is meant a fusion protein complex comprising an IL-15N72D:IL-15RαSu/Fc scaffold linked to a binding domain (FIGS. 1A, 1B). An exemplary TxM is an IL-15N72D:IL-15RαSu fusion protein complex comprising fusions to IL-12 and IL-18 cytokines.

By "ameliorate" is meant decrease, suppress, attenuate, diminish, arrest, or stabilize the development or progression of a disease.

By "analog" is meant a molecule that is not identical, but has analogous functional or structural features. For example, a polypeptide analog retains the biological activity of a corresponding naturally-occurring polypeptide, while having certain biochemical modifications that enhance the analog's function relative to a naturally occurring polypeptide. Such biochemical modifications could increase the analog's protease resistance, membrane permeability, or half-life, without altering, for example, ligand binding. An analog may include an unnatural amino acid.

The invention includes antibodies or fragments of such antibodies, so long as they exhibit the desired biological activity. Also included in the invention are chimeric antibodies, such as humanized antibodies. Generally, a humanized antibody has one or more amino acid residues introduced into it from a source that is non-human. Humanization can be performed, for example, using methods described in the art, by substituting at least a portion of a rodent complementarity-determining region for the corresponding regions of a human antibody.

The term "antibody" or "immunoglobulin" is intended to encompass both polyclonal and monoclonal antibodies. The preferred antibody is a monoclonal antibody reactive with the antigen. The term "antibody" is also intended to encompass mixtures of more than one antibody reactive with the antigen (e.g., a cocktail of different types of monoclonal antibodies reactive with the antigen). The term "antibody" is further intended to encompass whole antibodies, biologically functional fragments thereof, single-chain antibodies, and genetically altered antibodies such as chimeric antibodies comprising portions from more than one species, bifunctional antibodies, antibody conjugates, humanized and human antibodies.

Biologically functional antibody fragments, which can also be used, are those peptide fragments derived from an antibody that are sufficient for binding to the antigen. "Antibody" as used herein is meant to include the entire antibody as well as any antibody fragments (e.g. F(ab')$_2$, Fab', Fab, Fv) capable of binding the epitope, antigen or antigenic fragment of interest.

By "binding to" a molecule is meant having a physicochemical affinity for that molecule.

The term "binding domain" is intended to encompass an antibody, single chain antibody, Fab, Fv, T-cell receptor binding domain, ligand binding domain, receptor binding domain, or other antigen-specific polypeptides known in the art.

As used herein, the term "biologically active polypeptide" or "effector molecule" is meant an amino acid sequence such as a protein, polypeptide or peptide; a sugar or polysaccharide; a lipid or a glycolipid, glycoprotein, or lipoprotein that can produce the desired effects as discussed herein. Effector molecules also include chemical agents. Also contemplated are effector molecule nucleic acids encoding a biologically active or effector protein, polypeptide, or peptide. Thus, suitable molecules include regulatory factors, enzymes, antibodies, or drugs as well as DNA, RNA, and oligonucleotides. The biologically active polypeptides or effector molecule can be naturally-occurring or it can be synthesized from known components, e.g., by recombinant or chemical synthesis and can include heterologous components. A biologically active polypeptide or effector molecule is generally between about 0.1 to 100 KD or greater up to about 1000 KD, preferably between about 0.1, 0.2, 0.5, 1, 2, 5, 10, 20, 30 and 50 KD as judged by standard molecule sizing techniques such as centrifugation or SDS-polyacrylamide gel electrophoresis. Desired effects of the invention include, but are not limited to, for example, forming a fusion protein complex of the invention with increased binding activity, killing a target cell, e.g. either to induce cell proliferation or cell death, initiate an immune response, in preventing or treating a disease, or to act as a detection molecule for diagnostic purposes. For such detection, an assay could be used, for example an assay that includes sequential steps of culturing cells to proliferate same, and contacting the cells with a fusion protein complex of the invention and then evaluating whether the fusion protein complex inhibits further development of the cells.

Covalently linking the effector molecule to the fusion protein complexes of the invention in accordance with the invention provides a number of significant advantages. Fusion protein complexes of the invention can be produced that contain a single effector molecule, including a peptide of known structure. Additionally, a wide variety of effector molecules can be produced in similar DNA vectors. That is, a library of different effector molecules can be linked to the fusion protein complexes for recognition of infected or diseased cells. Further, for therapeutic applications, rather than administration of the fusion protein complex of the invention to a subject, a DNA expression vector coding for the fusion protein complex can be administered for in vivo expression of the fusion protein complex. Such an approach avoids costly purification steps typically associated with preparation of recombinant proteins and avoids the complexities of antigen uptake and processing associated with conventional approaches.

As noted, components of the fusion proteins disclosed herein, e.g., effector molecule such as cytokines, chemokines, growth factors, protein toxins, immunoglobulin domains or other bioactive molecules and any peptide linkers, can be organized in nearly any fashion provided that the fusion protein has the function for which it was intended. In particular, each component of the fusion protein can be spaced from another component by at least one suitable peptide linker sequence if desired. Additionally, the fusion proteins may include tags, e.g., to facilitate modification, identification and/or purification of the fusion protein. More specific fusion proteins are in the Examples described below.

"Detect" refers to identifying the presence, absence or amount of the analyte to be detected.

By "disease" is meant any condition or disorder that damages or interferes with the normal function of a cell, tissue, or organ. Examples of diseases include neoplasias and viral infections.

By the terms "effective amount" and "therapeutically effective amount" of a formulation or formulation component is meant a sufficient amount of the formulation or component, alone or in a combination, to provide the desired effect. For example, by "an effective amount" is meant an amount of a compound, alone or in a combination, required to ameliorate the symptoms of a disease relative to an untreated patient. The effective amount of active compound(s) used to practice the present invention for therapeutic treatment of a disease varies depending upon the manner of administration, the age, body weight, and general health of the subject. Ultimately, the attending physician or veterinarian will decide the appropriate amount and dosage regimen. Such amount is referred to as an "effective" amount.

By "fragment" is meant a portion of a polypeptide or nucleic acid molecule. This portion contains, preferably, at least 10%, 20%, 30%, 40%, 50%, 60%, 70%, 80%, or 90% of the entire length of the reference nucleic acid molecule or polypeptide. For example, a fragment may contain 10, 20, 30, 40, 50, 60, 70, 80, 90, or 100, 200, 300, 400, 500, 600, 700, 800, 900, or 1000 nucleotides or amino acids. However, the invention also comprises polypeptides and nucleic acid fragments, so long as they exhibit the desired biological activity of the full length polypeptides and nucleic acid, respectively. A nucleic acid fragment of almost any length is employed. For example, illustrative polynucleotide segments with total lengths of about 10,000, about 5,000, about 3,000, about 2,000, about 1,000, about 500, about 200, about 100, about 50 base pairs in length (including all intermediate lengths) are included in many implementations of this invention. Similarly, a polypeptide fragment of almost any length is employed. For example, illustrative polypeptide segments with total lengths of about 10,000, about 5,000, about 3,000, about 2,000, about 1,000, about 5,000, about 1,000, about 500, about 200, about 100, or about 50 amino acids in length (including all intermediate lengths) are included in many implementations of this invention.

The terms "isolated", "purified", or "biologically pure" refer to material that is free to varying degrees from components which normally accompany it as found in its native state. "Isolate" denotes a degree of separation from original source or surroundings. "Purify" denotes a degree of separation that is higher than isolation.

A "purified" or "biologically pure" protein is sufficiently free of other materials such that any impurities do not materially affect the biological properties of the protein or cause other adverse consequences. That is, a nucleic acid or peptide of this invention is purified if it is substantially free of cellular material, viral material, or culture medium when produced by recombinant DNA techniques, or chemical precursors or other chemicals when chemically synthesized. Purity and homogeneity are typically determined using analytical chemistry techniques, for example, polyacrylamide gel electrophoresis or high performance liquid chromatography. The term "purified" can denote that a nucleic acid or protein gives rise to essentially one band in an electrophoretic gel. For a protein that can be subjected to modifications, for example, phosphorylation or glycosylation, different modifications may give rise to different isolated proteins, which can be separately purified.

Similarly, by "substantially pure" is meant a nucleotide or polypeptide that has been separated from the components that naturally accompany it. Typically, the nucleotides and polypeptides are substantially pure when they are at least 60%, 70%, 80%, 90%, 95%, or even 99%, by weight, free from the proteins and naturally-occurring organic molecules with they are naturally associated.

By "isolated nucleic acid" is meant a nucleic acid that is free of the genes which flank it in the naturally-occurring genome of the organism from which the nucleic acid is derived. The term covers, for example: (a) a DNA which is part of a naturally occurring genomic DNA molecule, but is not flanked by both of the nucleic acid sequences that flank that part of the molecule in the genome of the organism in which it naturally occurs; (b) a nucleic acid incorporated into a vector or into the genomic DNA of a prokaryote or eukaryote in a manner, such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion protein. Isolated nucleic acid molecules according to the present invention further include molecules produced synthetically, as well as any nucleic acids that have been altered chemically and/or that have modified backbones. For example, the isolated nucleic acid is a purified cDNA or RNA polynucleotide. Isolated nucleic acid molecules also include messenger ribonucleic acid (mRNA) molecules.

By an "isolated polypeptide" is meant a polypeptide of the invention that has been separated from components that naturally accompany it. Typically, the polypeptide is isolated when it is at least 60%, by weight, free from the proteins and naturally-occurring organic molecules with which it is naturally associated. Preferably, the preparation is at least 75%, more preferably at least 90%, and most preferably at least 99%, by weight, a polypeptide of the invention. An isolated polypeptide of the invention may be obtained, for example, by extraction from a natural source, by expression of a recombinant nucleic acid encoding such a polypeptide; or by chemically synthesizing the protein. Purity can be measured by any appropriate method, for example, column chromatography, polyacrylamide gel electrophoresis, or by HPLC analysis.

By "marker" is meant any protein or polynucleotide having an alteration in expression level or activity that is associated with a disease or disorder.

By "neoplasia" is meant a disease or disorder characterized by excess proliferation or reduced apoptosis. Illustrative neoplasms for which the invention can be used include, but are not limited to leukemias (e.g., acute leukemia, acute lymphocytic leukemia, acute myelocytic leukemia, acute myeloblastic leukemia, acute promyelocytic leukemia, acute myelomonocytic leukemia, acute monocytic leukemia, acute erythroleukemia, chronic leukemia, chronic myelocytic leukemia, chronic lymphocytic leukemia), polycythemia vera, lymphoma (Hodgkin's disease, non-Hodgkin's disease), Waldenstrom's macroglobulinemia, heavy chain disease, and solid tumors such as sarcomas and carcinomas (e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, nile duct carcinoma, choriocarcinoma, seminoma, embryonal carcinoma, Wilm's tumor, cervical cancer, uterine cancer, testicular cancer, lung carcinoma, small cell lung carcinoma, bladder carcinoma, epithelial carcinoma, glioma, glioblastoma multiforme, astrocytoma, medulloblastoma, craniopharyngioma, ependymoma, pinealoma, hemangioblastoma, acoustic neuroma, oligodenroglioma, schwannoma, meningioma, melanoma, neuroblastoma, and retinoblastoma). In particular embodiments, the neoplasia is multiple myeloma, beta-cell lymphoma, urothelial/bladder carcinoma or melanoma. As used herein, "obtaining" as in "obtaining an agent" includes synthesizing, purchasing, or otherwise acquiring the agent.

By "reduces" is meant a negative alteration of at least 5%, 10%, 25%, 50%, 75%, or 100%.

By "reference" is meant a standard or control condition.

A "reference sequence" is a defined sequence used as a basis for sequence comparison. A reference sequence may be a subset of or the entirety of a specified sequence; for example, a segment of a full-length cDNA or gene sequence, or the complete cDNA or gene sequence. For polypeptides, the length of the reference polypeptide sequence will generally be at least about 16 amino acids, preferably at least about 20 amino acids, more preferably at least about 25 amino acids, and even more preferably about 35 amino acids, about 50 amino acids, or about 100 amino acids. For nucleic acids, the length of the reference nucleic acid sequence will generally be at least about 50 nucleotides, preferably at least about 60 nucleotides, more preferably at least about 75 nucleotides, and even more preferably about 100 nucleotides or about 300 nucleotides or any integer thereabout or therebetween.

By "specifically binds" is meant a compound or antibody that recognizes and binds a polypeptide of the invention, but which does not substantially recognize and bind other molecules in a sample, for example, a biological sample, which naturally includes a polypeptide of the invention.

Nucleic acid molecules useful in the methods of the invention include any nucleic acid molecule that encodes a polypeptide of the invention or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. Nucleic acid molecules useful in the methods of the invention include any nucleic acid molecule that encodes a polypeptide of the invention or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. By "hybridize" is meant pair to form a double-stranded molecule between complementary polynucleotide sequences (e.g., a gene described herein), or portions thereof, under various conditions of stringency. (See, e.g., Wahl, G. M. and S. L. Berger (1987) Methods Enzymol. 152:399; Kimmel, A. R. (1987) Methods Enzymol. 152:507).

For example, stringent salt concentration will ordinarily be less than about 750 mM NaCl and 75 mM trisodium citrate, preferably less than about 500 mM NaCl and 50 mM trisodium citrate, and more preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and more preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred: embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 µg/ml denatured salmon sperm DNA (ssDNA). In a most preferred embodiment, hybridization will occur at 42° C. in 250 mM NaCl, 25 mM trisodium citrate, 1% SDS, 50% formamide, and 200 µg/ml ssDNA. Useful variations on these conditions will be readily apparent to those skilled in the art.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., more preferably of at least about 42° C., and even more preferably of at least about 68° C. In a preferred embodiment, wash steps will occur at 25° C. in 30 mM NaCl, 3 mM trisodium citrate, and 0.1%

SDS. In a more preferred embodiment, wash steps will occur at 42° C. in 15 mM NaCl, 1.5 mM trisodium citrate, and 0.1% SDS. In a more preferred embodiment, wash steps will occur at 68° C. in 15 mM NaCl, 1.5 mM trisodium citrate, and 0.1% SDS. Additional variations on these conditions will be readily apparent to those skilled in the art. Hybridization techniques are well known to those skilled in the art and are described, for example, in Benton and Davis (Science 196:180, 1977); Grunstein and Hogness (Proc. Natl. Acad. Sci., USA 72:3961, 1975); Ausubel et al. (Current Protocols in Molecular Biology, Wiley Interscience, New York, 2001); Berger and Kimmel (Guide to Molecular Cloning Techniques, 1987, Academic Press, New York); and Sambrook et al., Molecular Cloning: A Laboratory Manual, Cold Spring Harbor Laboratory Press, New York.

By "substantially identical" is meant a polypeptide or nucleic acid molecule exhibiting at least 50% identity to a reference amino acid sequence (for example, any one of the amino acid sequences described herein) or nucleic acid sequence (for example, any one of the nucleic acid sequences described herein). Preferably, such a sequence is at least 60%, more preferably 80% or 85%, and more preferably 90%, 95% or even 99% identical at the amino acid level or nucleic acid to the sequence used for comparison.

Sequence identity is typically measured using sequence analysis software (for example, Sequencher, Gene Codes Corporation, 775 Technology Drive, Ann Arbor, MI; Vector NTI, Life Technologies, 3175 Staley Rd. Grand Island, NY). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between $e^{-3}$ and $e^{-100}$ indicating a closely related sequence.

By "subject" is meant a mammal, including, but not limited to, a human or non-human mammal, such as a bovine, equine, canine, ovine, or feline. The subject is preferably a mammal in need of such treatment, e.g., a subject that has been diagnosed with B cell lymphoma or a predisposition thereto. The mammal is any mammal, e.g., a human, a primate, a mouse, a rat, a dog, a cat, a horse, as well as livestock or animals grown for food consumption, e.g., cattle, sheep, pigs, chickens, and goats. In a preferred embodiment, the mammal is a human.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

The terms "treating" and "treatment" as used herein refer to the administration of an agent or formulation to a clinically symptomatic individual afflicted with an adverse condition, disorder, or disease, so as to affect a reduction in severity and/or frequency of symptoms, eliminate the symptoms and/or their underlying cause, and/or facilitate improvement or remediation of damage. It will be appreciated that, although not precluded, treating a disorder or condition does not require that the disorder, condition or symptoms associated therewith be completely eliminated. Agents or formulations used in treatment may comprise cells or tissues.

Treatment of patients with neoplasia may include any of the following: Adjuvant therapy (also called adjunct therapy or adjunctive therapy) to destroy residual tumor cells that may be present after the known tumor is removed by the initial therapy (e.g. surgery), thereby preventing possible cancer reoccurrence; neoadjuvant therapy given prior to the surgical procedure to shrink the cancer; induction therapy to cause a remission, typically for acute leukemia; consolidation therapy (also called intensification therapy) given once a remission is achieved to sustain the remission; maintenance therapy given in lower or less frequent doses to assist in prolonging a remission; first line therapy (also called standard therapy); second (or 3rd, 4th, etc.) line therapy (also called salvage therapy) is given if a disease has not responded or reoccurred after first line therapy; and palliative therapy (also called supportive therapy) to address symptom management without expecting to significantly reduce the cancer.

The terms "preventing" and "prevention" refer to the administration of an agent or composition to a clinically asymptomatic individual who is susceptible or predisposed to a particular adverse condition, disorder, or disease, and thus relates to the prevention of the occurrence of symptoms and/or their underlying cause.

Unless specifically stated or obvious from context, as used herein, the term "or" is understood to be inclusive. Unless specifically stated or obvious from context, as used herein, the terms "a", "an", and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

The transitional term "comprising," which is synonymous with "including," "containing," or "characterized by," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

Other features and advantages of the invention will be apparent from the following description of the preferred embodiments thereof, and from the claims. Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All published foreign patents and patent applications cited herein are incorporated herein by reference.

Genbank and NCBI submissions indicated by accession number cited herein are incorporated herein by reference. All other published references, documents, manuscripts and scientific literature cited herein are incorporated herein by reference. In the case of conflict, the present specification, including definitions, will control. In addition, the materials, methods, and examples are illustrative only and not intended to be limiting.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 2B is a line graph showing the chromatographic profile of Protein A-purified hIL18/IL12/TxM protein following elution on a preparative size exclusion column. FIG. 2C is a line graph showing the chromatographic profile of Protein A/SEC-purified hIL18/IL12/TxM protein following elution on an analytical size exclusion column, demonstrating separation of monomeric multiprotein hIL18/IL12/TxM fusion protein complexes from protein aggregates.

DETAILED DESCRIPTION

Therapies employing natural killer (NK) cells and T cells have emerged as potential treatments for cancer and viral infections due to the ability of these cells to kill diseased cells and release pro-inflammatory cytokines (See, e.g., Fehniger T A and Cooper M A. Trends Immunol. 2016; 37:877-888; and Cerwenka A and Lanier L L. Nat Rev Immunol. 2016 16:112-23). Of particular interest are cytokine-induced memory-like (CIML) natural killer (NK) cells, which exhibit long-lasting non-antigen-specific NK cell effector function. These cells can be induced ex vivo following overnight stimulation of purified NK cells with saturating amounts of interleukin-12 (IL-12, 10 ng/ml), IL-15 (50 ng/ml), and IL-18 (50 ng/ml). These primed NK cells exhibit memory like properties such as 1) enhanced proliferation, 2) expression of IL-2 receptor α (IL-2Rα, CD25), perforin, granzymes, and other activation markers, and 3) increased interferon-γ (IFN-γ) production following re-stimulation.

Initial therapeutic evaluation of CIML NK cells in a first-in-human phase 1 clinical trial utilized ex vivo IL-12/IL-15/IL-18 stimulation of allogeneic haploidentical NK cells followed by adoptive transfer of the CIML NK cells into patients with relapsed or refractory acute myeloid leukemia (AML) who had been preconditioned with cyclophosphamide and fludarabine. Following transfer, patients received low dose IL-2 to support the cells in vivo. These transferred, primed NK cells peaked in frequency between 7 and 14 days after infusion, comprising greater than 90% of all NK cells in the blood 7 days after transfer. Of the nine evaluable patients at the time of publication, four had a complete remission, in addition to one patient having a morphologic leukemia free state, suggesting promising therapeutic activity mediated by the adoptively transferred CIML NK cells (See, Romee, R, et al. Sci Transl Med. 2016; 8:357ra123, incorporated herein by reference).

Prior to the invention described herein, optimal methods for generating CIML NK cells were not fully elucidated. Prior to the invention described herein, strategies employed recombinant human IL-12 (produced in insect cells), human IL-18 (produced in E. coli), and human IL-15 (produced in E. coli), which differ in glycosylation and potentially other post-transcriptional modifications compared to mammalian cell-produced cytokines. The recombinant cytokines may also have different purity and stability and are not generally available as clinical grade material. Additionally, each cytokine is expected to have unique receptor binding, internalization and recycling properties.

Figure 1A:
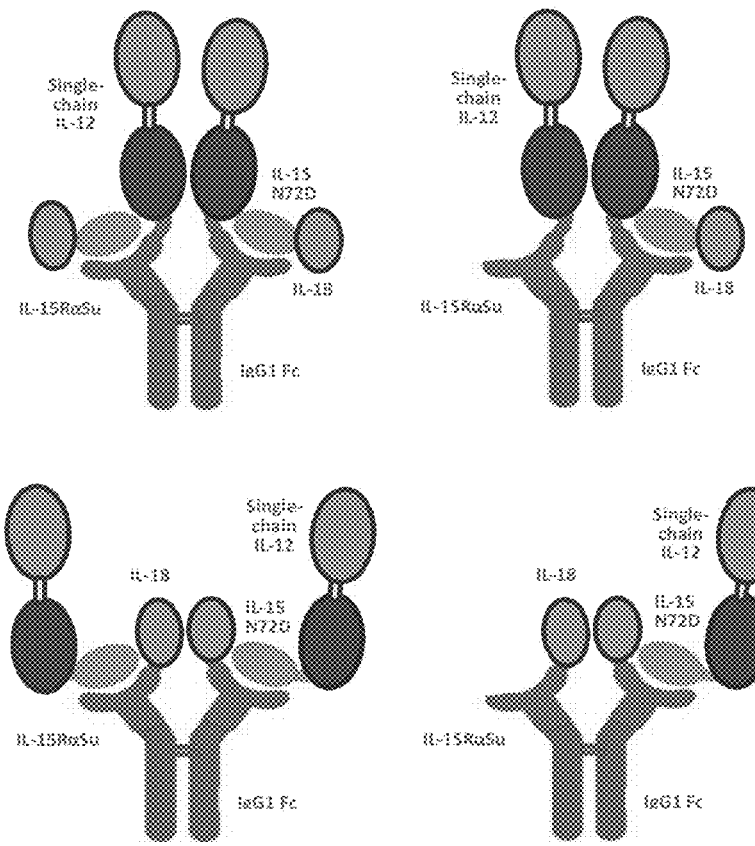
FIG. 1A is a schematic diagram illustrating different TxM fusion protein complexes comprising the IL-15N72D:IL-15RαSu/Fc scaffold fused to IL-12 and IL-18 binding domains. In some cases, the dimeric IL-15RαSu/Fc fusion protein complexes comprise one or two IL-15N72D fusion proteins.
Figure 1B:
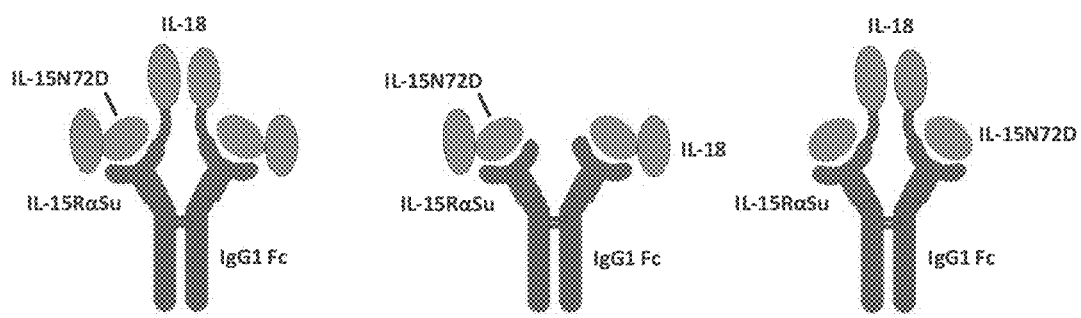
FIG. 1B is a schematic diagram illustrating different TxM fusion protein complexes comprising the IL-15N72D:IL-15RαSu/Fc scaffold fused to IL-18 binding domains.

Accordingly, described herein are multi-specific IL-15-based fusion protein complexes comprising IL-12 and IL-18 binding domains (FIG. 1A, 1B). Specifically, described herein are fusion protein complexes comprising an IL-15N72D:IL-15RαSu-Ig Fc scaffold fused to IL-12 and IL-18 binding domains. When characterized using human immune cells, these fusion protein complexes exhibit binding and biological activity of each of the IL-15, IL-12 and IL-18 cytokines. Additionally, these fusion protein complexes act to induce CIML NK cells with elevated activation markers, increased cytotoxicity against tumor cells and enhanced production of IFN-γ. Thus, the fusion protein complex as a single molecule binds to and signals via multiple cytokine receptors on NK cells to provide the synergistic responses previously only observed with a combination of multiple individual cytokines. Additionally, these fusion protein complexes comprise the Fc region of Ig molecules, which can form a dimer to provide a soluble multi-polypeptide complex, bind Protein A for the purpose of purification and interact with Fcγ receptors on NK cells and macrophages, thus providing advantages to the fusion protein complex that are not present in the combination of individual cytokines. Mammalian cell expression-based methods for making these fusion protein complexes suitable for large scale production of clinical grade material are described herein. Additional methods for making and using CIML NK cells induced by the fusion protein complex of the invention are also provided.

Interleukin-15

Interleukin-15 (IL-15) is an important cytokine for the development, proliferation, and activation of effector NK cells and CD8+ memory T cells. IL-15 binds to the IL-15 receptor α (IL-15Rα) and is presented in trans to the IL-2/IL-15 receptor β-common γ chain (IL-15Rβγ$_c$) complex on effector cells. IL-15 and IL-2 share binding to the IL-15Rβγ$_c$, and signal through STAT3 and STAT5 pathways. However, unlike IL-2, IL-15 does not support maintenance of CD4+CD25+FoxP3+ regulatory T (Treg) cells or induce cell death of activated CD8+ T cells, effects that may have limited the therapeutic activity of IL-2 against multiple myeloma. Additionally, IL-15 is the only cytokine known to provide anti-apoptotic signaling to effector CD8+ T cells. IL-15, either administered alone or as a complex with the IL-15Rα, exhibits potent anti-tumor activities against well-established solid tumors in experimental animal models and, thus, has been identified as one of the most promising immunotherapeutic drugs that could potentially cure cancer.

To facilitate clinical development of an IL-15-based cancer therapeutic, an IL-15 mutant (IL-15N72D) with increased biological activity compared to IL-15 was identified (Zhu et al., J Immunol, 183: 3598-3607, 2009). The pharmacokinetics and biological activity of this IL-15 super-agonist (IL-15N72D) was further improved by the creation of IL-15N72D:IL-15Rα/Fc fusion protein complex (ALT-803), such that the super agonist complex has at least 25-times the activity of the native cytokine in vivo (Han et al., Cytokine, 56: 804-810, 2011).

IL-15:IL-15Rα Protein Complex

As described above, an IL-15:IL-15Rα fusion protein complex can refer to a complex having IL-15 non-covalently bound to the soluble IL-15Rα domain of the native IL-15Rα. In some cases, the soluble IL-15Rα is covalently linked to a biologically active polypeptide and/or to an IgG Fc domain. The IL-15 can be either IL-15 or IL-15 covalently linked to a second biologically active polypeptide. The crystal structure of the IL-15:IL-15Rα protein complex is shown in Chirifu et al., 2007 Nat Immunol 8, 1001-1007, incorporated herein by reference.

In various embodiments of the above aspects or any other aspect of the invention delineated herein, the IL-15Rα fusion protein comprises soluble IL-15Rα, e.g., IL-15Rα covalently linked to a biologically active polypeptide (e.g., the heavy chain constant domain of IgG, an Fc domain of the heavy chain constant domain of IgG, or a cytokine). In other embodiments of the invention of the above aspects, IL-15 comprises IL-15, e.g., IL-15 covalently linked to a second biologically active polypeptide, e.g., a cytokine. In other embodiments, purifying the IL-15:IL-15Rα fusion protein complex from the host cell or media involves capturing the IL-15:IL-15Rα fusion protein complex on an affinity reagent that specifically binds the IL-15:IL-15Rα fusion protein complex. In other embodiments, the IL-15Rα fusion protein contains an IL-15Rα/Fc fusion protein and the affinity reagent specifically binds the Fc domain. In other embodiments, the affinity reagent is Protein A or Protein G. In other embodiments, the affinity reagent is an antibody. In other embodiments, purifying the IL-15:IL-15Rα fusion protein complex from the host cell or media comprises ion exchange chromatography. In other embodiments, purifying the IL-15:IL-15Rα fusion protein complex from the host cell or media comprises size exclusion chromatography.

In other embodiments, the IL-15Rα comprises IL-15RαSushi (IL-15RαSu). In other embodiments, the IL-15 is a variant IL-15 (e.g., IL-15N72D). In other embodiments, the IL-15 binding sites of the IL-15:IL-15Rα fusion protein complex are fully occupied. In other embodiments, both IL-15 binding sites of the IL-15:IL-15RαSu/Fc fusion protein complex are fully occupied. In other embodiments, the IL-15:IL-15Rα fusion protein complex is purified based on the fusion protein complex charge or size properties. In other embodiments, the fully occupied IL-15N72D:IL-15RαSu/Fc fusion protein complex is purified by anion exchange chromatography based on the fusion protein complex charge properties. In other embodiments, the fully occupied IL-15N72D:IL-15RαSu/Fc fusion protein complex is purified using a quaternary amine-based resin with binding conditions employing low ionic strength neutral pH buffers and elution conditions employing buffers of increasing ionic strength.

In certain embodiments, a soluble fusion protein complex comprises a first and second soluble protein, wherein: the first soluble protein comprises an interleukin-15 (IL-15) polypeptide domain linked to an IL-12 or IL-18 binding domain or functional fragment thereof; the second soluble protein comprises a soluble IL-15 receptor alpha sushi-binding domain (IL-15RαSu) fused to an immunoglobulin Fc domain, wherein the IL-15RαSu domain is linked to an IL-12 or IL-18 binding domain or functional fragment thereof; and, the IL-15 polypeptide domain of the first soluble protein binds to the IL-15RαSu domain of the second soluble protein to form a soluble fusion protein complex.

In certain embodiments, an isolated soluble fusion protein complex comprises an interleukin-15 (IL-15) polypeptide domain linked to an IL-12 and/or IL-18 binding domain or functional fragment thereof. In certain embodiments, the IL-15 polypeptide domain is an IL-15 variant comprising an N72D mutation (IL-15N72D).

In certain embodiments, an isolated soluble fusion protein complex comprising a soluble IL-15 receptor alpha sushi-binding domain (IL-15RαSu) fused to an immunoglobulin Fc domain, wherein the IL-15RαSu domain is linked to an IL-12 and/or IL-18 binding domain or functional fragment thereof.

The isolated protein fusion complex can be a "two headed" fusion protein complex. These complexes can vary in their combination of IL-15, IL-15RαSu/Fc, interleukins, comprising, for example, IL-18/IL-15RαSu/Fc and IL-15N72D fusion proteins or IL-15RαSu/Fc and IL-18/IL-15N72D fusion proteins (FIG. 1B). Similarly, these fusion protein complexes comprise IL-12/IL-15RαSu/Fc and IL-15N72D fusion proteins or IL-15RαSu/Fc and IL-12/IL-15N72D fusion proteins. The combinations can be varied, as well as the types of molecules which include variants, mutants, homologs, analogs, modified molecules and the like.

Accordingly, in certain embodiments, an isolated soluble fusion protein complex comprises a first and second soluble protein, wherein the first soluble protein comprises an interleukin-15 receptor alpha sushi-binding domain (IL-15RαSu) fused to an immunoglobulin Fc domain, wherein the IL-15RαSu domain is fused to an IL-18 binding domain or functional fragment thereof; the second soluble protein comprises an interleukin-15 (IL-15) polypeptide domain fused to an IL-18 domain; wherein the IL-15 polypeptide domain of the first soluble protein binds to the IL-15RαSu domain of the second soluble protein to form a soluble fusion protein complex.

In other embodiments, an isolated soluble fusion protein complex comprises a first and second soluble protein, wherein the first soluble protein comprises an interleukin-15 receptor alpha sushi-binding domain (IL-15RαSu) fused to an immunoglobulin Fc domain, wherein the IL-15RαSu domain is fused to an IL-12 binding domain or functional fragment thereof; the second soluble protein comprises an interleukin-15 (IL-15) polypeptide domain fused to an IL-12 domain; wherein the IL-15 polypeptide domain of the first soluble protein binds to the IL-15RαSu domain of the second soluble protein to form a soluble fusion protein complex.

In certain embodiments, an isolated soluble fusion protein comprises an interleukin-15 polypeptide domain, a first and second soluble protein wherein the first soluble protein comprises an interleukin-15 receptor alpha sushi-binding domain (IL-15RαSu) fused to an immunoglobulin Fc domain, wherein the IL-15RαSu domain is linked to an IL-12 and/or IL-18 binding domain or functional fragment thereof and a second soluble protein comprising an interleukin-15 receptor alpha sushi-binding domain (IL-15RαSu) fused to an immunoglobulin Fc domain, wherein the IL-15RαSu domain is linked to an IL-12 and/or IL-18 binding domain or functional fragment thereof, and, wherein the IL-15 polypeptide domain binds to the IL-15RαSu domain of the first and/or second soluble protein to form a soluble fusion protein complex.

In another embodiment, an isolated soluble fusion protein comprises an interleukin-15 receptor alpha sushi-binding domain (IL-15RαSu) fused to an immunoglobulin Fc domain, a first and second soluble protein wherein the first soluble protein comprises an interleukin-15 polypeptide domain linked to an IL-12 and/or IL-18 binding domain or functional fragment thereof and a second soluble protein comprising an interleukin-15 polypeptide domain linked to an IL-12 and/or IL-18 binding domain or functional fragment thereof, and, wherein the IL-15 polypeptide domain of the first and/or second soluble protein binds to the IL-15RαSu domain to form a soluble fusion protein complex.

In certain embodiments of the soluble fusion protein complexes of the invention, the IL-15 polypeptide is an IL-15 variant having a different amino acid sequence than native IL-15 polypeptide. The human IL-15 polypeptide is referred to herein as huIL-15, hIL-15, huIL15, hIL15, IL-15 wild type (wt) and variants thereof are referred to using the native amino acid, its position in the mature sequence and the variant amino acid. For example, huIL15N72D refers to human IL-15 comprising a substitution of N to D at position 72. In certain embodiments, the IL-15 variant functions as an IL-15 agonist as demonstrated, e.g., by increased binding activity for the IL-15RβγC receptors compared to the native IL-15 polypeptide. In certain embodiments, the IL-15 variant functions as an IL-15 antagonist as demonstrated by e.g., decreased binding activity for the IL-15RβγC receptors compared to the native IL-15 polypeptide. In certain embodiments, the IL-15 variant has increased binding affinity or a decreased binding activity for the IL-15RβγC receptors compared to the native IL-15 polypeptide. In certain embodiments, the sequence of the IL-15 variant has at least one (i.e., 1, 2, 3, 4, 5, 6, 7, 8, 9, 10, or more) amino acid change compared to the native IL-15 sequence. The amino acid change can include one or more of an amino acid substitution or deletion in the domain of IL-15 that interacts with IL-15Rβ and/or IL-15RγC. In certain embodiments, the amino acid change is one or more amino acid substitutions or deletions at position 8, 61, 65, 72, 92, 101, 108, or 111 of the mature human IL-15 sequence. For example, the amino acid change is the substitution of D to N or A at position 8, D to A at position 61, N to A at position 65, N to R at position 72 or Q to A at position 108 of the mature human IL-15 sequence, or any combination of these substitutions. In certain embodiments, the amino acid change is the substitution of N to D at position 72 of the mature human IL-15 sequence.

ALT-803

ALT-803 comprises an IL-15 mutant with increased ability to bind IL-2Rβγ and enhanced biological activity (U.S. Pat. No. 8,507,222, incorporated herein by reference). This super-agonist mutant of IL-15 was described in a publication (Zu et al., 2009 J Immunol, 183: 3598-3607, incorporated herein by reference). This IL-15 super-agonist in combination with a soluble IL-15a receptor fusion protein (IL-15RαSu/Fc) results in a fusion protein complex with highly potent IL-15 activity in vitro and in vivo (Han et al., 2011, Cytokine, 56: 804-810; Xu, et al., 2013 Cancer Res. 73:3075-86, Wong, et al., 2013, OncoImmunology 2: e26442). The IL-15 super agonist complex comprises an IL-15 mutant (IL-15N72D) bound to an IL-15 receptor α/IgG1 Fc fusion protein (IL-15N72D:IL-15RαSu/Fc) is referred to as "ALT-803."

Pharmacokinetic analysis indicated that the fusion protein complex has a half-life of 25 hours following i.v. administration in mice. ALT-803 exhibits impressive anti-tumor activity against aggressive solid and hematological tumor models in immunocompetent mice. It can be administered as a monotherapy using a twice weekly or weekly i.v. dose regimen or as combinatorial therapy with an antibody. The ALT-803 anti-tumor response is also durable. Tumor-bearing mice that were cured after ALT-803 treatment were also highly resistant to re-challenge with the same tumor cells indicating that ALT-803 induces effective immunological memory responses against the re-introduced tumor cells.

The sequence for ALT-803 (IL-15N72D associated with a dimeric IL-15RαSu/Fc fusion protein) comprises SEQ ID NO: 9:

```
IL-15N72D protein sequence (with leader peptide)
[Leader peptide]
METDTLLLWVLLLWVPGSTG-

[IL-15N72D]
NWVNVISDLKKIEDLIQSMHIDATLYTESDVHPSCKVTAMKCFLLELQVI

SLESGDASIHDTVENLIILANDSLSSNGNVTESGCKECEELEEKNIKEFL

QSFVHIVQMFINTS

IL-15RαSu/Fc protein sequence (with leader
peptide)
[Leader peptide]
MDRLTSSFLLLIVPAYVLS-

[IL-15RαSu]
ITCPPPMSVEHADIWVKSYSLYSRERYICNSGFKRKAGTSSLTECVLNKA

TNVAHWTTPSLKCIR-

[IgG1 CH2-CH3 (Fc domain)]
EPKSCDKTHTCPPCPAPELLGGPSVFLFPPKPKDTLMISRTPEVTCVVVD

VSHEDPEVKFNWYVDGVEVHNAKTKPREEQYNSTYRVVSVLTVLHQDWLN

GKEYKCKVSNKALPAPIEKTISKAKGQPREPQVYTLPPSRDELTKNQVSL

TCLVKGFYPSDIAVEWESNGQPENNYKTTPPVLDSDGSFFLYSKLTVDKS

RWQQGNVFSCSVMHEALHNHYTQKSLSLSPGK
```

IL-12

IL-12 is a member of a cytokine family consists of IL-12, IL-23, IL-27 and IL-35, which have diverse functions and play a role in both pro- and anti-inflammatory responses. IL-12 is typically expressed by activated antigen presenting cells (APCs). IL-12 promotes Th1 differentiation and IFN-γ production by T cells, and plays a role in induction of anti-tumor responses. As described herein, IL-12 in combination with IL-15 and IL-18 is capable of inducing CIML NK cells.

IL-12 is a disulfide-linked heterodimer consisting an α subunit (p35) and a β subunit (p40) in which the α subunit consists of a four-helix bundle long-chain cytokine and the β subunit are homologous to non-signaling receptors of the IL-6 family. Crystal structure and mutagenesis analyses of IL-12 have defined amino acid residues at the p35/p40 interface important for subunit interactions (Yoon, et al. 0.2000, EMBO J. 9, 3530-354). For example, a key arginine residue in p35 (R189) interacts with an aspartic acid in p40 (D290), such that the R189 side chain is buried in a hydrophilic pocket on p40. Additionally, conformation changes in p40 may be important in optimizing these interactions. Based on this information, IL-12 variants containing amino acid changes could be generated that exhibit improved subunit interactions. Moreover, single-chain forms of IL-12 can be generated consisting of the p35 subunit linked to the p40 subunit by a flexible linker, either through the C-terminus of p35 linked to the N-terminus of p40 or vice versa. Such variants could be incorporated into the fusion protein complex of the invention to optimize expression, subunit interactions and/or stability of the IL-12 binding domain. Similarly, the IL-12 genes and expression constructs could be modified (i.e., codon optimization, removal of secondary structures) to improve gene expression, translation, post translational modification and/or secretion.

The actions of IL-12 are mediated by binding to a transmembrane receptor comprised of two subunits (IL-12Rβ1 and IL-12Rβ2). Each subunit of the receptor is composed of an extracellular ligand-binding domain, a transmembrane domain and a cytosolic domain that mediates binding of Janus-family tyrosine kinases. IL-12 binding is believed to result in heterodimerization of β1 and β2 and the generation of a high-affinity receptor complex capable of signal transduction. In this model, dimerization of the receptor leads to juxtaposition of the cytosolic domains and the subsequent tyrosine phosphorylation and activation of the receptor-associated Janus-family kinases, Jak2 and Tyk-2. These activated kinases, in turn, tyrosine phosphorylate and activate several members of the signal transducer and activator of transcription (STAT) family (STAT-1, -3 and -4). The STATs translocate to the nucleus to activate transcription of several immune-responsive genes, including IFN-γ. Although the crystal structure of the IL-12:IL-12R complex has not yet been determined, IL-12 variants with increased receptor binding/signaling activity can be isolated by standard screening assays (Leong et al. 2003, PNAS 100:1163-1168). Fragments of the IL-12 heterodimer, including just the p35 subunit, may exhibit biological activity. IL-12 variants could also be isolated that modify IL-12/IL-12R surface residence time, turnover and/or recycling. Moreover, IL-12 variants could be incorporated into the fusion protein complex of the invention to optimize and/or balance the combined cytokine activities to induce immune cell responses, particularly CIML NK cell activity.

IL-18

Interleukin 18 (IL-18) is a pleiotropic IL-1 superfamily cytokine involved in the regulation of innate and acquired immune response. In the milieu of IL-12 or IL-15, IL-18 is a potent inducer of IFN-γ in NK cells and CD4 T helper (Th) 1 lymphocytes. However, IL-18 also modulates Th2 and Th17 cell responses, as well as the activity of CD8 cytotoxic cells and neutrophils, in a host microenvironment-dependent manner. The biological activity of IL-18 is mediated by its binding to the heterodimeric IL-18Rα/β complexes expressed on T cells, NK cells, macrophages, neutrophils, and endothelial cells which induces downstream signals leading to the activation of NF-κB. In addition, the activity of IL-18 can be modulated by the levels of the high-affinity, constitutively expressed, and circulating IL-18 binding protein (IL-18BP), which competes with cell surface receptors for IL-18 and neutralizes IL-18 activity. Variants of IL-18 (e.g., with amino acid mutations/deletions) that decrease interactions with IL-18BP and/or increase binding/signaling of the IL-18Rα/β complexes may be useful in enhancing IL-18 activity. Identification of such variants can be made through by standard screening assays (Kim et al. 2001, PNAS 98:3304-3309). Fragments of the IL-18 may exhibit biological activity. IL-18 variants could also be isolated that modify IL-18/IL-18R surface residence time, turnover and/or recycling. Such IL-18 variants could be incorporated into the fusion protein complex of the invention to optimize IL-18 activity and/or balance the combined cytokine activities to induce immune cell responses, particularly CIML NK cell activity. In addition, IL-18 variants could be incorporated into the fusion protein complex of the invention to optimize expression and/or stability of the IL-18 binding domain. Similarly, the IL-18 genes and expression constructs could be modified (i.e., codon optimization, removal of secondary structures) to improve gene expression, translation, post translational modification and/or secretion.

Antigen-Specific Binding Domains

Antigen-specific binding domains consist of polypeptides that specifically bind to targets on diseased cells. Alternatively, these domains may bind to targets on other cells that support the diseased state, such as targets on stromal cells that support tumor growth or targets on immune cells that support disease-mediated immunosuppression. Antigen-specific binding domains include antibodies, single chain antibodies, Fabs, Fv, T-cell receptor binding domains, ligand binding domains, receptor binding domains, domain antibodies, single domain antibodies, minibodies, nanobodies, peptibodies, or various other antibody mimics (such as affimers, affitins, alphabodies, atrimers, CTLA4-based molecules, adnectins, anticalins, Kunitz domain-based proteins, avimers, knottins, fynomers, darpins, affibodies, affilins, monobodies and armadillo repeat protein-based proteins (Weidle, U H, et al. 2013. Cancer Genomics & Proteomics 10: 155-168)) known in the art.

In certain embodiments, the antigen for the antigen-specific binding domain comprises a cell surface receptor or ligand. In a further embodiment, the antigen comprises a CD antigen, cytokine or chemokine receptor or ligand, growth factor receptor or ligand, tissue factor, cell adhesion molecule, MHC/MHC-like molecules, Fc receptor, Toll-like receptor, NK receptor, TCR, BCR, positive/negative co-stimulatory receptor or ligand, death receptor or ligand, tumor associated antigen, or virus encoded antigen.

Preferably, the antigen-specific binding domain is capable of binding to an antigen on a tumor cell. Tumor-specific binding domain may be derived from antibodies approved for treatment of patients with cancer include rituximab, ofatumumab, and obinutuzumab (anti-CD20 Abs); trastuzumab and pertuzumab (anti-HER2 Abs); cetuximab and panitumumab (anti-EGFR Abs); and alemtuzumab (anti-CD52 Ab). Similarly, binding domains from approved antibody-effector molecule conjugates specific to CD20 ($^{90}$Y-labeled ibritumomab tiuxetan, $^{131}$I-labeled tositumomab), HER2 (ado-trastuzumab emtansine), CD30 (brentuximab vedotin) and CD33 (gemtuzumab ozogamicin) (Sliwkowski M X, Mellman I. 2013 Science 341:1192) could be used.

Additionally, preferred binding domains of the invention may include various other tumor-specific antibody domains known in the art. The antibodies and their respective targets for treatment of cancer include but are not limited to nivolumab (anti-PD-1 Ab), TA99 (anti-gp75), 3F8 (anti-GD2), 8H9 (anti-B7-H3), abagovomab (anti-CA-125 (imitation)), adecatumumab (anti-EpCAM), afutuzumab (anti- CD20), alacizumab pegol (anti-VEGFR2), altumomab pentetate (anti-CEA), amatuximab (anti-mesothelin), AME-133 (anti-CD20), anatumomab mafenatox (anti-TAG-72), apolizumab (anti-HLA-DR), arcitumomab (anti-CEA), bavituximab (anti-phosphatidylserine), bectumomab (anti-CD22), belimumab (anti-BAFF), besilesomab (anti-CEA-related antigen), bevacizumab (anti-VEGF-A), bivatuzumab mertansine (anti-CD44 v6), blinatumomab (anti-CD19), BMS-663513 (anti-CD137), brentuximab vedotin (anti-CD30 (TNFRSF8)), cantuzumab mertansine (anti-mucin CanAg), cantuzumab ravtansine (anti-MUC1), capromab pendetide (anti-prostatic carcinoma cells), carlumab (anti-MCP-1), catumaxomab (anti-EpCAM, CD3), cBR96-doxo-rubicin immunoconjugate (anti-Lewis-Y antigen), CC49 (anti-TAG-72), cedelizumab (anti-CD4), Ch.14.18 (anti-GD2), ch-TNT (anti-DNA associated antigens), citatuzumab bogatox (anti-EpCAM), cixutumumab (anti-IGF-1 receptor), clivatuzumab tetraxetan (anti-MUC1), conatumumab (anti-TRAIL-R2), CP-870893 (anti-CD40), dacetuzumab (anti-CD40), daclizumab (anti-CD25), dalotuzumab (anti-insulin-like growth factor I receptor), daratumumab (anti-CD38 (cyclic ADP ribose hydrolase)), demcizumab (anti-DLL4), detumomab (anti-B-lymphoma cell), drozitumab (anti-DR5), duligotumab (anti-HER3), dusigitumab (anti-ILGF2), ecromeximab (anti-GD3 ganglioside), edrecolomab (anti-EpCAM), elotuzumab (anti-SLAMF7), elsilimomab (anti-IL-6), enavatuzumab (anti-TWEAK receptor), enoticumab (anti-DLL4), ensituximab (anti-5AC), epitumomab cituxetan (anti-episialin), epratuzumab (anti-CD22), ertumaxomab (anti-HER2/neu, CD3), etaracizumab (anti-integrin avP3), faralimomab (anti-Interferon receptor), farletuzumab (anti-folate receptor 1), FBTA05 (anti-CD20), ficlatuzumab (anti-HGF), figitumumab (anti-IGF-1 receptor), flanvotumab (anti-TYRP1(glycoprotein 75)), fresolimumab (anti-TGF β), futuximab (anti-EGFR), galiximab (anti-CD80), ganitumab (anti-IGF-I), gemtuzumab ozogamicin (anti-CD33), girentuximab (anti-carbonic anhydrase 9 (CA-IX)), glembatumumab vedotin (anti-GPNMB), guselkumab (anti-IL13), ibalizumab (anti-CD4), ibritumomab tiuxetan (anti-CD20), icrucumab (anti-VEGFR-1), igovomab (anti-CA-125), IMAB362 (anti-CLDN18.2), IMC-CS4 (anti-CSF1R), IMC-TR1 (TGFβRII), imgatuzumab (anti-EGFR), inclacumab (anti-selectin P), indatuximab ravtansine (anti-SDC1), inotuzumab ozogamicin (anti-CD22), intetumumab (anti-CD51), ipilimumab (anti-CD152), iratumumab (anti-CD30 (TNFRSF8)), KM3065 (anti-CD20), KW-0761 (anti-CD194), LY2875358 (anti-MET) labetuzumab (anti-CEA), lambrolizumab (anti-PDCD1), lexatumumab (anti-TRAIL-R2), lintuzumab (anti-CD33), lirilumab (anti-KIR2D), lorvotuzumab mertansine (anti-CD56), lucatumumab (anti-CD40), lumiliximab (anti-CD23 (IgE receptor)), mapatumumab (anti-TRAIL-R1), margetuximab (anti-ch4D5), matuzumab (anti-EGFR), mavrilimumab (anti-GMCSF receptor α-chain), milatuzumab (anti-CD74), minretumomab (anti-TAG-72), mitumomab (anti-GD3 ganglioside), mogamulizumab (anti-CCR4), moxetumomab pasudotox (anti-CD22), nacolomab tafenatox (anti-C242 antigen), naptumomab estafenatox (anti-5T4), narnatumab (anti-RON), necitumumab (anti-EGFR), nesvacumab (anti-angiopoietin 2), nimotuzumab (anti-EGFR), nivolumab (anti-IgG4), nofetumomab merpentan, ocrelizumab (anti-CD20), ocaratuzumab (anti-CD20), olaratumab (anti-PDGF-R α), onartuzumab (anti-c-MET), ontuxizumab (anti-TEM1), oportuzumab monatox (anti-EpCAM), oregovomab (anti-CA-125), otlertuzumab (anti-CD37), pankomab (anti-tumor specific glycosylation of MUC1), parsatuzumab (anti-EGFL7), pascolizumab (anti-IL-4), patritumab (anti-HER3), pemtumomab (anti-MUC1), pertuzumab (anti-HER2/neu), pidilizumab (anti-PD-1), pinatuzumab vedotin (anti-CD22), pintumomab (anti-adenocarcinoma antigen), polatuzumab vedotin (anti-CD79B), pritumumab (anti-vimentin), PRO131921 (anti-CD20), quilizumab (anti-IGHE), racotumomab (anti-N-glycolylneuraminic acid), radretumab (anti-fibronectin extra domain-B), ramucirumab (anti-VEGFR2), rilotumumab (anti-HGF), robatumumab (anti-IGF-1 receptor), roledumab (anti-RHD), rovelizumab (anti-CD11 & CD18), samalizumab (anti-CD200), satumomab pendetide (anti-TAG-72), seribantumab (anti-ERBB3), SGN-CD19A (anti-CD19), SGN-CD33A (anti-CD33), sibrotuzumab (anti-FAP), siltuximab (anti-IL-6), solitomab (anti-EpCAM), sontuzumab (anti-episialin), tabalumab (anti-BAFF), tacatuzumab tetraxetan (anti-alpha-fetoprotein), taplitumomab paptox (anti-CD19), telimomab aritox, tenatumomab (anti-tenascin C), teneliximab (anti-CD40), teprotumumab (anti-CD221), TGN1412 (anti-CD28), ticilimumab (anti-CTLA-4), tigatuzumab (anti-TRAIL-R2), TNX-650 (anti-IL-13), tositumomab (anti-CS20), tovetumab (anti-CD140a), TRBS07 (anti-GD2), tregalizumab (anti-CD4), tremelimumab (anti-CTLA-4), TRU-016 (anti-CD37), tucotuzumab celmoleukin (anti-EpCAM), ublituximab (anti-CD20), urelumab (anti-4-1BB), vanticumab (anti-Frizzled receptor), vapaliximab (anti-AOC3 (VAP-1)), vatelizumab (anti-ITGA2), veltuzumab (anti-CD20), vesencumab (anti-NRP1), visilizumab (anti-CD3), volociximab (anti-integrin α5β1), vorsetuzumab mafodotin (anti-CD70), votumumab (anti-tumor antigen CTAA16.88), zalutumumab (anti-EGFR), zanolimumab (anti-CD4), zatuximab (anti-HER1), ziralimumab (anti-CD147 (basigin)), RG7636 (anti-ETBR), RG7458 (anti-MUC16), RG7599 (anti-NaPi2b), MPDL3280A (anti-PD-L1), RG7450 (anti-STEAP1), and GDC-0199 (anti-Bcl-2).

Other antibody domains or tumor target binding proteins useful in the invention (e.g. TCR domains) include, but are not limited to, those that bind the following antigens (note, the cancer indications indicated represent non-limiting examples): aminopeptidase N (CD13), annexin A1, B7-H3 (CD276, various cancers), CA125 (ovarian cancers), CA15-3 (carcinomas), CA19-9 (carcinomas), L6 (carcinomas), Lewis Y (carcinomas), Lewis X (carcinomas), alpha fetoprotein (carcinomas), CA242 (colorectal cancers), placental alkaline phosphatase (carcinomas), prostate specific antigen (prostate), prostatic acid phosphatase (prostate), epidermal growth factor (carcinomas), CD2 (Hodgkin's disease, NHL lymphoma, multiple myeloma), CD3 epsilon (T cell lymphoma, lung, breast, gastric, ovarian cancers, autoimmune diseases, malignant ascites), CD19 (B cell malignancies), CD20 (non-Hodgkin's lymphoma, B-cell neoplasms, autoimmune diseases), CD21 (B-cell lymphoma), CD22 (leukemia, lymphoma, multiple myeloma, SLE), CD30 (Hodgkin's lymphoma), CD33 (leukemia, autoimmune diseases), CD38 (multiple myeloma), CD40 (lymphoma, multiple myeloma, leukemia (CLL)), CD51 (metastatic melanoma, sarcoma), CD52 (leukemia), CD56 (small cell lung cancers, ovarian cancer, Merkel cell carcinoma, and the liquid tumor, multiple myeloma), CD66e (carcinomas), CD70 (metastatic renal cell carcinoma and non-Hodgkin lymphoma), CD74 (multiple myeloma), CD80 (lymphoma), CD98 (carcinomas), CD123 (leukemia), mucin (carcinomas), CD221 (solid tumors), CD227 (breast, ovarian cancers), CD262 (NSCLC and other cancers), CD309 (ovarian cancers), CD326 (solid tumors), CEACAM3 (colorectal, gastric cancers), CEACAM5 (CEA, CD66e) (breast, colorectal and lung cancers), DLL4 (A-like- 4), EGFR (various cancers), CTLA4 (melanoma), CXCR4 (CD 184, heme-oncology, solid tumors), Endoglin (CD 105, solid tumors), EPCAM (epithelial cell adhesion molecule, bladder, head, neck, colon, NHL prostate, and ovarian cancers), ERBB2 (lung, breast, prostate cancers), FCGR1 (autoimmune diseases), FOLR (folate receptor, ovarian cancers), FGFR (carcinomas), GD2 ganglioside (carcinomas), G-28 (a cell surface antigen glycolipid, melanoma), GD3 idiotype (carcinomas), heat shock proteins (carcinomas), HER1 (lung, stomach cancers), HER2 (breast, lung and ovarian cancers), HLA-DR10 (NHL), HLA-DRB (NHL, B cell leukemia), human chorionic gonadotropin (carcinomas), IGF1R (solid tumors, blood cancers), IL-2 receptor (T-cell leukemia and lymphomas), IL-6R (multiple myeloma, RA, Castleman's disease, IL6 dependent tumors), integrins ($\alpha v\beta 3$, $\alpha 5\beta 1$, $\alpha 6\beta 4$, $\alpha 11\beta 3$, $\alpha 5\beta 5$, $\alpha v\beta 5$, for various cancers), MAGE-1 (carcinomas), MAGE-2 (carcinomas), MAGE-3 (carcinomas), MAGE 4 (carcinomas), anti-transferrin receptor (carcinomas), p97 (melanoma), MS4A1 (membrane-spanning 4-domains subfamily A member 1, Non-Hodgkin's B cell lymphoma, leukemia), MUC1 (breast, ovarian, cervix, bronchus and gastrointestinal cancer), MUC16 (CA125) (ovarian cancers), CEA (colorectal cancer), gp100 (melanoma), MARTI (melanoma), MPG (melanoma), MS4A1 (membrane-spanning 4-domains subfamily A, small cell lung cancers, NHL), nucleolin, Neu oncogene product (carcinomas), P21 (carcinomas), nectin-4 (carcinomas), paratope of anti-(N-glycolylneuraminic acid, breast, melanoma cancers), PLAP-like testicular alkaline phosphatase (ovarian, testicular cancers), PSMA (prostate tumors), PSA (prostate), ROB04, TAG 72 (tumour associated glycoprotein 72, AML, gastric, colorectal, ovarian cancers), T cell transmembrane protein (cancers), Tie (CD202b), tissue factor, TNFRSF10B (tumor necrosis factor receptor superfamily member 10B, carcinomas), TNFRSF13B (tumor necrosis factor receptor superfamily member 13B, multiple myeloma, NHL, other cancers, RA and SLE), TPBG (trophoblast glycoprotein, renal cell carcinoma), TRAIL-R1 (tumor necrosis apoptosis inducing ligand receptor 1, lymphoma, NHL, colorectal, lung cancers), VCAM-1 (CD106, Melanoma), VEGF, VEGF-A, VEGF-2 (CD309) (various cancers). Some other tumor associated antigen targets have been reviewed (Gerber, et al, mAbs 2009 1:247-253; Novellino et al, Cancer Immunol Immunother. 2005 54:187-207, Franke, et al, Cancer Biother Radiopharm. 2000, 15:459-76, Guo, et al., Adv Cancer Res. 2013; 119: 421-475, Parmiani et al. J Immunol. 2007 178: 1975-9). Examples of these antigens include Cluster of Differentiations (CD4, CD5, CD6, CD7, CD8, CD9, CD10, CD11a, CD11b, CD11c, CD12w, CD14, CD15, CD16, CDw17, CD18, CD21, CD23, CD24, CD25, CD26, CD27, CD28, CD29, CD31, CD32, CD34, CD35, CD36, CD37, CD41, CD42, CD43, CD44, CD45, CD46, CD47, CD48, CD49b, CD49c, CD53, CD54, CD55, CD58, CD59, CD61, CD62E, CD62L, CD62P, CD63, CD68, CD69, CD71, CD72, CD79, CD81, CD82, CD83, CD86, CD87, CD88, CD89, CD90, CD91, CD95, CD96, CD100, CD103, CD105, CD106, CD109, CD117, CD120, CD127, CD133, CD134, CD135, CD138, CD141, CD142, CD143, CD144, CD147, CD151, CD152, CD154, CD156, CD158, CD163, CD166, CD168, CD184, CDw186, CD195, CD202 (a, b), CD209, CD235a, CD271, CD303, CD304), annexin A1, nucleolin, endoglin (CD105), ROB04, amino-peptidase N, -like-4 (DLL4), VEGFR-2 (CD309), CXCR4 (CD184), Tie2, B7-H3, WT1, MUC1, LMP2, HPV E6 E7, EGFRvIII, HER-2/neu, idiotype, MAGE A3, p53 nonmutant, NY-ESO-1, GD2, CEA, MelanAIMART1, Ras mutant, gp100, p53 mutant, proteinase3 (PR1), bcr-abl, tyrosinase, survivin, hTERT, sarcoma translocation breakpoints, EphA2, PAP, ML-IAP, AFP, EpCAM, ERG (TMPRSS2 ETS fusion gene), NA17, PAX3, ALK, androgen receptor, cyclin B 1, polysialic acid, MYCN, RhoC, TRP-2, GD3, fucosyl GMl, mesothelin, PSCA, MAGE A1, sLe(a), CYPIB I, PLACl, GM3, BORIS, Tn, GloboH, ETV6-AML, NY-BR-1, RGS5, SART3, STn, carbonic anhydrase IX, PAX5, OY-TES1, sperm protein 17, LCK, HMWMAA, AKAP-4, SSX2, XAGE 1, B7H3, legumain, Tie 2, Page 4, VEGFR2, MAD-CT-1, FAP, PDGFR-$\beta$, MAD-CT-2, and Fos-related antigen 1.

Additionally, preferred binding domains of the invention include those specific to antigens and epitope targets associated with infected cells that are known in the art. Such targets include but are not limited those derived from the following infectious agents are of interest: HIV virus (particularly antigens derived from the HIV envelope spike and/or gp120 and gp41 epitopes), Human papilloma virus (HPV), *Mycobacterium tuberculosis, Streptococcus agalactiae*, methicillin-resistant *Staphylococcus aureus, Legionella pneumophilia, Streptococcus pyogenes, Escherichia coli, Neisseria gonorrhoeae, Neisseria meningitidis, Pneumococcus, Cryptococcus neoformans, Histoplasma capsulatum, —influenzae* B, *Treponema pallidum*, Lyme disease spirochetes, *Pseudomonas aeruginosa, Mycobacterium leprae, Brucella abortus*, rabies virus, influenza virus, cytomegalovirus, herpes simplex virus I, herpes simplex virus II, human serum parvo-like virus, respiratory syncytial virus, varicella-zoster virus, hepatitis B virus, hepatitis C virus, measles virus, adenovirus, human T-cell leukemia viruses, Epstein-Barr virus, murine leukemia virus, mumps virus, vesicular stomatitis virus, sindbis virus, lymphocytic choriomeningitis virus, wart virus, blue tongue virus, Sendai virus, feline leukemia virus, reovirus, polio virus, simian virus 40, mouse mammary tumor virus, dengue virus, rubella virus, West Nile virus, *Plasmodium falciparum, Plasmodium vivax, Toxoplasma gondii, Trypanosoma rangeli, Trypanosoma cruzi, Trypanosoma rhodesiensei, Trypanosoma brucei, Schistosoma mansoni, Schistosoma japonicum, Babesia bovis, Elmeria tenella, Onchocerca volvulus, Leishmania tropica, Trichinella spiralis, Theileria parva, Taenia hydatigena, Taenia ovis, Taenia saginata, Echinococcus granulosus, Mesocestoides corti, Mycoplasma arthritidis, M. hyorhinis, M. orale, M arginini, Acholeplasma laidlawii, M. salivarium* and *M. pneumoniae.*

Immune Checkpoint Inhibitor and Immune Agonist Domains

In other embodiments, the binding domain is specific to an immune checkpoint or signaling molecule or its ligand and acts as an inhibitor of immune checkpoint suppressive activity or as an agonist of immune stimulatory activity. Such immune checkpoint and signaling molecules and ligands include PD-1, PD-L1, PD-L2, CTLA-4, CD28, CD80, CD86, B7-H3, B7-H4, B7-H5, ICOS-L, ICOS, BTLA, CD137L, CD137, HVEM, KIR, 4-1BB, OX40L, CD70, CD27, CD47, CIS, OX40, GITR, IDO, TIM3, GAL9, VISTA, CD155, TIGIT, LIGHT, LAIR-1, Siglecs and A2aR (Pardoll D M. 2012. Nature Rev Cancer 12:252-264, Thaventhiran T, et al. 2012. J Clin Cell Immunol S12:004). Additionally, preferred antibody domains of the invention may include ipilimumab and/or tremelimumab (anti-CTLA4), nivolumab, pembrolizumab, pidilizumab, TSR-042, ANB011, AMP-514 and AMP-224 (a ligand-Fc fusion) (anti-PD1), atezolizumab (MPDL3280A), avelumab (MSB0010718C), durvalumab (MEDI4736), MEDI0680, and BMS-9365569 (anti-PDL1), MEDI6469 (anti-OX40 agonist), BMS-986016, IMP701, IMP731, IMP321 (anti-LAG3) and GITR ligand.

T-Cell Receptors (TCRs)

T-cells are a subgroup of cells which together with other immune cell types (polymorphonuclear cells, eosinophils, basophils, mast cells, B-cells, NK cells), constitute the cellular component of the immune system. Under physiological conditions, T-cells function in immune surveillance and in the elimination of foreign antigen. However, under pathological conditions, there is compelling evidence that T-cells play a major role in the causation and propagation of disease. In these disorders, breakdown of T-cell immunological tolerance, either central or peripheral is a fundamental process in the causation of autoimmune disease.

The TCR complex is composed of at least seven transmembrane proteins. The disulfide-linked ($\alpha\beta$ or $\gamma\delta$) heterodimer forms the monotypic antigen recognition unit, while the invariant chains of CD3, consisting of $\epsilon$, $\gamma$, $\delta$, $\zeta$, and $\eta$ chains, are responsible for coupling the ligand binding to signaling pathways that result in T-cell activation and the elaboration of the cellular immune responses. Despite the gene diversity of the TCR chains, two structural features are common to all known subunits. First, they are transmembrane proteins with a single transmembrane spanning domain—presumably alpha-helical. Second, all TCR chains have the unusual feature of possessing a charged amino acid within the predicted transmembrane domain. The invariant chains have a single negative charge, conserved between the mouse and human, and the variant chains possess one (TCR-$\beta$) or two (TCR-$\alpha$) positive charges. The transmembrane sequence of TCR-$\alpha$ is highly conserved in a number of species and thus phylogenetically may serve an important functional role. The octapeptide sequence containing the hydrophilic amino acids arginine and lysine is identical between the species.

A T-cell response is modulated by antigen binding to a TCR. One type of TCR is a membrane bound heterodimer consisting of an $\alpha$ and $\beta$ chain resembling an immunoglobulin variable (V) and constant (C) region. The TCR $\alpha$ chain includes a covalently linked V-$\alpha$ and C-$\alpha$ chain, whereas the $\beta$ chain includes a V-$\beta$ chain covalently linked to a C-$\beta$ chain. The V-$\alpha$ and V-$\beta$ chains form a pocket or cleft that can bind a superantigen or antigen in the context of a major histocompatibility complex (MHC) (known in humans as an HLA complex). See, Davis Ann. Rev. of Immunology 3: 537 (1985); Fundamental Immunology 3rd Ed., W. Paul Ed. Rsen Press LTD. New York (1993).

The extracellular domains of the TCR chains ($\alpha\beta$ or $\gamma\delta$) can also engineered as fusions to heterologous transmembrane domains for expression on the cell surface. Such TCRs may include fusions to CD3, CD28, CD8, 4-1BB and/or chimeric activation receptor (CAR) transmembrane or activation domains. TCRs can also be the soluble proteins comprising one or more of the antigen binding domains of $\alpha\beta$ or $\gamma\delta$ chains. Such TCRs may include the TCR variable domains or function fragments thereof with or without the TCR constant domains. Soluble TCRs may be heterodimeric or single-chain molecules.

Fc Domain

Fusion protein complexes of the invention may contain an Fc domain. For example, hIL-18/IL12/TxM comprises an IL-18/IL-15N72D:IL-12/IL-15R$\alpha$Su/Fc fusion protein complex. Fusion proteins that combine the Fc regions of IgG with the domains of another protein, such as various cytokines and soluble receptors have been reported (see, for example, Capon et al., Nature, 337:525-531, 1989; Chamow et al., Trends Biotechnol., 14:52-60, 1996); U.S. Pat. Nos. 5,116,964 and 5,541,087). The prototype fusion protein is a homodimeric protein linked through cysteine residues in the hinge region of IgG Fc, resulting in a molecule similar to an IgG molecule without the heavy chain variable and $C_H1$ domains and light chains. The dimeric nature of fusion proteins comprising the Fc domain may be advantageous in providing higher order interactions (i.e. bivalent or bispecific binding) with other molecules. Due to the structural homology, Fc fusion proteins exhibit an in vivo pharmacokinetic profile comparable to that of human IgG with a similar isotype. Immunoglobulins of the IgG class are among the most abundant proteins in human blood, and their circulation half-lives can reach as long as 21 days. To extend the circulating half-life of IL-15 or an IL-15 fusion protein and/or to increase its biological activity, fusion protein complexes containing the IL-15 domain non-covalently bound to IL-15R$\alpha$ covalently linked to the Fc portion of the human heavy chain IgG protein are described herein.

The term "Fc" refers to the fragment crystallizable region which is the constant region of an antibody that interacts with cell surface receptors called Fc receptors and some proteins of the complement system. Such an "Fc" is in dimeric form. The original immunoglobulin source of the native Fc is preferably of human origin and may be any of the immunoglobulins, although IgG1 and IgG2 are preferred. Native Fc's are made up of monomeric polypeptides that may be linked into dimeric or multimeric forms by covalent (i.e., disulfide bonds) and non-covalent association. The number of intermolecular disulfide bonds between monomeric subunits of native Fc molecules ranges from 1 to 4 depending on class (e.g., IgG, IgA, IgE) or subclass (e.g., IgG1, IgG2, IgG3, IgA1, IgA2). One example of a native Fc is a disulfide-bonded dimer resulting from papain digestion of an IgG (see Ellison et al. (1982), Nucleic Acids Res. 10: 4071-9). The term "native Fc" as used herein is generic to the monomeric, dimeric, and multimeric forms. Fc domains containing binding sites for Protein A, Protein G, various Fc receptors and complement proteins. In some embodiments, Fc domain of the fusion protein complex is capable of interacting with Fc receptors to mediate antibody-dependent cell-mediated cytotoxicity (ADCC) and/or antibody dependent cellular phagocytosis (ADCP). In other applications, the fusion protein complex comprises an Fc domain (e.g., IgG4 Fc) that is incapable of effectively mediating ADCC or ADCP.

In some embodiments, the term "Fc variant" refers to a molecule or sequence that is modified from a native Fc, but still comprises a binding site for the salvage receptor, FcRn. International applications WO 97/34631 and WO 96/32478 describe exemplary Fc variants, as well as interaction with the salvage receptor, and are hereby incorporated by reference. Thus, the term "Fc variant" comprises a molecule or sequence that is humanized from a non-human native Fc. Furthermore, a native Fc comprises sites that may be removed because they provide structural features or biological activity that are not required for the fusion molecules of the present invention. Thus, in certain embodiments, the term "Fc variant" comprises a molecule or sequence that alters one or more native Fc sites or residues that affect or are involved in (1) disulfide bond formation, (2) incompatibility with a selected host cell (3) N-terminal heterogeneity upon expression in a selected host cell, (4) glycosylation, (5) interaction with complement, (6) binding to an Fc receptor other than a salvage receptor, (7) antibody-dependent cellular cytotoxicity (ADCC) or (8) antibody-dependent cellular phagocytosis (ADCP). Such alterations can increase or decrease any one or more of these Fc properties. Fc variants are described in further detail hereinafter.

The term "Fc domain" encompasses native Fc and Fc variant molecules and sequences as defined above. As with Fc variants and native Fc's, the term "Fe domain" includes molecules in monomeric or multimeric form, whether digested from whole antibody or produced by recombinant gene expression or by other means.

Linkers

In some cases, the fusion protein complexes of the invention also include a flexible linker sequence interposed between the IL-15 or IL-15Rα domains and the IL-12 and/or IL-18 binding domain or the IL-12 subunits. The linker sequence should allow effective positioning of the polypeptide with respect to the IL-15 or IL-15Rα domains to allow functional activity of both domains. Alternatively, the linker should allow formation of a functional IL-12 binding domain.

In certain cases, the soluble fusion protein complex has a linker wherein the first polypeptide is covalently linked to IL-15 (or functional fragment thereof) by polypeptide linker sequence. In other aspects, the soluble fusion protein complex as described herein has a linker wherein the second polypeptide is covalently linked to IL-15Rα polypeptide (or functional fragment thereof) by polypeptide linker sequence.

The linker sequence is preferably encoded by a nucleotide sequence resulting in a peptide that can effectively position the binding groove of a TCR molecule for recognition of a presenting antigen or the binding domain of an antibody molecule for recognition of an antigen. As used herein, the phrase "effective positioning of the biologically active polypeptide with respect to the IL-15 or IL-15Rα domains", or other similar phrase, is intended to mean the biologically active polypeptide linked to the IL-15 or IL-15Rα domains is positioned so that the IL-15 or IL-15Rα domains are capable of interacting with each other to form a protein complex. For example, the IL-15 or IL-15Rα domains are effectively positioned to allow interactions with immune cells to initiate or inhibit an immune reaction, or to inhibit or stimulate cell development.

The fusion protein complexes of the invention preferably also include a flexible linker sequence interposed between the IL-15 or IL-15Rα domains and the immunoglobulin Fc domain. The linker sequence should allow effective positioning of the Fc domain, biologically active polypeptide and IL-15 or IL-15Rα domains to allow functional activity of each domain. For example, the Fc domains are effectively positioned to allow proper fusion protein complex formation and/or interactions with Fc receptors on immune cells or proteins of the complement system to stimulate Fc-mediated effects including opsonization, cell lysis, degranulation of mast cells, basophils, and eosinophils, and other Fc receptor-dependent processes; activation of the complement pathway; and enhanced in vivo half-life of the fusion protein complex.

Linker sequences can also be used to link two or more polypeptides of the biologically active polypeptide to generate a single-chain molecule with the desired functional activity.

Preferably, the linker sequence comprises from about 7 to 20 amino acids, more preferably from about 10 to 20 amino acids. The linker sequence is preferably flexible so as not hold the biologically active polypeptide or effector molecule in a single undesired conformation. The linker sequence can be used, e.g., to space the recognition site from the fused molecule. Specifically, the peptide linker sequence can be positioned between the biologically active polypeptide and the effector molecule, e.g., to chemically cross-link same and to provide molecular flexibility. The linker preferably predominantly comprises amino acids with small side chains, such as glycine, alanine and serine, to provide for flexibility. Preferably, about 80 or 90 percent or greater of the linker sequence comprises glycine, alanine or serine residues, particularly glycine and serine residues.

Different linker sequences could be used including any of a number of flexible linker designs that have been used successfully to join antibody variable regions together (see, Whitlow, M. et al., (1991) Methods: A Companion to Methods in Enzymology, 2:97-105).

Adoptive Cell Therapy

Adoptive cell therapy (ACT) (including allogeneic and autologous hematopoietic stem cell transplantation (HSCT) and recombinant cell (i.e., CAR T) therapies) is the treatment of choice for many malignant disorders (for reviews of HSCT and adoptive cell therapy approaches, see, Rager & Porter, Ther Adv Hematol (2011) 2(6) 409-428; Roddie & Peggs, Expert Opin. Biol. Ther. (2011) 11(4):473-487; Wang et al. Int. J. Cancer: (2015) 136, 1751-1768; and Chang, Y. J. and X. J. Huang, Blood Rev, 2013. 27(1): 55-62). Such adoptive cell therapies include, but are not limited to, allogeneic and autologous hematopoietic stem cell transplantation, donor leukocyte (or lymphocyte) infusion (DLI), adoptive transfer of tumor infiltrating lymphocytes, or adoptive transfer of T cells or NK cells (including recombinant cells, i.e., CAR T, CAR NK, gene-edited T cells or NK cells, see Hu et al. Acta Pharmacologica Sinica (2018) 39: 167-176, Irving et al. Front Immunol. (2017) 8: 267). Beyond the necessity for donor-derived cells to reconstitute hematopoiesis after radiation and chemotherapy, immunologic reconstitution from transferred cells is important for the elimination of residual tumor cells. The efficacy of ACT as a curative option for malignancies is influenced by a number of factors including the origin, composition and phenotype (lymphocyte subset, activation status) of the donor cells, the underlying disease, the pre-transplant conditioning regimen and post-transplant immune support (i.e., IL-2 therapy) and the graft-versus-tumor (GVT) effect mediated by donor cells within the graft. Additionally, these factors must be balanced against transplant-related mortality, typically arising from the conditioning regimen and/or excessive immune activity of donor cells within the host (i.e., graft-versus-host disease, cytokine release syndrome, etc.).

Approaches utilizing adoptive NK cell therapy have become of significant interest. In patients receiving autologous HSCT, blood NK cell numbers recover very early after the transplant and the levels of NK cells correlate with a positive outcome (Rueff et al., 2014, Biol. Blood Marrow Transplant. 20, 896-899). Although therapeutic strategies with autologous NK cell transfer have had limited success due to a number of factors, adoptive transfer of ex vivo-activated allogeneic (or haplo-identical) NK cells has emerged as a promising immunotherapeutic strategy for cancer (Guillerey et al. 2016. Nature Immunol. 17: 1025-1036). The activity of these cells is less likely to be suppressed by self-MHC molecules compared to autologous NK cells. A number of studies have shown that adoptive therapy with haploidentical NK cells to exploit alloreactivity against tumor cells is safe and can mediate significant clinical activity in AML patients. Taking these findings further, recent studies have focused on optimizing ex vivo activation/expansion methods for NK cells or NK precursors (i.e., stem cells) and pre-transplant conditioning and post-transplant immune support strategies; use of NK cell lines or recombinant tumor-targeting NK cells; evaluation of combination therapies with other agents such as therapeutic Ab, immunomodulatory agents (lenalidomide), and anti-KIR and checkpoint Abs. In each case, these strategies could be complemented by the fusion protein complex of the invention, which has the capacity to augment NK cell proliferation and activation. As indicated herein, ex vivo incubation of NK cells with the fusion protein complex of the invention result in induction of CIML NK cell exhibiting elevated activation markers, increased cytotoxicity against tumor cells and enhanced production of IFN-γ. Additionally, the fusion protein complex of the invention is capable of activating human NK cell lines. Moreover, methods are provided for augmenting immune responses and treating neoplasia and infection disease by direct administration of the fusion protein complex of the invention or administration of immune cells activated by the fusion protein complex of the invention.

Pharmaceutical Therapeutics

The invention provides pharmaceutical compositions comprising fusion protein complexes for use as a therapeutic. In one aspect, fusion protein complex of the invention is administered systemically, for example, formulated in a pharmaceutically-acceptable buffer such as physiological saline. Preferable routes of administration include, for example, instillation into the bladder, subcutaneous, intravenous, intraperitoneal, intramuscular, intratumoral or intradermal injections that provide continuous, sustained or effective levels of the composition in the patient. Treatment of human patients or other animals is carried out using a therapeutically effective amount of a therapeutic identified herein in a physiologically-acceptable carrier. Suitable carriers and their formulation are described, for example, in Remington's Pharmaceutical Sciences by E. W. Martin. The amount of the therapeutic agent to be administered varies depending upon the manner of administration, the age and body weight of the patient, and with the clinical symptoms of the neoplasia. Generally, amounts will be in the range of those used for other agents used in the treatment of other diseases associated with neoplasia or infectious diseases, although in certain instances lower amounts will be needed because of the increased specificity of the compound. A compound is administered at a dosage that enhances an immune response of a subject, or that reduces the proliferation, survival, or invasiveness of a neoplastic or, infected cell as determined by a method known to one skilled in the art.

Formulation of Pharmaceutical Compositions

The administration of the fusion protein complex of the invention for the treatment of a neoplasia or infectious disease is by any suitable means that results in a concentration of the therapeutic that, combined with other components, is effective in ameliorating, reducing, or stabilizing said neoplasia or infectious disease. The fusion protein complex of the invention may be contained in any appropriate amount in any suitable carrier substance, and is generally present in an amount of 1-95% by weight of the total weight of the composition. The composition may be provided in a dosage form that is suitable for parenteral (e.g., subcutaneous, intravenous, intramuscular, intravesicular, intratumoral or intraperitoneal) administration route. For example, the pharmaceutical compositions are formulated according to conventional pharmaceutical practice (see, e.g., Remington: The Science and Practice of Pharmacy (20th ed.), ed. A. R. Gennaro, Lippincott Williams & Wilkins, 2000 and Encyclopedia of Pharmaceutical Technology, eds. J. Swarbrick and J. C. Boylan, 1988-1999, Marcel Dekker, New York).

Human dosage amounts are initially determined by extrapolating from the amount of compound used in mice or non-human primates, as a skilled artisan recognizes it is routine in the art to modify the dosage for humans compared to animal models. For example, the dosage may vary from between about 1 μg compound/kg body weight to about 5000 mg compound/kg body weight; or from about 5 mg/kg body weight to about 4,000 mg/kg body weight or from about 10 mg/kg body weight to about 3,000 mg/kg body weight; or from about 50 mg/kg body weight to about 2000 mg/kg body weight; or from about 100 mg/kg body weight to about 1000 mg/kg body weight; or from about 150 mg/kg body weight to about 500 mg/kg body weight. For example, the dose is about 1, 5, 10, 25, 50, 75, 100, 150, 200, 250, 300, 350, 400, 450, 500, 550, 600, 650, 700, 750, 800, 850, 900, 950, 1,000, 1,050, 1,100, 1,150, 1,200, 1,250, 1,300, 1,350, 1,400, 1,450, 1,500, 1,600, 1,700, 1,800, 1,900, 2,000, 2,500, 3,000, 3,500, 4,000, 4,500, or 5,000 mg/kg body weight. Alternatively, doses are in the range of about 5 mg compound/Kg body weight to about 20 mg compound/kg body weight. In another example, the doses are about 8, 10, 12, 14, 16 or 18 mg/kg body weight. Preferably, the fusion protein complex is administered at 0.5 mg/kg-about 10 mg/kg (e.g., 0.5, 1, 3, 5, 10 mg/kg). Of course, this dosage amount may be adjusted upward or downward, as is routinely done in such treatment protocols, depending on the results of the initial clinical trials and the needs of a particular patient.

Pharmaceutical compositions are formulated with appropriate excipients into a pharmaceutical composition that, upon administration, releases the therapeutic in a controlled manner. Examples include single or multiple unit tablet or capsule compositions, oil solutions, suspensions, emulsions, microcapsules, microspheres, molecular complexes, nanoparticles, patches, and liposomes. Preferably, the fusion protein complex is formulated in an excipient suitable for parenteral administration.

Parenteral Compositions

The pharmaceutical composition comprising a fusion protein complex of the invention are administered parenterally by injection, infusion or implantation (subcutaneous, intravenous, intramuscular, intratumoral, intravesicular, intraperitoneal) in dosage forms, formulations, or via suitable delivery devices or implants containing conventional, non-toxic pharmaceutically acceptable carriers and adjuvants. The formulation and preparation of such compositions are well known to those skilled in the art of pharmaceutical formulation. Formulations can be found in Remington: The Science and Practice of Pharmacy, supra.

Compositions comprising a fusion protein complex of the invention for parenteral use are provided in unit dosage forms (e.g., in single-dose ampoules). Alternatively, the composition is provided in vials containing several doses and in which a suitable preservative may be added (see below). The composition is in the form of a solution, a suspension, an emulsion, an infusion device, or a delivery device for implantation, or is presented as a dry powder to be reconstituted with water or another suitable vehicle before use. Apart from the active agent that reduces or ameliorates a neoplasia or infectious disease, the composition includes suitable parenterally acceptable carriers and/or excipients. The active therapeutic agent(s) may be incorporated into microspheres, microcapsules, nanoparticles, liposomes for controlled release. Furthermore, the composition may include suspending, solubilizing, stabilizing, pH-adjusting agents, tonicity adjusting agents, and/or dispersing, agents.

As indicated above, the pharmaceutical compositions comprising a fusion protein complex of the invention may be in a form suitable for sterile injection. To prepare such a composition, the suitable active therapeutic(s) are dissolved or suspended in a parenterally acceptable liquid vehicle. Among acceptable vehicles and solvents that may be employed are water, water adjusted to a suitable pH by addition of an appropriate amount of hydrochloric acid, sodium hydroxide or a suitable buffer, 1,3-butanediol, Ringer's solution, and isotonic sodium chloride solution and dextrose solution. The aqueous formulation may also contain one or more preservatives (e.g., methyl, ethyl or n-propyl p-hydroxybenzoate). In cases where one of the compounds is only sparingly or slightly soluble in water, a dissolution enhancing or solubilizing agent can be added, or the solvent may include 10-60% w/w of propylene glycol.

The present invention provides methods of treating neoplasia or infectious diseases or symptoms thereof which comprise administering a therapeutically effective amount of a pharmaceutical composition comprising a compound of the formulae herein to a subject (e.g., a mammal such as a human). Thus, one embodiment is a method of treating a subject suffering from or susceptible to a neoplasia or infectious disease or symptom thereof. The method includes the step of administering to the mammal a therapeutic amount of an amount of a compound herein sufficient to treat the disease or disorder or symptom thereof, under conditions such that the disease or disorder is treated.

The methods herein include administering to the subject (including a subject identified as in need of such treatment) an effective amount of a compound described herein, or a composition described herein to produce such effect. Identifying a subject in need of such treatment can be in the judgment of a subject or a health care professional and can be subjective (e.g. opinion) or objective (e.g. measurable by a test or diagnostic method).

The therapeutic methods of the invention (which include prophylactic treatment) in general comprise administration of a therapeutically effective amount of the compounds herein, such as a compound of the formulae herein to a subject (e.g., animal, human) in need thereof, including a mammal, particularly a human. Such treatment will be suitably administered to subjects, particularly humans, suffering from, having, susceptible to, or at risk for a neoplasia, infectious disease, disorder, or symptom thereof. Determination of those subjects "at risk" can be made by any objective or subjective determination by a diagnostic test or opinion of a subject or health care provider (e.g., genetic test, enzyme or protein marker, Marker (as defined herein), family history, and the like). The fusion protein complexes of the invention may be used in the treatment of any other disorders in which an increase in an immune response is desired.

The invention also provides a method of monitoring treatment progress. The method includes the step of determining a level of diagnostic marker (Marker) (e.g., any target delineated herein modulated by a compound herein, a protein or indicator thereof, etc.) or diagnostic measurement (e.g., screen, assay) in a subject suffering from or susceptible to a disorder or symptoms thereof associated with neoplasia in which the subject has been administered a therapeutic amount of a compound herein sufficient to treat the disease or symptoms thereof. The level of Marker determined in the method can be compared to known levels of Marker in either healthy normal controls or in other afflicted patients to establish the subject's disease status. In some cases, a second level of Marker in the subject is determined at a time point later than the determination of the first level, and the two levels are compared to monitor the course of disease or the efficacy of the therapy. In certain aspects, a pre-treatment level of Marker in the subject is determined prior to beginning treatment according to this invention; this pre-treatment level of Marker can then be compared to the level of Marker in the subject after the treatment commences, to determine the efficacy of the treatment.

Combination Therapies

Optionally, the fusion protein complex of the invention or immune cells treated with the fusion protein complex of the invention are administered in combination with any other standard therapy; such methods are known to the skilled artisan and described in Remington's Pharmaceutical Sciences by E. W. Martin. If desired, the fusion protein complex of the invention or immune cells treated with the fusion protein complex of the invention are administered in combination with any conventional anti-neoplastic therapy, including but not limited to, immunotherapy, adoptive cell therapy, vaccines, therapeutic and checkpoint inhibitor antibodies, targeted therapy, surgery, radiation therapy, or chemotherapy.

Kits or Pharmaceutical Systems

Pharmaceutical compositions comprising the fusion protein complex of the invention or immune cells treated with the fusion protein complex of the invention may be assembled into kits or pharmaceutical systems for use in ameliorating a neoplasia or infectious disease. Kits or pharmaceutical systems according to this aspect of the invention comprise a carrier means, such as a box, carton, tube, having in close confinement therein one or more container means, such as vials, tubes, ampoules, bottles and the like. The kits or pharmaceutical systems of the invention may also comprise associated instructions for using the fusion protein complex of the invention. In one embodiment, the kit includes appropriate containers such as bags, bottles, tubes, to allow ex vivo treatment of immune cells using the fusion protein complex of the invention and/or administration of such cells to a patient. Kits may also include medical devices comprising the fusion protein complex of the invention.

Recombinant Protein Expression

In general, preparation of the fusion protein complexes of the invention (e.g., components of a TxM complex) can be accomplished by procedures disclosed herein and by recognized recombinant DNA techniques.

In general, recombinant polypeptides are produced by transformation of a suitable host cell with all or part of a polypeptide-encoding nucleic acid molecule or fragment thereof in a suitable expression vehicle. Those skilled in the field of molecular biology will understand that any of a wide variety of expression systems may be used to provide the recombinant protein. The precise host cell used is not critical to the invention. A recombinant polypeptide may be produced in virtually any eukaryotic host (e.g., *Saccharomyces cerevisiae*, insect cells, e.g., Sf21 cells, or mammalian cells, e.g., NIH 3T3, HeLa, or preferably COS cells). Such cells are available from a wide range of sources (e.g., the American Type Culture Collection, Rockland, Md.; also, see, e.g., Ausubel et al., Current Protocol in Molecular Biology, New York: John Wiley and Sons, 1997). The method of transfection and the choice of expression vehicle will depend on the host system selected. Transformation methods are described, e.g., in Ausubel et al. (supra); expression vehicles may be chosen from those provided, e.g., in Cloning Vectors: A Laboratory Manual (P. H. Pouwels et al., 1985, Supp. 1987).

A variety of expression systems exist for the production of recombinant polypeptides. Expression vectors useful for producing such polypeptides include, without limitation, chromosomal, episomal, and virus-derived vectors, e.g., vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof.

Once the recombinant polypeptide is expressed, it is isolated, e.g., using affinity chromatography. In one example, an antibody (e.g., produced as described herein) raised against the polypeptide may be attached to a column and used to isolate the recombinant polypeptide. Lysis and fractionation of polypeptide-harboring cells prior to affinity chromatography may be performed by standard methods (see, e.g., Ausubel et al., supra). Once isolated, the recombinant protein can, if desired, be further purified, e.g., by high performance liquid chromatography (see, e.g., Fisher, Laboratory Techniques in Biochemistry and Molecular Biology, eds., Work and Burdon, Elsevier, 1980).

As used herein, biologically active polypeptides or effector molecules of the invention may include factors such as cytokines, chemokines, growth factors, protein toxins, immunoglobulin domains or other bioactive proteins such as enzymes. Also, biologically active polypeptides may include conjugates to other compounds such as non-protein toxins, cytotoxic agents, chemotherapeutic agents, detectable labels, radioactive materials and such.

Cytokines of the invention are defined by any factor produced by cells that affect other cells and are responsible for any of a number of multiple effects of cellular immunity. Examples of cytokines include but are not limited to the IL-2 family, interferon (IFN), IL-10, IL-12, IL-18, IL-1, IL-17, TGF and TNF cytokine families, and to IL-1 through IL-35, IFN-α, IFN-β, IFNγ, TGF-β, TNF-α, and TNFβ.

In an aspect of the invention, the first protein comprises a first biologically active polypeptide covalently linked to interleukin-15 (IL-15) domain or a functional fragment thereof. IL-15 is a cytokine that affects T-cell activation and proliferation. IL-15 activity in affecting immune cell activation and proliferation is similar in some respects to IL-2, although fundamental differences have been well characterized (Waldmann, T A, 2006, Nature Rev. Immunol. 6:595-601).

In another aspect of the invention, the first protein comprises an interleukin-15 (IL-15) domain that is an IL-15 variant (also referred to herein as IL-15 mutant). The IL-15 variant preferably comprises a different amino acid sequence that the native (or wild type) IL-15 protein. The IL-15 variant preferably binds the IL-15Rα polypeptide and functions as an IL-15 agonist or antagonist. Preferably, IL-15 variants with agonist activity have super agonist activity. The IL-15 variant can function as an IL-15 agonist or antagonist independent of its association with IL-15Rα. IL-15 agonists are exemplified by comparable or increased biological activity compared to wild type IL-15. IL-15 antagonists are exemplified by decreased biological activity compared to wild type IL-15 or by the ability to inhibit IL-15-mediated responses. In some examples, the IL-15 variant binds with increased or decreased activity to the IL-15RβγC receptors. In some cases, the sequence of the IL-15 variant has at least one amino acid change, e.g. substitution or deletion, compared to the native IL-15 sequence, such changes resulting in IL-15 agonist or antagonist activity. Preferably, the amino acid substitutions/deletions are in the domains of IL-15 that interact with IL-15Rβ and/or γC. More preferably, the amino acid substitutions/deletions do not affect binding to the IL-15Rα polypeptide or the ability to produce the IL-15 variant. Suitable amino acid substitutions/deletions to generate IL-15 variants can be identified based on putative or known IL-15 structures, comparisons of IL-15 with homologous molecules such as IL-2 with known structure, through rational or random mutagenesis and functional assays, as provided herein, or other empirical methods. Additionally, suitable amino acid substitutions can be conservative or non-conservative changes and insertions of additional amino acids. Preferably, IL-15 variants of the invention contain one or more than one amino acid substitutions/deletions at position 6, 8, 10, 61, 65, 72, 92, 101, 104, 105, 108, 109, 111, or 112 of the mature human IL-15 sequence; particularly, D8N ("D8" refers to the amino acid and residue position in the native mature human IL-15 sequence and "N" refers to the substituted amino acid residue at that position in the IL-15 variant), I6S, D8A, D61A, N65A, N72R, V104P or Q108A substitutions result in IL-15 variants with antagonist activity and N72D substitutions result in IL-15 variants with agonist activity.

Chemokines, similar to cytokines, are defined as any chemical factor or molecule which when exposed to other cells are responsible for any of a number of multiple effects of cellular immunity. Suitable chemokines may include but are not limited to the CXC, CC, C, and $CX_3C$ chemokine families and to CCL-1 through CCL-28, CXC-1 through CXC-17, XCL-1, XCL-2, CX3CL1, MIP-1b, IL-8, MCP-1, and Rantes.

Growth factors include any molecules which when exposed to a particular cell induce proliferation and/or differentiation of the affected cell. Growth factors include proteins and chemical molecules, some of which include: GM-CSF, G-CSF, human growth factor and stem cell growth factor. Additional growth factors may also be suitable for uses described herein.

Toxins or cytotoxic agents include any substance that has a lethal effect or an inhibitory effect on growth when exposed to cells. More specifically, the effector molecule can be a cell toxin of, e.g., plant or bacterial origin such as, e.g., diphtheria toxin (DT), shiga toxin, abrin, cholera toxin, ricin, saporin, pseudomonas exotoxin (PE), pokeweed antiviral protein, or gelonin. Biologically active fragments of such toxins are well known in the art and include, e.g., DT A chain and ricin A chain. Additionally, the toxin can be an agent active at the cell surface such as, e.g., phospholipase enzymes (e.g., phospholipase C).

Further, the effector molecule can be a chemotherapeutic drug such as, e.g., vindesine, vincristine, vinblastin, methotrexate, adriamycin, bleomycin, or cisplatin.

Additionally, the effector molecule can be a detectably-labeled molecule suitable for diagnostic or imaging studies. Such labels include biotin or streptavidin/avidin, a detectable nanoparticles or crystal, an enzyme or catalytically active fragment thereof, a fluorescent label such as green fluorescent protein, FITC, phycoerythrin, cychome, texas red or quantum dots; a radionuclide e.g., iodine-131, yttrium-90, rhenium-188 or bismuth-212; a phosphorescent or chemiluminescent molecules or a label detectable by PET, ultrasound or MRI such as Gd— or paramagnetic metal ion-based contrast agents. See e.g., Moskaug, et al. J. Biol. Chem. 264, 15709 (1989); Pastan, I. et al. Cell 47, 641, 1986; Pastan et al., Recombinant Toxins as Novel Therapeutic Agents, Ann. Rev. Biochem. 61, 331, (1992); "Chimeric Toxins" Olsnes and Phil, Pharmac. Ther., 25, 355 (1982); published PCT application no. WO 94/29350; published PCT application no. WO 94/04689; published PCT application no. WO2005046449 and U.S. Pat. No. 5,620,939 for disclosure relating to making and using proteins comprising effectors or tags.

The IL-15 and IL-15Rα polypeptides of the invention suitably correspond in amino acid sequence to naturally occurring IL-15 and IL-15Rα molecules, e.g. IL-15 and IL-15Rα molecules of a human, mouse or other rodent, or other mammal. Sequences of these polypeptides and encoding nucleic acids are known in the literature, including human interleukin 15 (IL15) mRNA—GenBank: U14407.1 (incorporated herein by reference), *Mus musculus* interleukin 15 (IL15) mRNA—GenBank: U14332.1 (incorporated herein by reference), human interleukin-15 receptor alpha chain precursor (IL15RA) mRNA—GenBank: U31628.1 (incorporated herein by reference), *Mus musculus* interleukin 15 receptor, alpha chain—GenBank: BC095982.1 (incorporated herein by reference).

In some settings, it can be useful to make the protein fusion or conjugate complexes of the present invention polyvalent, e.g., to increase the valency of the sc-antibody. In particular, interactions between the IL-15 and IL-15Rα domains of the fusion protein complex provide a means of generating polyvalent complexes. In addition, the polyvalent fusion protein can be made by covalently or non-covalently linking together between one and four proteins (the same or different) by using e.g., standard biotin-streptavidin labeling techniques, or by conjugation to suitable solid supports such as latex beads. Chemically cross-linked proteins (for example cross-linked to dendrimers) are also suitable polyvalent species. For example, the protein can be modified by including sequences encoding tag sequences that can be modified such as the biotinylation BirA tag or amino acid residues with chemically reactive side chains such as Cys or His. Such amino acid tags or chemically reactive amino acids may be positioned in a variety of positions in the fusion protein, preferably distal to the active site of the biologically active polypeptide or effector molecule. For example, the C-terminus of a soluble fusion protein can be covalently linked to a tag or other fused protein which includes such a reactive amino acid(s). Suitable side chains can be included to chemically link two or more fusion proteins to a suitable dendrimer or other nanoparticle to give a multivalent molecule. Dendrimers are synthetic chemical polymers that can have any one of a number of different functional groups of their surface (D. Tomalia, Aldrichimica Acta, 26:91:101 (1993)). Exemplary dendrimers for use in accordance with the present invention include e.g. E9 starburst polyamine dendrimer and E9 combust polyamine dendrimer, which can link cysteine residues. Exemplary nanoparticles include liposomes, core-shell particles or PLGA-based particles.

In another aspect, one or both of the polypeptides of the fusion protein complex comprises an immunoglobulin domain. Alternatively, the protein binding domain-IL-15 fusion protein can be further linked to an immunoglobulin domain. The preferred immunoglobulin domains comprise regions that allow interaction with other immunoglobulin domains to form multichain proteins as provided above. For example, the immunoglobulin heavy chain regions, such as the IgG1 $C_H2$-$C_H3$, are capable of stably interacting to create the Fc region. Preferred immunoglobulin domains including Fc domains also comprise regions with effector functions, including Fc receptor or complement protein binding activity, and/or with glycosylation sites. In some aspects, the immunoglobulin domains of the fusion protein complex contain mutations that reduce or augment Fc receptor or complement binding activity or glycosylation or dimerization, thereby affecting the biological activity of the resulting protein. For example, immunoglobulin domains containing mutations that reduce binding to Fc receptors could be used to generate fusion protein complex of the invention with lower binding activity to Fc receptor-bearing cells, which may be advantageous for reagents designed to recognize or detect specific antigens.

Nucleic Acids and Vectors

The invention further provides nucleic acid sequences and particularly DNA sequences that encode the present fusion proteins (e.g., components of TxM). Preferably, the DNA sequence is carried by a vector suited for extrachromosomal replication such as a phage, virus, plasmid, phagemid, cosmid, YAC, or episome. In particular, a DNA vector that encodes a desired fusion protein can be used to facilitate preparative methods described herein and to obtain significant quantities of the fusion protein. The DNA sequence can be inserted into an appropriate expression vector, i.e., a vector that contains the necessary elements for the transcription and translation of the inserted protein-coding sequence. A variety of host-vector systems may be utilized to express the protein-coding sequence. These include mammalian cell systems infected with virus (e.g., vaccinia virus, adenovirus, etc.); insect cell systems infected with virus (e.g., baculovirus); microorganisms such as yeast containing yeast vectors, or bacteria transformed with bacteriophage DNA, plasmid DNA or cosmid DNA. Depending on the host-vector system utilized, any one of a number of suitable transcription and translation elements may be used. See, Sambrook et al., supra and Ausubel et al. supra.

Included in the invention are methods for making a soluble fusion protein complex, the method comprising introducing into a host cell a DNA vector as described herein encoding the first and second proteins, culturing the host cell in media under conditions sufficient to express the fusion proteins in the cell or the media and allow association between IL-15 domain of a first protein and the soluble IL-15Rα domain of a second protein to form the soluble fusion protein complex, purifying the soluble fusion protein complex from the host cells or media.

In general, a preferred DNA vector according to the invention comprises a nucleotide sequence linked by phosphodiester bonds comprising, in a 5' to 3' direction a first cloning site for introduction of a first nucleotide sequence encoding a biologically active polypeptide, operatively linked to a sequence encoding an effector molecule.

The fusion protein components encoded by the DNA vector can be provided in a cassette format. By the term "cassette" is meant that each component can be readily substituted for another component by standard recombinant methods. In particular, a DNA vector configured in a cassette format is particularly desirable when the encoded fusion protein complex is to be used against pathogens that may have or have capacity to develop serotypes.

To make the vector coding for a fusion protein complex, the sequence coding for the biologically active polypeptide is linked to a sequence coding for the effector peptide by use of suitable ligases. DNA coding for the presenting peptide can be obtained by isolating DNA from natural sources such as from a suitable cell line or by known synthetic methods, e.g. the phosphate triester method. See, e.g., Oligonucleotide Synthesis, IRL Press (M. J. Gait, ed., 1984). Synthetic oligonucleotides also may be prepared using commercially available automated oligonucleotide synthesizers. Once isolated, the gene coding for the biologically active polypeptide can be amplified by the polymerase chain reaction (PCR) or other means known in the art. Suitable PCR primers to amplify the biologically active polypeptide gene may add restriction sites to the PCR product. The PCR product preferably includes splice sites for the effector peptide and leader sequences necessary for proper expression and secretion of the biologically active polypeptide-effector fusion complex. The PCR product also preferably includes a sequence coding for the linker sequence, or a restriction enzyme site for ligation of such a sequence.

The fusion proteins described herein are preferably produced by standard recombinant DNA techniques. For example, once a DNA molecule encoding the biologically active polypeptide is isolated, sequence can be ligated to another DNA molecule encoding the effector polypeptide. The nucleotide sequence coding for a biologically active polypeptide may be directly joined to a DNA sequence coding for the effector peptide or, more typically, a DNA sequence coding for the linker sequence as discussed herein may be interposed between the sequence coding for the biologically active polypeptide and the sequence coding for the effector peptide and joined using suitable ligases. The resultant hybrid DNA molecule can be expressed in a suitable host cell to produce the fusion protein complex. The DNA molecules are ligated to each other in a 5' to 3' orientation such that, after ligation, the translational frame of the encoded polypeptides is not altered (i.e., the DNA molecules are ligated to each other in-frame). The resulting DNA molecules encode an in-frame fusion protein.

Other nucleotide sequences also can be included in the gene construct. For example, a promoter sequence, which controls expression of the sequence coding for the biologically active polypeptide fused to the effector peptide, or a leader sequence, which directs the fusion protein to the cell surface or the culture medium, can be included in the construct or present in the expression vector into which the construct is inserted. An immunoglobulin or CMV promoter is particularly preferred.

In obtaining variant biologically active polypeptide, IL-15, IL-15Rα or Fc domain coding sequences, those of ordinary skill in the art will recognize that the polypeptides may be modified by certain amino acid substitutions, additions, deletions, and post-translational modifications, without loss or reduction of biological activity. In particular, it is well-known that conservative amino acid substitutions, that is, substitution of one amino acid for another amino acid of similar size, charge, polarity and conformation, are unlikely to significantly alter protein function. The 20 standard amino acids that are the constituents of proteins can be broadly categorized into four groups of conservative amino acids as follows: the nonpolar (hydrophobic) group includes alanine, isoleucine, leucine, methionine, phenylalanine, proline, tryptophan and valine; the polar (uncharged, neutral) group includes asparagine, cysteine, glutamine, glycine, serine, threonine and tyrosine; the positively charged (basic) group contains arginine, histidine and lysine; and the negatively charged (acidic) group contains aspartic acid and glutamic acid. Substitution in a protein of one amino acid for another within the same group is unlikely to have an adverse effect on the biological activity of the protein. In other instance, modifications to amino acid positions can be made to reduce or enhance the biological activity of the protein. Such changes can be introduced randomly or via site-specific mutations based on known or presumed structural or functional properties of targeted residue(s). Following expression of the variant protein, the changes in the biological activity due to the modification can be readily assessed using binding or functional assays.

Homology between nucleotide sequences can be determined by DNA hybridization analysis, wherein the stability of the double-stranded DNA hybrid is dependent on the extent of base pairing that occurs. Conditions of high temperature and/or low salt content reduce the stability of the hybrid, and can be varied to prevent annealing of sequences having less than a selected degree of homology. For instance, for sequences with about 55% G-C content, hybridization and wash conditions of 40-50 C, 6×SSC (sodium chloride/sodium citrate buffer) and 0.1% SDS (sodium dodecyl sulfate) indicate about 60-70% homology, hybridization and wash conditions of 50-65 C, 1×SSC and 0.1% SDS indicate about 82-97% homology, and hybridization and wash conditions of 52 C, 0.1×SSC and 0.1% SDS indicate about 99-100% homology. A wide range of computer programs for comparing nucleotide and amino acid sequences (and measuring the degree of homology) are also available, and a list providing sources of both commercially available and free software is found in Ausubel et al. (1999). Readily available sequence comparison and multiple sequence alignment algorithms are, respectively, the Basic Local Alignment Search Tool (BLAST) (Altschul et al., 1997) and ClustalW programs. BLAST is available on the world wide web at ncbi.nlm.nih.gov and a version of ClustalW is available at 2.ebi.ac.uk.

The components of the fusion protein can be organized in nearly any order provided each is capable of performing its intended function. For example, in one embodiment, the biologically active polypeptide is situated at the C or N terminal end of the effector molecule.

Preferred effector molecules of the invention will have sizes conducive to the function for which those domains are intended. The effector molecules of the invention can be made and fused to the biologically active polypeptide by a variety of methods including well-known chemical cross-linking methods. See, e.g., Means, G. E. and Feeney, R. E. (1974) in *Chemical Modification of Proteins*, Holden-Day. See also, S. S. Wong (1991) in *Chemistry of Protein Conjugation and Cross-Linking*, CRC Press. However it is generally preferred to use recombinant manipulations to make the in-frame fusion protein.

As noted, a fusion molecule or a conjugate molecule in accord with the invention can be organized in several ways. In an exemplary configuration, the C-terminus of the biologically active polypeptide is operatively linked to the N-terminus of the effector molecule. That linkage can be achieved by recombinant methods if desired. However, in another configuration, the N-terminus of the biologically active polypeptide is linked to the C-terminus of the effector molecule.

Alternatively, or in addition, one or more additional effector molecules can be inserted into the biologically active polypeptide or conjugate complexes as needed.

Vectors and Expression

A number of strategies can be employed to express the components of fusion protein complex of the invention (e.g., TxM). For example, a construct encoding one or more components of fusion protein complex of the invention can be incorporated into a suitable vector using restriction enzymes to make cuts in the vector for insertion of the construct followed by ligation. The vector containing the gene construct is then introduced into a suitable host for expression of the fusion protein. See, generally, Sambrook et al., supra. Selection of suitable vectors can be made empirically based on factors relating to the cloning protocol. For example, the vector should be compatible with, and have the proper replicon for the host that is being employed. The vector must be able to accommodate the DNA sequence coding for the fusion protein complex that is to be expressed. Suitable host cells include eukaryotic and prokaryotic cells, preferably those cells that can be easily transformed and exhibit rapid growth in culture medium. Specifically, preferred hosts cells include prokaryotes such as *E. coli, Bacillus subtillus*, etc. and eukaryotes such as animal cells and yeast strains, e.g., *S. cerevisiae*. Mammalian cells are generally preferred, particularly J558, NSO, SP2-O or CHO. Other suitable hosts include, e.g., insect cells such as Sf9. Conventional culturing conditions are employed. See, Sambrook, supra. Stable transformed or transfected cell lines can then be selected. Cells expressing a fusion protein complex of the invention can be determined by known procedures. For example, expression of a fusion protein complex linked to an immunoglobulin can be determined by an ELISA specific for the linked immunoglobulin and/or by immunoblotting. Other methods for detecting expression of fusion proteins comprising biologically active polypeptides linked to IL-15 or IL-15Rα domains are disclosed in the Examples.

As mentioned generally above, a host cell can be used for preparative purposes to propagate nucleic acid encoding a desired fusion protein. Thus, a host cell can include a prokaryotic or eukaryotic cell in which production of the fusion protein is specifically intended. Thus host cells specifically include yeast, fly, worm, plant, frog, mammalian cells and organs that are capable of propagating nucleic acid encoding the fusion. Non-limiting examples of mammalian cell lines which can be used include CHO dhfr-cells (Urlaub and Chasm, *Proc. Natl. Acad. Sci. USA*, 77:4216 (1980)), 293 cells (Graham et al., *J Gen. Virol.*, 36:59 (1977)) or myeloma cells like SP2 or NSO (Galfre and Milstein, *Meth. Enzymol.*, 73(B): 3 (1981)).

Host cells capable of propagating nucleic acid encoding a desired fusion protein complexes encompass non-mammalian eukaryotic cells as well, including insect (e.g., Sp. *frugiperda*), yeast (e.g., *S. cerevisiae, S. pombe, P. pastoris., K. lactis, H. polymorpha*; as generally reviewed by Fleer, R., *Current Opinion in Biotechnology*, 3(5):486496 (1992)), fungal and plant cells. Also contemplated are certain prokaryotes such as *E. coli* and *Bacillus*.

Nucleic acid encoding a desired fusion protein can be introduced into a host cell by standard techniques for transfecting cells. The term "transfecting" or "transfection" is intended to encompass all conventional techniques for introducing nucleic acid into host cells, including calcium phosphate co-precipitation, DEAE-dextran-mediated transfection, lipofection, electroporation, microinjection, viral transduction and/or integration. Suitable methods for transfecting host cells can be found in Sambrook et al. supra, and other laboratory textbooks.

Various promoters (transcriptional initiation regulatory region) may be used according to the invention. The selection of the appropriate promoter is dependent upon the proposed expression host. Promoters from heterologous sources may be used as long as they are functional in the chosen host.

Promoter selection is also dependent upon the desired efficiency and level of peptide or protein production. Inducible promoters such as tac are often employed in order to dramatically increase the level of protein expression in *E. coli*. Overexpression of proteins may be harmful to the host cells. Consequently, host cell growth may be limited. The use of inducible promoter systems allows the host cells to be cultivated to acceptable densities prior to induction of gene expression, thereby facilitating higher product yields.

Various signal sequences may be used according to the invention. A signal sequence which is homologous to the biologically active polypeptide coding sequence may be used. Alternatively, a signal sequence which has been selected or designed for efficient secretion and processing in the expression host may also be used. For example, suitable signal sequence/host cell pairs include the *B. subtilis* sacB signal sequence for secretion in *B. subtilis*, and the *Saccharomyces cerevisiae* α-mating factor or *P. pastoris* acid phosphatase phoI signal sequences for *P. pastoris* secretion. The signal sequence may be joined directly through the sequence encoding the signal peptidase cleavage site to the protein coding sequence, or through a short nucleotide bridge consisting of usually fewer than ten codons, where the bridge ensures correct reading frame of the downstream TCR sequence.

Elements for enhancing transcription and translation have been identified for eukaryotic protein expression systems. For example, positioning the cauliflower mosaic virus (CaMV) promoter 1,000 bp on either side of a heterologous promoter may elevate transcriptional levels by 10- to 400-fold in plant cells. The expression construct should also include the appropriate translational initiation sequences. Modification of the expression construct to include a Kozak consensus sequence for proper translational initiation may increase the level of translation by 10 fold.

A selective marker is often employed, which may be part of the expression construct or separate from it (e.g., carried by the expression vector), so that the marker may integrate at a site different from the gene of interest. Examples include markers that confer resistance to antibiotics (e.g., bla confers resistance to ampicillin for *E. coli* host cells, nptII confers kanamycin resistance to a wide variety of prokaryotic and eukaryotic cells) or that permit the host to grow on minimal medium (e.g., HIS4 enables *P. pastoris* or His *S. cerevisiae* to grow in the absence of histidine). The selectable marker has its own transcriptional and translational initiation and termination regulatory regions to allow for independent expression of the marker. If antibiotic resistance is employed as a marker, the concentration of the antibiotic for selection will vary depending upon the antibiotic, generally ranging from 10 to 600 µg of the antibiotic/mL of medium.

The expression construct is assembled by employing known recombinant DNA techniques (Sambrook et al., 1989; Ausubel et al., 1999). Restriction enzyme digestion and ligation are the basic steps employed to join two fragments of DNA. The ends of the DNA fragment may require modification prior to ligation, and this may be accomplished by filling in overhangs, deleting terminal portions of the fragment(s) with nucleases (e.g., ExoIII), site directed mutagenesis, or by adding new base pairs by PCR. Polylinkers and adaptors may be employed to facilitate joining of selected fragments. The expression construct is typically assembled in stages employing rounds of restriction, ligation, and transformation of *E. coli*. Numerous cloning vectors suitable for construction of the expression construct are known in the art (λZAP and pBLUESCRIPT SK-1, Stratagene, La Jolla, CA, pET, Novagen Inc., Madison, WI, cited in Ausubel et al., 1999) and the particular choice is not critical to the invention. The selection of cloning vector will be influenced by the gene transfer system selected for introduction of the expression construct into the host cell. At the end of each stage, the resulting construct may be analyzed by restriction, DNA sequence, hybridization and PCR analyses.

The expression construct may be transformed into the host as the cloning vector construct, either linear or circular, or may be removed from the cloning vector and used as is or introduced onto a delivery vector. The delivery vector facilitates the introduction and maintenance of the expression construct in the selected host cell type. The expression construct is introduced into the host cells by any of a number of known gene transfer systems (e.g., natural competence, chemically mediated transformation, protoplast transformation, electroporation, biolistic transformation, transfection, or conjugation) (Ausubel et al., 1999; Sambrook et al., 1989). The gene transfer system selected depends upon the host cells and vector systems used.

For instance, the expression construct can be introduced into S. cerevisiae cells by protoplast transformation or electroporation. Electroporation of S. cerevisiae is readily accomplished, and yields transformation efficiencies comparable to spheroplast transformation.

The present invention further provides a production process for isolating a fusion protein of interest. In the process, a host cell (e.g., a yeast, fungus, insect, bacterial or animal cell), into which has been introduced a nucleic acid encoding the protein of the interest operatively linked to a regulatory sequence, is grown at production scale in a culture medium to stimulate transcription of the nucleotides sequence encoding the fusion protein of interest. Subsequently, the fusion protein of interest is isolated from harvested host cells or from the culture medium. Standard protein purification techniques can be used to isolate the protein of interest from the medium or from the harvested cells. In particular, the purification techniques can be used to express and purify a desired fusion protein on a large-scale (i.e. in at least milligram quantities) from a variety of implementations including roller bottles, spinner flasks, tissue culture plates, bioreactor, or a fermentor.

An expressed protein fusion complex can be isolated and purified by known methods. Typically the culture medium is centrifuged or filtered and then the supernatant is purified by affinity or immunoaffinity chromatography, e.g. Protein-A or Protein-G affinity chromatography or an immunoaffinity protocol comprising use of monoclonal antibodies that bind the expressed fusion protein complex. The fusion proteins of the present invention can be separated and purified by appropriate combination of known techniques. These methods include, for example, methods utilizing solubility such as salt precipitation and solvent precipitation, methods utilizing the difference in molecular weight such as dialysis, ultra-filtration, gel-filtration, and SDS-polyacrylamide gel electrophoresis, methods utilizing a difference in electrical charge such as ion-exchange column chromatography, methods utilizing specific affinity such as affinity chromatography, methods utilizing a difference in hydrophobicity such as reverse-phase high performance liquid chromatography and methods utilizing a difference in isoelectric point, such as isoelectric focusing electrophoresis, metal affinity columns such as Ni-NTA. See generally Sambrook et al. and Ausubel et al. supra for disclosure relating to these methods.

It is preferred that the fusion proteins of the present invention be substantially pure. That is, the fusion proteins have been isolated from cell substituents that naturally accompany it so that the fusion proteins are present preferably in at least 80% or 90% to 95% homogeneity (w/w). Fusion proteins having at least 98 to 99% homogeneity (w/w) are most preferred for many pharmaceutical, clinical and research applications. Once substantially purified the fusion protein should be substantially free of contaminants for therapeutic applications. Once purified partially or to substantial purity, the soluble fusion proteins can be used therapeutically, or in performing in vitro or in vivo assays as disclosed herein. Substantial purity can be determined by a variety of standard techniques such as chromatography and gel electrophoresis.

The present fusion protein complexes are suitable for in vitro or in vivo use with a variety of cells that are cancerous or are infected or that may become infected by one or more diseases.

Human interleukin-15 (huIL-15) is trans-presented to immune effector cells by the human IL-15 receptor α chain (huIL-15Rα) expressed on antigen presenting cells. IL-15Rα binds huIL-15 with high affinity (38 pM) primarily through the extracellular sushi domain (huIL-15RαSu). As described herein, the huIL-15 and huIL-15RαSu domains can be used as a scaffold to construct multi-domain fusion protein complexes.

IgG domains, particularly the Fc fragment, have been used successfully as dimeric scaffolds for a number of therapeutic molecules including approved biologic drugs. For example, etanercept is a dimer of soluble human p75 tumor necrosis factor-α (TNF-α) receptor (sTNFR) linked to the Fc domain of human IgG1. This dimerization allows etanercept to be up to 1,000 times more potent at inhibiting TNF-α activity than the monomeric sTNFR and provides the fusion with a five-fold longer serum half-life than the monomeric form. As a result, etanercept is effective at neutralization of the pro-inflammatory activity of TNF-α in vivo and improving patient outcomes for a number of different autoimmune indications.

In addition to its dimerization activity, the Fc fragment also provides cytotoxic effector functions through the complement activation and interaction with Fcγ receptors displayed on natural killer (NK) cells, neutrophils, phagocytes and dendritic cells. In the context of anti-cancer therapeutic antibodies and other antibody domain-Fc fusion proteins, these activities likely play an important role in efficacy observed in animal tumor models and in cancer patients. However these cytotoxic effector responses may not be sufficient in a number of therapeutic applications. Thus, there has been considerable interest in improving and expanding on the effector activity of the Fc domain and developing other means of recruiting cytolytic immune responses, including T cell activity, to the disease site via targeted therapeutic molecules. IgG domains have been used as a scaffold to form bispecific antibodies to improve the quality and quantity of products generated by the traditional hybridoma fusion technology. Although these methods bypass the shortcomings of other scaffolds, it has been difficult to produce bispecific antibodies in mammalian cells at levels sufficient to support clinical development and use.

In an effort to develop human-derived immunostimulatory multimeric scaffold, human IL-15 (huIL-15) and IL-15 receptor domains were used. huIL-15 is a member of the small four α-helix bundle family of cytokines that associates with the huIL-15 receptor α-chain (huIL-15Rα) with a high binding affinity (equilibrium dissociation constant (KD) ~$10^{-11}$ M). The resulting complex is then trans-presented to the human IL-2/15 receptor β/common γ chain (huIL-15RβγC) complexes displayed on the surface of T cells and NK cells. This cytokine/receptor interaction results in expansion and activation of effector T cells and NK cells, which play an important role in eradicating virally infected and malignant cells. Normally, huIL-15 and huIL-15Rα are co-produced in dendritic cells to form complexes intracellularly that are subsequently secreted and displayed as heterodimeric molecules on cell surfaces. Thus, the characteristics of huIL-15 and huIL-15Rα interactions suggest that these inter chain binding domains could serve as a human-derived immunostimulatory scaffold to make soluble dimeric molecules capable of target-specific binding.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of the invention, and, as such, may be considered in making and practicing the invention. Particularly useful techniques for particular embodiments will be discussed in the sections that follow.

The following examples are put forth so as to provide those of ordinary skill in the art with a complete disclosure and description of how to make and use the assay, screening, and therapeutic methods of the invention, and are not intended to limit the scope of what the inventors regard as their invention.

EXAMPLES

Example 1: Generation and Characterization of Fusion Protein Complexes Comprising IL-15, IL-12 and IL-18 Domains An important therapeutic approach for treating cancer or infectious disease relies on augmenting immune cell activity against the diseased cells. This strategy includes stimulating immune cells ex vivo followed by adoptive transfer and/or directly increasing immune cell levels or activity in vivo in the patient. Immune cells involved in these approaches may be those of the innate (i.e., NK cells) or adaptive (i.e., T cells) immune system.

One approach for augmenting immune activity is to provide immunostimulatory cytokines to the immune cells. Such cytokines are known in the art and can be used alone or in combination with other cytokines or agents. As described in detail below, fusion protein complexes comprising an IL-15N72D:IL-15RαSu/Fc scaffold fused to IL-12 and/or IL-18 binding domains were generated (FIG. 1A and FIG. 1B). These fusion protein complexes have advantages in binding to NK cells and signaling cell responses via each of the cytokine receptors. The Fc region of Ig molecules forms a dimer to provide a soluble multi-polypeptide complex, can bind Protein A for the purpose of purification and can interact with Fcγ receptors on NK cells and macrophages, thus providing advantages to the fusion protein complex that are not present in the combination of individual cytokines. Additionally, interactions between the IL-15N72D and IL-15RαSu domains provides a means to link the IL-15N72D, IL-12 and IL-18 (and possibly other protein domains or agents) into a single immunostimulatory fusion protein complex.

Specifically, constructs were made linking IL-12 and/or IL-18 domains to the IL-15N72D and IL-15RαSu/Fc chains. In the case of IL-12, the mature cytokine consists of two polypeptide subunits (p40 and p35) that can be linked via a flexible linker sequence to generate an active single-chain form. In some cases, either IL-12 or IL-18 polypeptide is linked to the N-terminus of the IL-15N72D and/or IL-15RαSu/Fc chains. In other cases, the IL-12 or IL-18 polypeptide is linked to the N-terminus of IL-15N72D and/or IL-15RαSu/Fc chains. Specific fusion protein complexes comprising an IL-15N72D:IL-15RαSu/Fc scaffold fused to IL-12 and/or IL-18 binding domains are described below.

1) A fusion protein complex was generated comprising LL-12/IL-15RαSu/Fc and IL-18/IL-15N72D fusion proteins. The human IL-12 subunit sequences and human IL-18 sequence were obtained from the UniProt website and DNA for these sequences was synthesized by Genewiz. Specifically, constructs were made linking the IL-12 subunit beta (p40) to IL-12 subunit alpha (p35) to generate a single chain version of IL-12 and then directly linking the IL-12 sequence to the IL-15RαSu/Fc chain. The synthesized IL-12 sequence was linked to the N-terminal coding region of IL-15RαSu/Fc via overlapping PCR. The nucleic acid and protein sequences of a construct comprising IL-12 linked to the N-terminus of IL-15RαSu/Fc are shown below.

The nucleic acid sequence of the IL-12/IL-15RαSu/Fc construct (including signal peptide sequence) is as follows (SEQ ID NO: 1):

```
(Signal peptide)
atgaagtgggtgaccttcatcagcctgctgttcctgttctccagcgccta ctcc (Human IL-12 subunit beta (p40))
atctgggagctgaagaaagacgtgtatgtcgtggagctggactggtatcc tgacgcccccggcgagatggtggtgctgacatgcgacacccctgaggagg atggcatcacatggaccctggaccaaagcagcgaggtgctgggctccgga aagaccctgaccatccaggtgaaggagttcggcgacgccggccagtatac ctgccataagggaggcgaggtgctgtcccactccctgctcctgctgcaca agaaggaagatggcatctggagcaccgatattctgaaggaccagaaggag cccaagaacaaaacctttctgcggtgcgaggccaagaattattccggcag gttcacctgctggtggctgaccacaatctccaccgacctgaccttcagcg tcaagagctccaggggatcctccgatcctcagggcgtgacctgtggagct gccaccctgtccgctgagagggtgaggggcgacaacaaggagtacgagta ctccgtcgagtgtcaggaggactccgcctgccctgctgccgaagagagcc tgcctatcgaagtcatggtggacgccgtgcacaagctgaagtatgagaac tacaccagcagcttcttcatccgggacattatcaagcctgatccccctaa gaacctgcagctcaagcccctgaagaattcccggcaagtcgaggtgtcct gggagtaccccgacacctggtccacccctcactcctattttagcctgacc ttctgcgtgcaggtgcagggcaagagcaagagggagaagaaagaccgggt gttcaccgacaagaccagcgctaccgtgatctgtcggaagaacgcttcca tttccgtgcgggctcaggacaggtattactcctcctcctggtccgagtgg gctagcgtcccctgcagc (Linker)
ggaggtggcggatccggaggtggaggttctggtggaggtgggagt
```

(Human IL-12 subunit alpha (p35))
aggaacctgcccgtggctacacccgaccctggaatgttcccctgtctcca ccacagccaaaacctcctgcgggccgtgtccaacatgctgcaaaaggctc ggcagacactggagttctaccccctgcaccagcgaggagatcgaccatgag gacatcacaaaggacaagacaagcaccgtggaggcttgcctcccccctgga actgaccaagaatgagtcctgcctcaacagccgggagacatccttcatca ccaatggctcctgtctggcttcccggaagacaagcttcatgatggccctg tgcctgtccagcatctatgaggacctgaagatgtaccaggtcgagtttaa gaccatgaacgccaagctgctgatggaccccaagcggcaaatcttcctgg accagaacatgctggctgtgatcgacgagctgatgcaggctctgaacttc aacagcgagaccgtgcccagaagtcctccctggaggagcctgattttta caagaccaaaatcaagctctgcatcctcctgcacgccttccggatcaggg ccgtgaccatcgatcgggtgatgtcctacctgaatgcttcc (Human IL-15R α sushi domain)
atcacgtgtcctcctcctatgtccgtggaacacgcagacatctgggtcaa gagctacagcttgtactccaggagcggtacatttgtaactctggtttca agcgtaaagccggcacgtccagcctgacggagtgcgtgttgaacaaggcc acgaatgtcgcccactggacaaccccccagtctcaaatgcattagA (Human IgG1 CH2-CH3 (Fc) domain)
gagccgaaatcttgtgacaaaactcacacatgcccaccgtgcccagcacc tgaactcctgggggaccgtcagtcttcctcttccccccaaaacccaagg acaccctcatgatctcccggacccctgaggtcacatgcgtggtggtggac gtgagccacgaagaccctgaggtcaagttcaactggtacgtggacggcgt ggaggtgcataatgccaagacaaagccgcgggaggagcagtacaacagca cgtaccgtgtggtcagcgtcctcaccgtcctgcaccaggactggctgaat ggcaaggagtacaagtgcaaggtctccaacaaagccctcccagcccccat cgagaaaaccatctccaaagccaaagggcagccccgagaaccacaggtgt acaccctgcccccatcccgggatgagctgaccaagaaccaggtcagcctg acctgcctggtcaaaggcttctatcccagcgacatcgccgtggagtggga gagcaatgggcagccggagaacaactacaagaccacgcctcccgtgctgg actccgacggctccttcttcctctacagcaagctcaccgtggacaagagc aggtggcagcaggggaacgtcttctcatgctccgtgatgcatgaggctct gcacaaccactacacgcagaagagcctctccctgtctctggtaaa The amino acid sequence of the IL-12/IL-15RαSu/Fc fusion protein (including signal peptide sequence) is as follows (SEQ ID NO: 2):

(Signal peptide)
MKWVTFISLLFLFSSAYS (Human IL-12 subunit beta (p40))
IWELKKDVYVVELDWYPDAPGEMVVLTCDTPEEDGITWTLDQSSEVLGSG

KTLTIQVKEFGDAGQYTCHKGGEVLSHSLLLLHKKEDGIWSTDILKDQKE

PKNKTFLRCEAKNYSGRFTCWWLTTISTDLTFSVKSSRGSSDPQGVTCGA

ATLSAERVRGDNKEYEYSVECQEDSACPAAEESLPIEVMVDAVHKLKYEN

YTSSFFIRDIIKPDPPKNLQLKPLKNSRQVEVSWEYPDTWSTPHSYFSLT

FCVQVQGKSKREKKDRVFTDKTSATVICRKNASISVRAQDRYYSSSWSEW

ASVPCS (Linker)
GGGGSGGGGSGGGGS (Human IL-12 subunit alpha (p35))
RNLPVATPDPGMFPCLHHSQNLLRAVSNMLQKARQTLEFYPCTSEEIDHE

DITKDKTSTVEACLPLELTKNESCLNSRETSFITNGSCLASRKTSFMMAL

CLSSIYEDLKMYQVEFKTMNAKLLMDPKRQIFLDQNMLAVIDELMQALNF

NSETVPQKSSLEEPDFYKTKIKLCILLHAFRIRAVTIDRVMSYLNAS (Human IL-15R α sushi domain)
ITCPPPMSVEHADIWVKSYSLYSRERYICNSGFKRKAGTSSLTECVLNKA

TNVAHWTTPSLKCIR (Human IgG1 CH2-CH3 (Fc) domain)
EPKSCDKTHTCPPCPAPELLGGPSVFLFPPKPKDTLMISRTPEVTCVVVD

VSHEDPEVKFNWYVDGVEVHNAKTKPREEQYNSTYRVVSVLTVLHQDWLN

GKEYKCKVSNKALPAPIEKTISKAKGQPREPQVYTLPPSRDELTKNQVSL

TCLVKGFYPSDIAVEWESNGQPENNYKTTPPVLDSDGSFFLYSKLTVDKS

RWQQGNVFSCSVMHEALHNHYTQKSLSLSPGK

In some cases, the leader peptide is cleaved from the intact polypeptide to generate the mature form that may be soluble or secreted.

Constructs were also made linking the synthesized IL-18 sequence to the N-terminus coding region of IL-15N72D via overlapping PCR. The nucleic acid and protein sequences of a construct comprising IL-18 linked to the N-terminus of IL-15N72D are shown below.

The nucleic acid sequence of the IL-18/IL-15N72D construct (including leader sequence) is as follows (SEQ ID NO: 3):

(Signal peptide)
atgaagtgggtgaccttcatcagcctgctgttcctgttctccagcgccta ctcc (Human IL-18)
tacttcggcaagctggagtccaagctgtccgtgatcaggaacctgaacga ccaggtgctgttcatcgaccagggcaacaggcccctgttcgaggacatga ccgactccgactgcagggacaacgcccctaggaccatcttcatcatctcc atgtataaggacagccagcccaggggaatggccgtgaccatctccgtgaa gtgcgagaagatctccaccctgtcctgcgagaacaagatcatctccttca aggagatgaaccccccgacaacatcaaggacaccaagtccgacatcatc ttcttccagcggtccgtgcccggacacgacaacaagatgcagttcgagtc ctcctcctacgagggctactttctggcctgtgagaaggagagggacctct tcaagctcatcctgaagaaggaggacgagctgggcgacaggtccatcatg ttcaccgtgcagaacgaggac (Human IL-15N72D)
aactgggttaacgtaataagtgatttgaaaaaaattgaagatcttattca atctatgcatattgatgctactttatatacggaaagtgatgttcacccca -continued
```
gttgcaaagtaacagcaatgaagtgctttctcttggagttacaagttatt tcacttgagtccggagatgcaagtattcatgatacagtagaaaatctgat catcctagcaaacgacagtttgtcttctaatgggaatgtaacagaatctg gatgcaaagaatgtgaggaactggaggaaaaaaatattaaagaatttttg cagagttttgtacatattgtccaaatgttcatcaacacttct
```

The amino acid sequence of the IL-18/IL-15N72D fusion protein (including leader sequence) is as follows (SEQ ID NO: 4):

```
(Signal peptide)
MKWVTFISLLFLFSSAYS (Human IL-18)
YFGKLESKLSVIRNLNDQVLFIDQGNRPLFEDMTDSDCRDNAPRTIFIIS

MYKDSQPRGMAVTISVKCEKISTLSCENKIISFKEMNPPDNIKDTKSDII

FFQRSVPGHDNKMQFESSSYEGYFLACEKERDLFKLILKKEDELGDRSIM

FTVQNED (Human IL-15N72D)
NWVNVISDLKKIEDLIQSMHIDATLYTESDVHPSCKVTAMKCFLLELQVI

SLESGDASIHDTVENLIILANDSLSSNGNVTESGCKECEELEEKNIKEFL

QSFVHIVQMFINTS
```

In some cases, the leader peptide is cleaved from the intact polypeptide to generate the mature form that may be soluble or secreted.

Figure 2A:
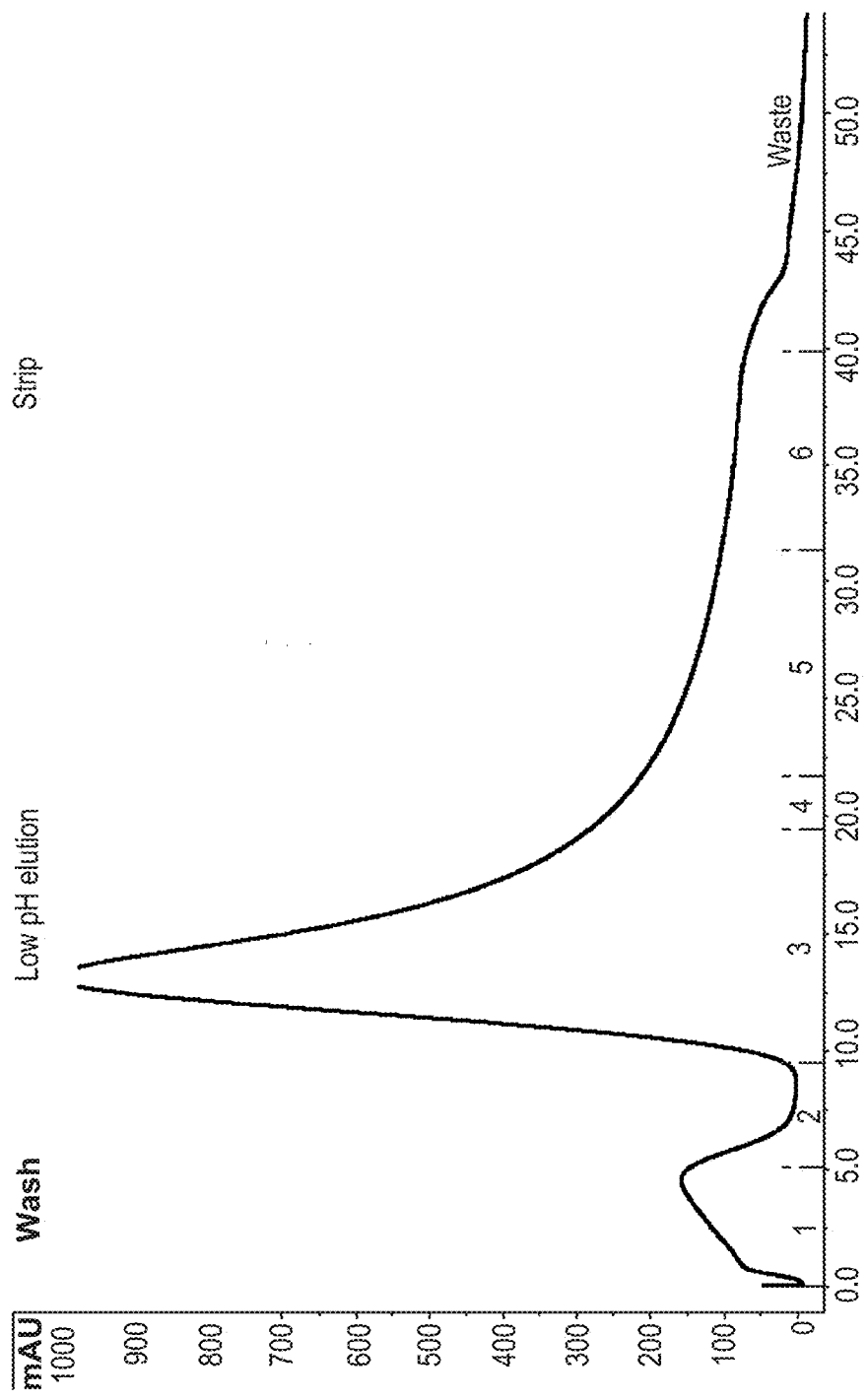
FIG. 2A is a line graph showing the chromatographic profile of hIL18/IL12/TxM protein-containing cell culture supernatant following binding and elution on a Protein A resin.

The IL-12/IL-15RαSu/Fc and IL-18/IL-15N72D constructs were cloned into expression vectors as described previously (U.S. Pat. No. 8,507,222, at Example 1, incorporated herein by reference), and the expression vectors were transfected into CHO cells. Co-expression of the two constructs in CHO cells allowed for formation and secretion of a soluble IL-18/IL-15N72D:IL-12/IL-15RαSu/Fc fusion protein complex (referred to as hIL18/IL12/TxM). The hIL18/IL12/TxM protein was purified from CHO cell culture supernatant by Protein A affinity chromatography and size exclusion chromatography resulting in soluble (non-aggregated) fusion protein complexes consisting of IL-12/IL-15RαSu/Fc dimers and IL-18/IL-15N72D fusion proteins (FIG. 2A-2C).

Figure 3:
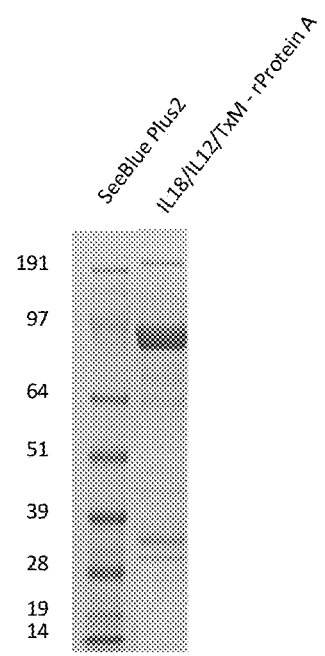
FIG. 3 is a photograph showing a sodium dodecyl sulfate polyacrylamide gel (4-12%) electrophoresis (SDS-PAGE) analysis of the hIL18/IL12/TxM fusion protein complex following disulfide bond reduction. Left lane: See Blue Plus2 marker, right lane: Protein A-purified hIL18/IL12/TxM.

Reduced SDS-PAGE analysis of the Protein A-purified IL-18/IL-15N72D:IL-12/IL-15RαSu/Fc fusion protein complexes is shown in FIG. 3. Bands corresponding to the soluble IL-12/IL-15RαSu/Fc and IL-18/IL-15N72D proteins at ~90 kDa and ~30 kDa, respectively, were observed (FIG. 3).

2) For a second approach, a similar fusion protein complex was generated comprising IL-18/IL-15RαSu/Fc and IL-12/IL-15N72D fusion proteins. Specifically, constructs were made by attaching IL-18 directly to the IL-15RαSu/Fc chain. The synthesized IL-18 is linked to the N-terminal coding region of IL-15RαSu/Fc via overlapping PCR. The nucleic acid and protein sequences of a construct comprising the IL-18 linked to the N-terminus of IL-15RαSu/Fc are shown below.

The nucleic acid sequence of the IL-18/IL-15RαSu/Fc construct (including signal peptide sequence) is as follows (SEQ ID NO: 5):

```
(Signal peptide)
atgaagtgggtgaccttcatcagcctgctgttcctgttctccagcgccta ctcc (Human IL-18)
tacttcggcaagctggagtccaagctgtccgtgatcaggaacctgaacga ccaggtgctgttcatcgaccagggcaacaggcccctgttcgaggacatga ccgactccgactgcagggacaacgcccctaggaccatcttcatcatctcc atgtataaggacagccagcccaggggaatggccgtgaccatctccgtgaa gtgcgagaagatctccaccctgtcctgcgagaacaagatcatctccttca aggagatgaaccccccccgacaacatcaaggacaccaagtccgacatcatc ttcttccagcggtccgtgcccggacacgacaacaagatgcagttcgagtc ctcctcctacgagggctactttctggcctgtgagaaggagagggacctct tcaagctcatcctgaagaaggaggacgagctgggcgacaggtccatcatg ttcaccgtgcagaacgaggac (Human IL-15R α sushi domain)
atcacgtgtcctcctcctatgtccgtggaacacgcagacatctgggtcaa gagctacagcttgtactccagggagcggtacatttgtaactctggtttca agcgtaaagccggcacgtccagcctgacggagtgcgtgttgaacaaggcc acgaatgtcgcccactggacaaccccagtctcaaatgcattaga (Human IgG1 CH2-CH3 (Fc) domain)
gagccgaaatcttgtgacaaaactcacacatgcccaccgtgcccagcacc tgaactcctggggggaccgtcagtcttcctcttccccccaaaacccaagg acaccctcatgatctcccggacccctgaggtcacatgcgtggtggtggac gtgagccacgaagaccctgaggtcaagttcaactggtacgtggacggcgt ggaggtgcataatgccaagacaaagccgcgggaggagcagtacaacagca cgtaccgtgtggtcagcgtcctcaccgtcctgcaccaggactggctgaat ggcaaggagtacaagtgcaaggtctccaacaaagcccteccagecccccat cgagaaaaccatctccaaagccaaagggcagccccgagaaccacaggtgt acaccctgcccccatcccgggatgagctgaccaagaaccaggtcagcctg acctgcctggtcaaaggcttctatcccagcgacatcgccgtggagtggga gagcaatgggcagccggagaacaactacaagaccacgcctcccgtgctgg actccgacggctccttcttcctctacagcaagctcaccgtggacaagagc aggtggcagcaggggaacgtcttctcatgctccgtgatgcatgaggctct gcacaaccactacacgcagaagagcctctccctgtctccggtaaa
```

The amino acid sequence of the IL-18/IL-15RαSu/Fc fusion protein (including signal peptide sequence) is as follows (SEQ ID NO: 6):

```
(Signal peptide)
MKWVTFISLLFLFSSAYS (Human IL-18)
YFGKLESKLSVIRNLNDQVLFIDQGNRPLFEDMTDSDCRDNAPRTIFIIS

MYKDSQPRGMAVTISVKCEKISTLSCENKIISFKEMNPPDNIKDTKSDII

FFQRSVPGHDNKMQFESSSYEGYFLACEKERDLFKLILKKEDELGDRSIM

FTVQNED
```

(Human IL-15R α sushi domain)
ITCPPPMSVEHADIWVKSYSLYSRERYICNSGFKRKAGTSSLTECVLNKA

TNVAHWTTPSLKCIR (Human IgG1 CH2-CH3 (Fc) domain)
EPKSCDKTHTCPPCPAPELLGGPSVFLFPPKPKDTLMISRTPEVTCVVVD

VSHEDPEVKFNWYVDGVEVHNAKTKPREEQYNSTYRVVSVLTVLHQDWLN

GKEYKCKVSNKALPAPIEKTISKAKGQPREPQVYTLPPSRDELTKNQVSL

TCLVKGFYPSDIAVEWESNGQPENNYKTTPPVLDSDGSFFLYSKLTVDKS

RWQQGNVFSCSVMHEALHNHYTQKSLSLSPGK

In some cases, the leader peptide is cleaved from the intact polypeptide to generate the mature form that may be soluble or secreted.

Constructs were also made linking the synthesized IL-12 sequence to the N-terminus coding region of IL-15N72D via overlapping PCR. As describe above, a single-chain version of IL-12 (p40-linker-p35) was used. The nucleic acid sequence of the IL-12/IL-15N72D construct (including leader sequence) is as follows (SEQ ID NO: 7):

(Signal peptide)
atgaagtgggtgaccttcatcagcctgctgttcctgttctccagcgccta ctcc (Human IL-12 subunit beta (p40))
atctgggagctgaagaaagacgtgtatgtcgtggagctggactggtatcc tgacgcccccggcgagatggtggtgctgacatgcgacacccctgaggagg atggcatcacatggaccctggaccaaagcagcgaggtgctgggctccgga aagaccctgaccatccaggtgaaggagttcggcgacgccggccagtatac ctgccataagggaggcgaggtgctgtcccactccctgctcctgctgcaca agaaggaagatggcatctggagcaccgatattctgaaggaccagaaggag cccaagaacaaaaccttttctgcggtgcgaggccaagaattattccggcag gttcacctgctggtggctgaccacaatctccaccgacctgaccttcagcg tcaagagctccaggggatcctccgatcctcagggcgtgacctgtggagct gccaccctgtccgctgagagggtgaggggcgacaacaaggagtacgagta ctccgtcgagtgtcaggaggactccgcctgccctgctgccgaagagagcc tgcctatcgaagtcatggtggacgccgtgcacaagctgaagtatgagaac tacaccagcagcttcttcatccgggacattatcaagcctgatcccctaa gaacctgcagctcaagcccctgaagaattcccggcaagtcgaggtgtcct gggagtaccccgacacctggtccacccctcactcctattttagcctgacc ttctgcgtgcaggtgcagggcaagagcaagagggagaagaaagaccggt gttcaccgacaagaccagcgctaccgtgatctgtcggaagaacgcttca tttccgtgcgggctcaggacaggtattactcctcctcctggtccgagtgg gctagcgtccctgcagc (Linker)
ggaggtggcggatccggaggtggaggttctggtggaggtgggagt (Human IL-12 subunit alpha (p35))
aggaacctgcccgtggctacacccgacccctggaatgttcccctgtctcca ccacagccaaaacctcctgcgggccgtgtccaacatgctgcaaaaggctc ggcagacactggagttctaccectgcaccagcgaggagatcgaccatgag gacatcacaaaggacaagacaagcaccgtggaggcttgcctcccctga actgaccaagaatgagtcctgcctcaacagccgggagacatccttcatca ccaatggctcctgtctggcttcccggaagacaagcttcatgatggccctg tgcctgtccagcatctatgaggacctgaagatgtaccaggtcgagtttaa gaccatgaacgccaagctgctgatggaccccaagcggcaaatcttcctgg accagaacatgctggctgtgatcgacgagctgatgcaggctctgaacttc aacagcgagaccgtgccccagaagtcctccctggaggagcctgattttta caagaccaaaatcaagctctgcatcctcctgcacgccttccggatcaggg ccgtgaccatcgatcgggtgatgtcctacctgaatgcttcc (Human IL-15N72D)
aactgggttaacgtaataagtgatttgaaaaaaattgaagatcttattca atctatgcatattgatgctactttatatacggaaagtgatgttcacccca gttgcaaagtaacagcaatgaagtgctttctcttggagttacaagttatt tcacttgagtccggagatgcaagtattcatgatacagtagaaaatctgat catcctagcaaacgacagtttgtcttctaatgggaatgtaacagaatctg gatgcaaagaatgtgaggaactggaggaaaaaaatattaaagaattttg cagagttttgtacatattgtccaaatgttcatcaacacttct The amino acid sequence of the IL-12/IL-15N72D fusion protein (including leader sequence) is as follows (SEQ ID NO: 8):

(Signal peptide)
MKWVTFISLLFLFSSAYS (Human IL-12 subunit beta (p40))
IWELKKDVYVVELDWYPDAPGEMVVLTCDTPEEDGITWTLDQSSEVLGSG

KTLTIQVKEFGDAGQYTCHKGGEVLSHSLLLLHKKEDGIWSTDILKDQKE

PKNKTFLRCEAKNYSGRFTCWWLTTISTDLTFSVKSSRGSSDPQGVTCGA

ATLSAERVRGDNKEYEYSVECQEDSACPAAEESLPIEVMVDAVHKLKYEN

YTSSFFIRDIIKPDPPKNLQLKPLKNSRQVEVSWEYPDTWSTPHSYFSLT

FCVQVQGKSKREKKDRVFTDKTSATVICRKNASISVRAQDRYYSSSWSEW

ASVPCS (Linker)
GGGGSGGGGSGGGGS (Human IL-12 subunit alpha (p35))
RNLPVATPDPGMFPCLHHSQNLLRAVSNMLQKARQTLEFYPCTSEEIDHE

DITKDKTSTVEACLPLELTKNESCLNSRETSFITNGSCLASRKTSFMMAL

CLSSIYEDLKMYQVEFKTMNAKLLMDPKRQIFLDQNMLAVIDELMQALNF

NSETVPQKSSLEEPDFYKTKIKLCILLHAFRIRAVTIDRVMSYLNAS (Human IL-15N72D)
NWVNVISDLKKIEDLIQSMHIDATLYTESDVHPSCKVTAMKCFLLELQVI

SLESGDASIHDTVENLIILANDSLSSNGNVTESGCKECEELEEKNIKEFL

QSFVHIVQMFINTS

In some cases, the leader peptide is cleaved from the intact polypeptide to generate the mature form that may be soluble or secreted.

The IL-18/IL-15RαSu/Fc and IL-12/IL-15N72D constructs were cloned into expression vectors as described previously (U.S. Pat. No. 8,507,222, at Example 1, incorporated herein by reference), and the expression vectors were transfected into CHO cells. Co-expression of the two constructs in CHO cells allowed for formation and secretion of the soluble IL-12/IL-15N72D:IL-18/IL-15RαSu/Fc fusion protein complex (referred to as hIL12/IL18/TxM), which can be purified by Protein A affinity and other chromatography methods.

3) Similar fusion protein complexes could be generated comprising IL-18/IL-15RαSu/Fc and IL-18/IL-15N72D fusion proteins or comprising IL-12/IL-15RαSu/Fc and IL-12/IL-15N72D fusion proteins. "Two headed" fusion protein complexes could be generated comprising IL-18/IL-15RαSu/Fc and IL-15N72D fusion proteins or IL-15RαSu/Fc and IL-18/IL-15N72D fusion proteins (FIG. 1B). Similarly, "two headed" fusion protein complexes could be generated comprising IL-12/IL-15RαSu/Fc and IL-15N72D fusion proteins or IL-15RαSu/Fc and IL-12/IL-15N72D fusion proteins. Such complexes were generated as described above.

Figure 4A:
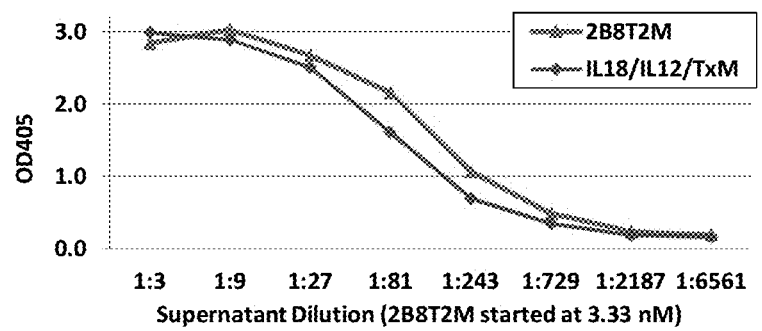
FIG. 4A is a line graph showing the binding activity of the hIL18/IL12/TxM fusion protein complex to antibodies specific to human IL-15 and human IgG.
Figure 4B:
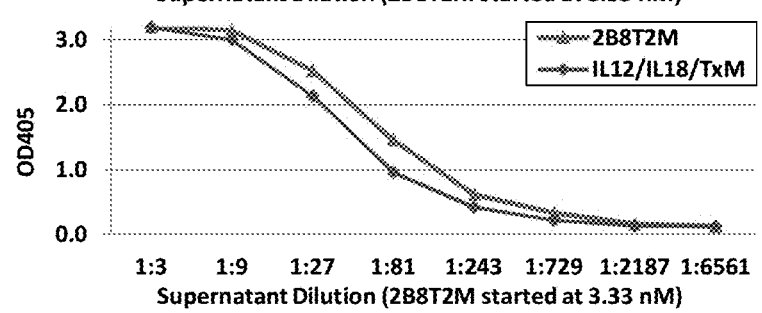
FIG. 4B is a line graph showing the binding activity of the hIL12/IL18/TxM fusion protein complex to antibodies specific to human IL-15 and human IgG.
Figure 4C:
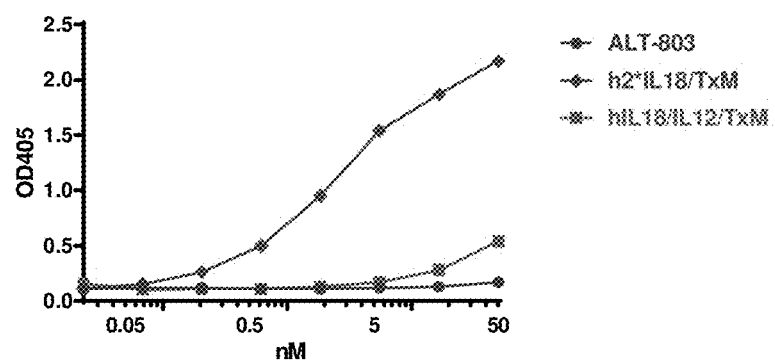
FIG. 4C is a line graph showing the binding activity of the two headed IL18/TxM fusion protein complex to antibodies specific to human IL-15 and human IL-18. Controls include anti-CD20 TxM (2B8T2M), ALT-803 and hIL12/IL18/TxM depending on the assay format.

Example 2: In Vitro Characterization of the Activities of hIL18/IL12/TxM and hIL12/IL18/TxM Fusion Protein Complexes ELISA-based methods confirmed the formation of the hIL18/IL12/TxM and hIL12/IL18/TxM fusion protein complexes. In FIG. 4A, the IL-18/IL-15N72D:IL-12/IL-15RαSu/Fc fusion protein complexes in the culture supernatant from transfected CHO cells were detected using a huIgG1/IL15-specific ELISA with a capture antibody, anti-human IL-15 antibody (MAB647, R&D Systems) and a detection antibody, horseradish peroxidase conjugated. This is compared to a similar antibody TxM fusion protein complex (2B8T2M) with a known concentration. The signal from the hIL18/IL12/TxM fusion protein complex can be compared to that of the 2B8 T2M control to estimate the fusion protein concentration. Similar results were obtained from hIL12/IL18/TxM fusion protein complexes (FIG. 4B). For the purified "two-headed" IL-18/TxM complex, an ELISA with anti-IL-18 Ab capture and anti-IL-15 Ab detection verified formation of the fusion proteins complex (FIG. 4C). The results from these assays demonstrate that soluble L-18/IL-15N72D, IL-12/IL-15RαSu/Fc, IL-12/IL-15N72D and IL-18/IL-15RαSu/Fc proteins can be produced in CHO cells and the hIL18/IL12/TxM and hIL12/IL18/TxM fusion protein complexes can form and be secreted into the culture media.

Figure 5:
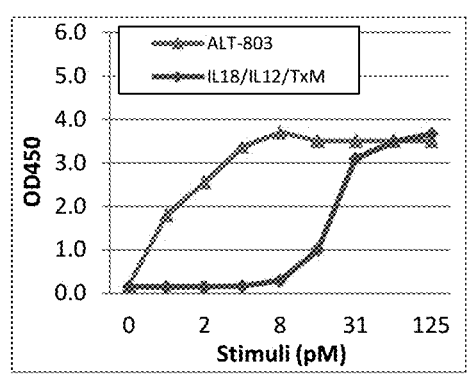
FIG. 5 is a line graph illustrating the proliferation of IL-15-dependent 32Dβ cells mediated by hIL18/IL12/TxM fusion protein complex compared to ALT-803.

To assess the IL-15 immunostimulatory activity of the hIL18/IL12/TxM fusion protein complexes, proliferation of IL-15-dependent 32Dβ cells, a mouse hematopoietic cell line, was assessed. Increasing levels of hIL18/IL12/TxM were added to 32Dβ cells ($10^4$ cell/well) in 200 μL RPMI: 10% FBS media and cells were incubated for 2 days at 37° C. WST-1 proliferation reagent (10 μL/well) then was added. After 4 hours, absorbance was measured at 450 nm to determine cell proliferation based on cleavage of WST-1 to a soluble formazan dye by metabolically active cells. The bioactivity of the L-15N72D:IL-15RαSu/Fc complex (ALT-803) was assessed as a positive control. As shown in FIG. 5, hIL18/IL12/TxM was able to promote cell proliferation of 32Dβ cells, thereby demonstrating IL-15 activity. The activity of hIL18/IL12/TxM was reduced compared to that of ALT-803, possibly due to the linkage of IL-18 to the IL-15N72D domain.

Figure 6:
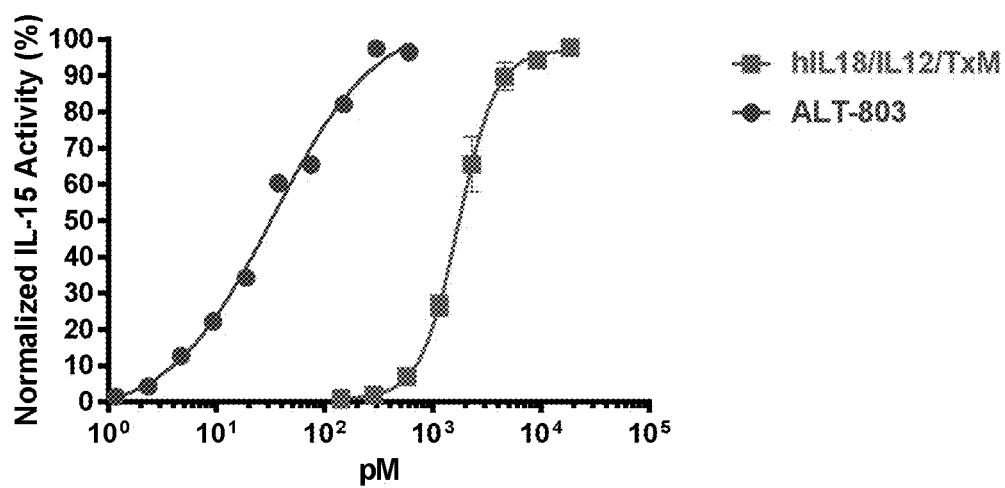
FIG. 6 is a line graph further illustrating the proliferation of IL-15-dependent 32Dβ cells mediated by hIL18/IL12/TxM fusion protein complex compared to ALT-803.

To further assess the IL-15 activity of hIL18/IL12/TxM, increasing concentrations of hIL18/IL12/TxM were added to 32Dβ cells ($10^4$ cells/well) in 200 μL IMDM:10% FBS media and incubated for 3 days at 37° C. PrestoBlue cell viability reagent (20 μL/well) then was added. After 4 hours, absorbance was measured at 570 nm (with a 600 nm reference wavelength for normalization) to determine cell proliferation based on reduction of PrestoBlue, a resazurin-based solution, by metabolically active cells. The half maximal effective concentration ($EC_{50}$) of IL-15 bioactivity for hIL18/IL12/TxM was then determined based on the relationship between absorbance and protein concentration. The bioactivity of ALT-803 was assessed as a positive control. As shown in FIG. 6, hIL18/IL12/TxM was able to promote cell proliferation of 32Dβ cells, thereby demonstrating IL-15 activity. The activity of hIL18/IL12/TxM was reduced compared to that of ALT-803, possibly due to the linkage of IL-18 to IL-15N72D.

Figure 7:
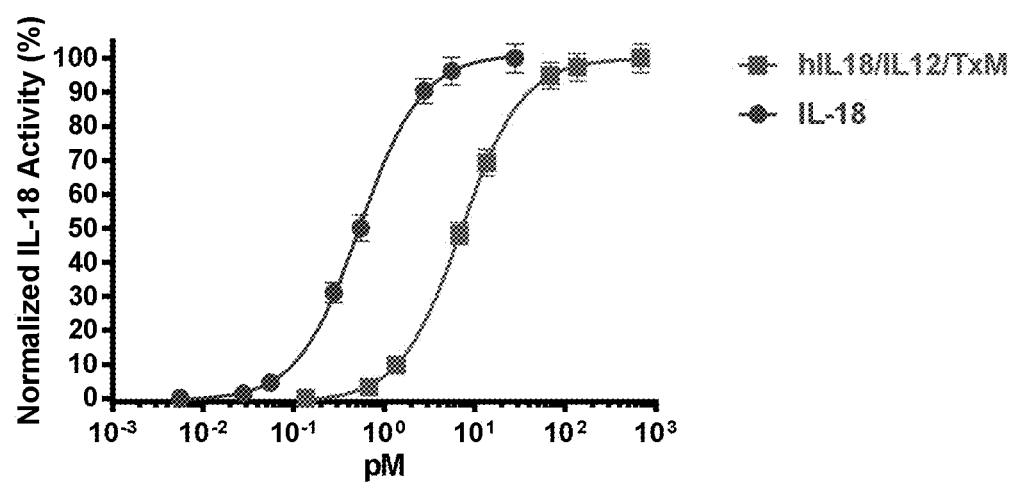
FIG. 7 is a line graph further illustrating the activation of IL-18-sensitive HEK18 reporter cells mediated by hIL18/IL12/TxM fusion protein complex compared to IL-18.

To assess the IL-18 activity of hIL18/IL12/TxM, activation of IL-18 reporter HEK-Blue IL-18 (HEK18) cells was assessed. Increasing concentrations of hIL18/IL12/TxM were added to HEK18 cells ($5\times10^4$ cells/well) in 200 μL IMDM:10% FBS HEK-Blue media and incubated for 20-22 hours at 37° C. Culture supernatant (20 μL/well) was then added to QUANTI-Blue reagent (180 μL/well). After 20 hours, absorbance was measured at 650 nm to determine cell activation based on reduction of QUANTI-Blue, a secreted embryonic alkaline phosphatase (SEAP) detection reagent. The half maximal effective concentration ($EC_{50}$) of IL-18 bioactivity of hIL18/IL12/TxM was then determined based on the relationship between absorbance and protein concentration. The bioactivity of recombinant IL-18 was assessed as a positive control. As shown in FIG. 7, hIL18/IL12/TxM was able to activate HEK18 cells, thereby demonstrating IL-18 activity. The activity of hIL18/IL12/TxM was reduced compared to that of recombinant IL-18, possibly due to the linkage of IL-18 to IL-15N72D.

Figure 8:
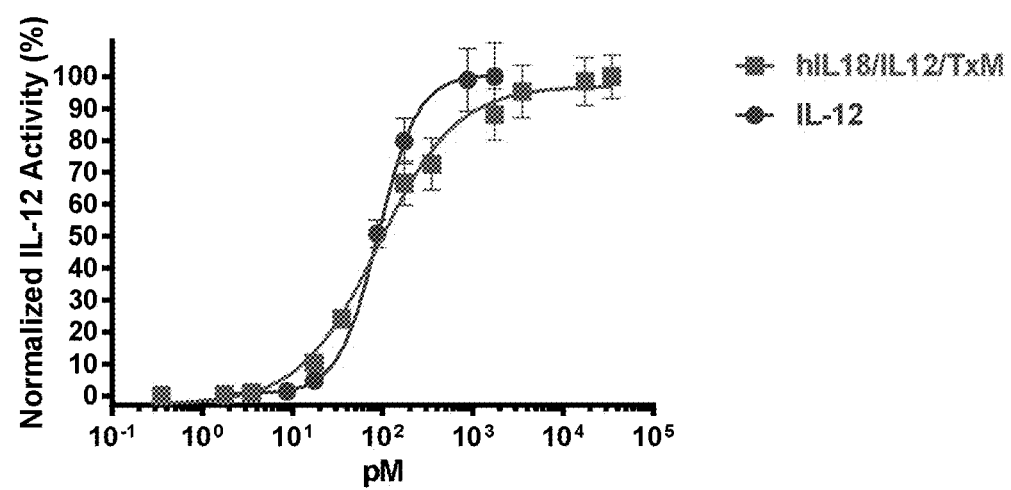
FIG. 8 is a line graph further illustrating the activation of IL-12-sensitive HEK12 reporter cells mediated by hIL18/IL12/TxM fusion protein complex compared to IL-12.
Figures 9A, 9B, 9C, 9D, 9E, 9F:
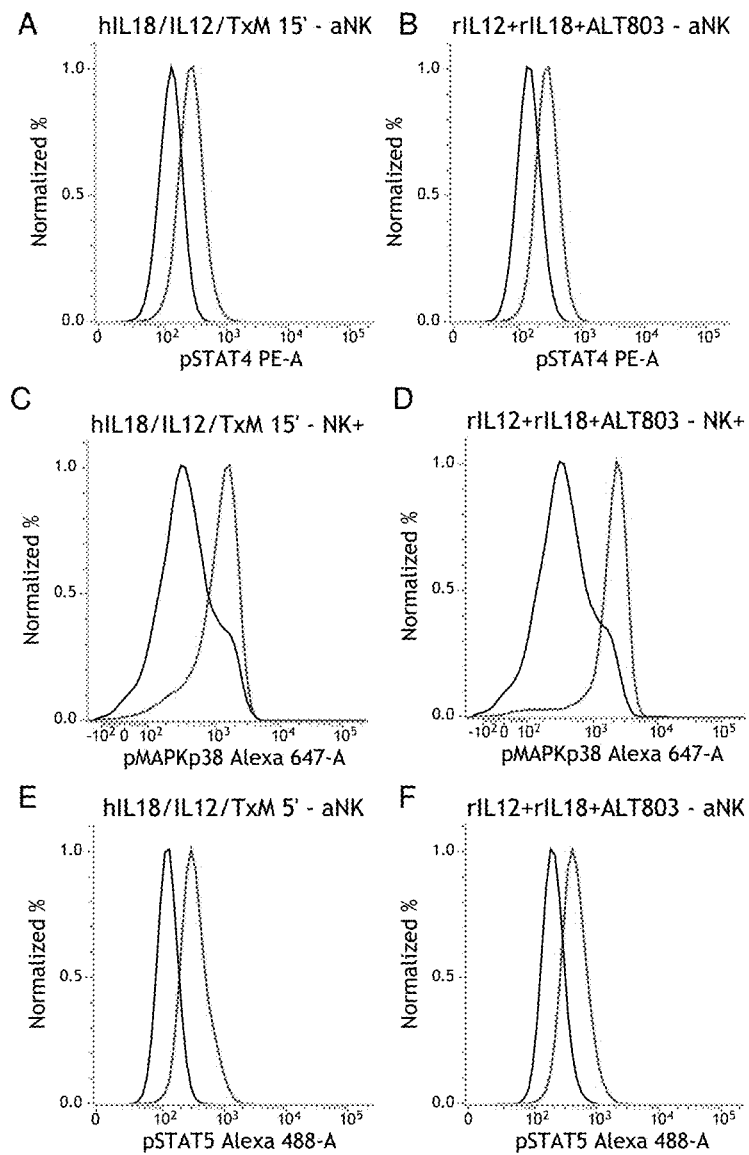
FIGS. 9A and 9B are line graphs showing IL-12 biological activity of hIL18/IL12/TxM (FIG. 9A) or a combination of recombinant IL-12, IL-18 and ALT-803 (rIL12+rIL18+ALT-803) (FIG. 9B) (red lines) compared to media control (black lines) in stimulating phosphorylation of STAT4 in aNK cells.
FIGS. 9C and 9D are line graphs showing IL-18 biological activity of hIL18/IL12/TxM (FIG. 9A) or a combination of recombinant IL-12, IL-18 and ALT-803 (rIL12+rIL18+ALT-803) (FIG. 9B) (red lines) compared to media control (black lines) in stimulating phosphorylation of p38 MAPK in purified human NK cells.
FIGS. 9E and 9F are line graphs showing IL-15 biological activity of hIL18/IL12/TxM (FIG. 9A) or a combination of recombinant IL-12, IL-18 and ALT-803 (rIL12+rIL18+ALT-803) (FIG. 9B) (red lines) compared to media control (black lines) in stimulating phosphorylation of STAT5 in aNK cells.

To assess the IL-12 activity of hIL18/IL12/TxM, activation of IL-12 reporter HEK-Blue IL-12 (HEK12) cells was assessed. Increasing concentrations of hIL18/IL12/TxM were added to HEK12 cells ($5\times10^4$ cells/well) in 200 μL IMDM:10% FBS HEK-Blue media and incubated for 20-22 hours at 37° C. Culture supernatant (20 μL/well) was then added to QUANTI-Blue reagent (180 μL/well). After 20 hours, absorbance was measured at 650 nm to determine cell activation based on reduction of QUANTI-Blue, a secreted embryonic alkaline phosphatase (SEAP) detection reagent. The half maximal effective concentration ($EC_{50}$) of IL-12 bioactivity of hIL18/IL12/TxM was then determined based on the relationship between absorbance and protein concentration. The bioactivity of recombinant IL-12 was assessed as a positive control. As shown in FIG. 8, hIL18/IL12/TxM was able to activate HEK12 cells, similar to recombinant IL-12, thereby demonstrating IL-12 activity.

In order to further demonstrate the individual activity of each cytokine (IL-12, IL-18, and IL-15), flow cytometry-based intracellular phosphoprotein assays were developed utilizing proteins that are uniquely phosphorylated in response to receptor signaling by each cytokine (IL-12: STAT4, IL-18: p38 MAPK, and IL-15: STAT5). Following short term stimulation (5-15 minutes) of NK92 (aNK) cells or purified human NK cells (>95% CD56+) with 1 μg/ml hIL18/IL12/TxM resulted in similar responses to that seen with the optimal combinations of recombinant IL-12 (10 ng/ml), IL-18 (50 ng/ml) and ALT-803 (50 ng/ml IL-15 activity) (FIG. 9A-F). These results demonstrate that each of the cytokine domains of the hIL18/IL12/TxM fusion protein complex retains its specific immunostimulatory biological activity.

Figure 10A:
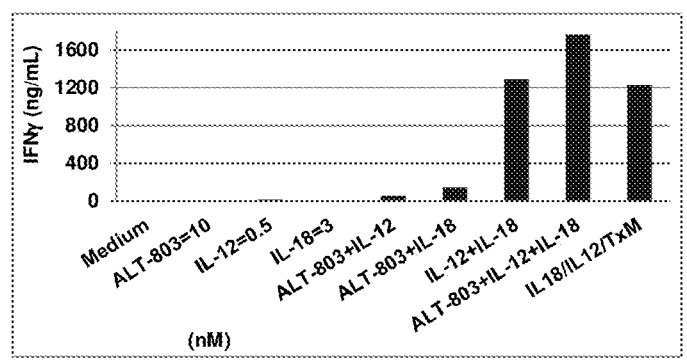
FIG. 10A is a bar chart illustrating the combined cytokine immunostimulatory activity of hIL18/IL12/TxM fusion protein complex compared to cytokines alone or in combination to induce IFN-γ production by aNK cells.
Figure 10B:
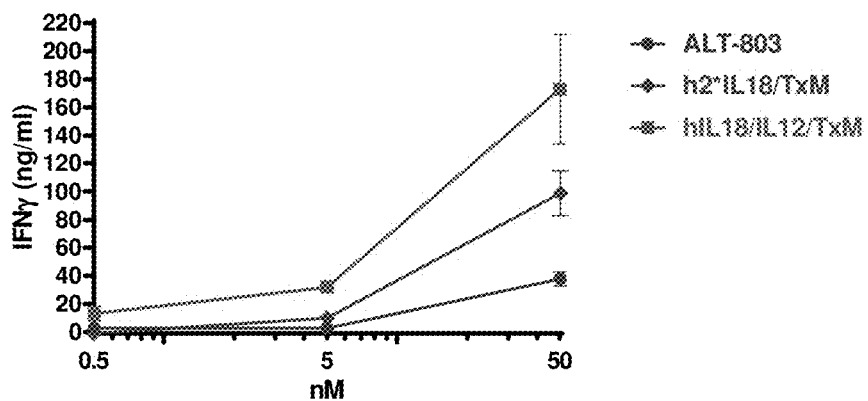
FIG. 10B is a line graph illustrating the cytokine immunostimulatory activity of two headed IL18/TxM fusion protein complex compared to ALT-803 or hIL18/IL12/TxM to induce IFN-γ production by aNK cells.
Figures 11A, 11B, 11C, 11D, 11E, 11F:
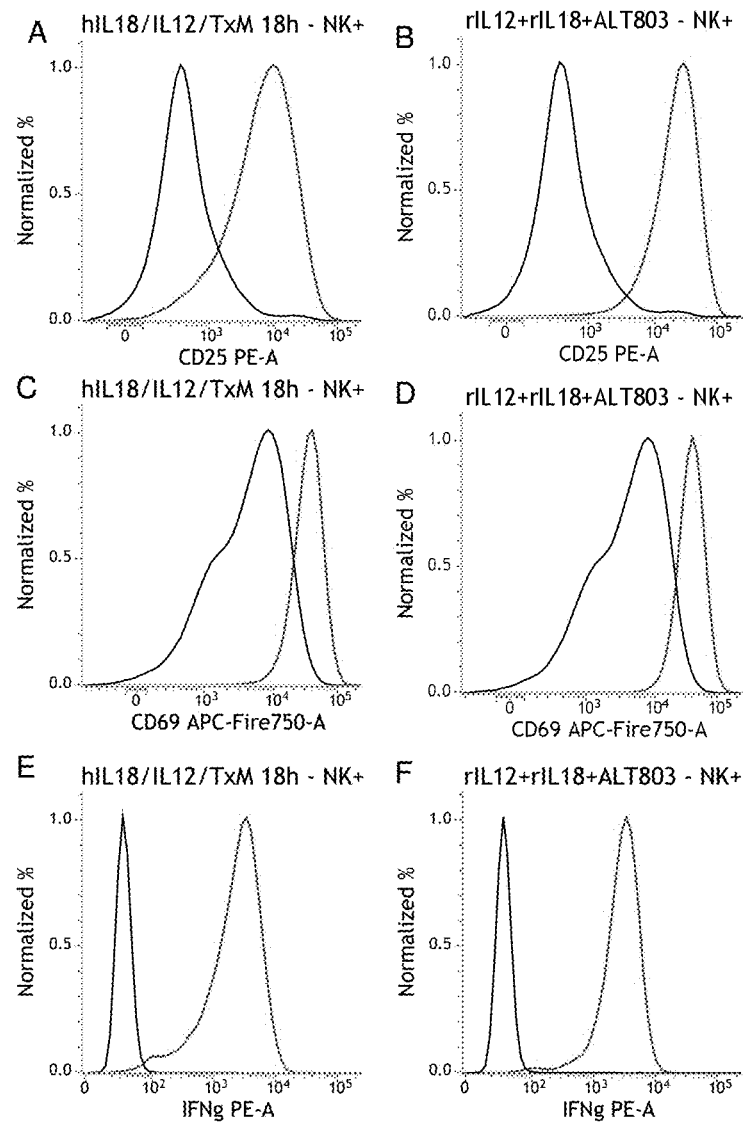
FIGS. 11A and 11B are line graphs showing biological activity of hIL18/IL12/TxM (FIG. 11A) or a combination of recombinant IL-12, IL-18 and ALT-803 (rIL12+rIL18+ALT-803) (FIG. 11B) (red lines) compared to media control (black lines) for inducing CD25 by purified human NK cells.
FIGS. 11C and 11D are line graphs showing biological activity of hIL18/IL12/TxM (FIG. 11A) or a combination of recombinant IL-12, IL-18 and ALT-803 (rIL12+rIL18+ALT-803) (FIG. 11B) (red lines) compared to media control (black lines) for inducing CD69 by purified human NK cells.
FIGS. 11E and 11F are line graphs showing biological activity of hIL18/IL12/TxM (FIG. 11A) or a combination of recombinant IL-12, IL-18 and ALT-803 (rIL12+rIL18+ALT-803) (FIG. 11B) (red lines) compared to media control (black lines) for inducing intracellular IFN-γ by purified human NK cells.

It is known that the combination of IL-12, IL-18 and IL-15 activity is more effective at inducing IFN-γ production by NK cells than any of these cytokines alone. In order to evaluate the combined cytokine activity of the hIL18/IL12/TxM complex, aNK cells were incubated with hIL18/IL12/TxM complex (50 nM), combinations of IL-12 (0.5 nM), IL-18 (3 nM), and ALT-803 (10 nM), or each cytokine alone. After 2 days, IFN-γ levels in the culture supernatants were determined with ELISA methods. As shown in FIG. 10A, IL-12, IL-18 and ALT-803 alone had little effect on aNK cells whereas combinations of IL-12+ALT-803 and IL-18+ALT-803 induced low level production of IFN-γ by aNK cells. However, hIL18/IL12/TxM fusion protein complex alone and combinations of IL-12+IL-18 and IL-12+IL-18+ALT-803 exhibited high level production of IFN-γ by aNK cells. These results verify that hIL18/IL12/TxM fusion protein complex exhibit the expected immunostimulatory activity of the combined IL-12, IL-18 and IL-15 cytokines. Similar studies with the "two headed" IL-18/TxM complex demonstrated the ability of this complex to induce IFN-γ by aNK cells but to a lesser degree than hIL18/IL12/TxM fusion protein complex (FIG. 10B).

Example 3: Induction of Cytokine Induced Memory Like NK Cells by hIL18/IL12/TxM Fusion Protein Complexes Previous studies have shown that cytokine induced memory like NK cells can be induced ex vivo following overnight stimulation of purified NK cells with saturating amounts of IL-12 (10 ng/ml), IL-15 (50 ng/ml), and IL-18 (50 ng/ml). These cells exhibit memory-like properties such as 1) enhanced proliferation, 2) expression of IL-2 receptor α (IL-2Rα, CD25) and other activation markers, and 3) increased IFN-γ production. To evaluate the ability of hIL18/IL12/TxM to promote generation of cytokine induced memory like NK cells, purified human NK cells (>95% CD56+) (5×10$^6$ cells/ml) were stimulated for 18 hours with 1 μg/ml hIL18/IL12/TxM or the optimal combination of recombinant IL-12 (10 ng/ml), IL-18 (50 ng/ml), and ALT-803 (50 ng/ml IL-15 activity). Induction of cytokine induced memory like cells was assessed as increased cell-surface CD25 and CD69 (stimulation marker) expression and intracellular IFN-γ levels as determined by antibody-staining and flow cytometric methods. The results indicated that hIL18/IL12/TxM fusion protein complex was capable of inducing CD25, CD69 and intracellular IFN-γ to a similar extent as the optimal combination of IL-12, IL-18 and IL15 following overnight incubation with human NK cells (FIG. 11A-FIG. 11F). Thus, overnight incubation with hIL18/IL12/TxM fusion protein complexes can generate cytokine induced memory like NK cells.

Figure 12A:
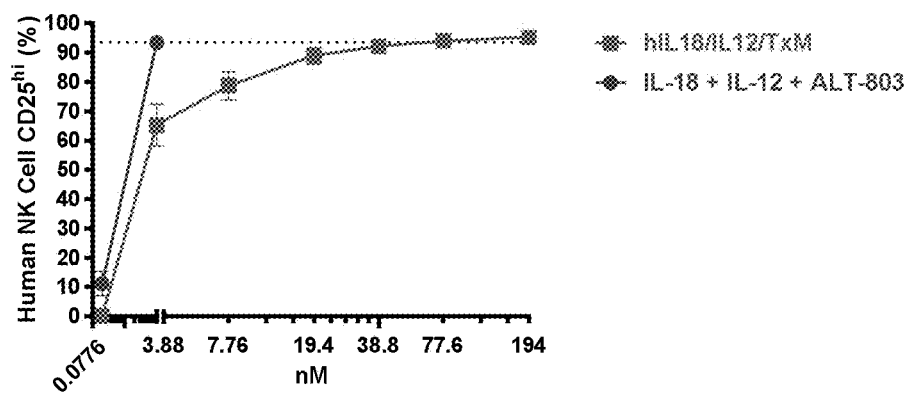
FIG. 12A is a line graph illustrating the induction of the activation marker CD25 on the surface of human NK cells mediated by hIL18/IL12/TxM fusion protein complex compared to IL-18+IL-12+ALT-803.
Figure 12B:
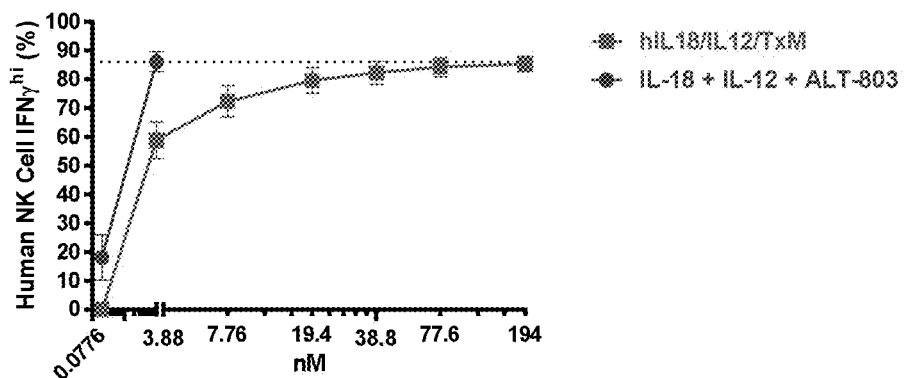
FIG. 12B is a line graph illustrating the induction of intracellular IFN-γ in human NK cells mediated by hIL18/IL12/TxM fusion protein complex compared to IL-18+IL-12+ALT-803.

Previous studies have shown that cytokine-induced memory-like NK cells can be induced ex vivo following overnight stimulation of purified NK cells with saturating amounts of IL-12 (10 ng/ml), IL-15 (50 ng/ml), and IL-18 (50 ng/ml). These cells exhibit memory-like properties such as 1) enhanced proliferation, 2) expression of IL-2 receptor α (IL-2Rα, CD25), 3) increased IFNγ production, and 4) augmented cytotoxicity mediated by perforin and granzymes. To evaluate the ability of hIL18/IL12/TxM to promote generation of cytokine-induced memory-like NK cells, purified human NK cells (>95% CD56+, 5×10$^6$ cells/ml) were stimulated for 12-18 hours with increasing concentrations of hIL18/IL12/TxM or the optimal combination of recombinant IL-12 (10 ng/ml), IL-18 (50 ng/ml), and ALT-803 (50 ng/ml IL-15, 3.88 nM). Induction of a pre-activated cytokine-induced memory-like cell phenotype was assessed as increased cell surface CD25 expression and intracellular IFNγ levels as determined by antibody staining and flow cytometric methods. As shown in FIGS. 12A and 12B, hIL18/IL12/TxM was capable of inducing CD25 and intracellular IFNγ to a similar extent as the optimal combination of IL-12, IL-18, and ALT-803 following overnight incubation with human NK cells.

Figure 13A:
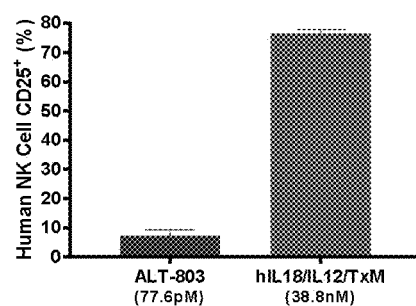
FIG. 13A is a bar chart illustrating maintenance of CD25 on the surface of human CIML NK cells induced by priming with hIL18/IL12/TxM fusion protein complex (compared to ALT-803) followed by resting in ALT-803.
Figure 13B:
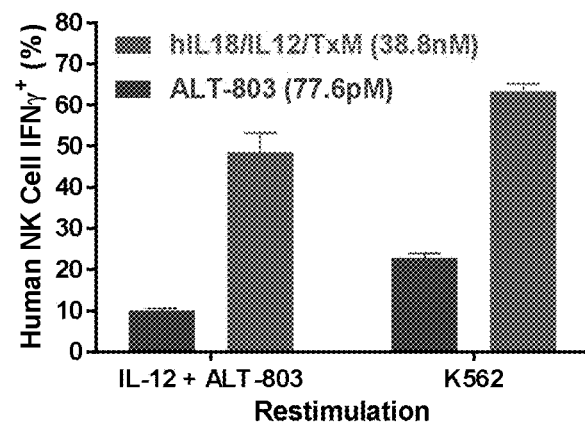
FIG. 13B is a bar chart illustrating enhanced levels of intracellular IFN-γ in human CIML NK cells induced by priming with hIL18/IL12/TxM fusion protein complex (compared to ALT-803) followed by resting in ALT-803 and restimulation with IL-12+ALT-803 or K562 leukemia targets.

In order to demonstrate generation of cytokine induced memory like NK cells by hIL18/IL12/TxM, primary human NK cells (2×10$^6$/ml) were primed for 16 hours as above with hIL18/IL12/TxM (38.8 nM), washed, and rested in low dose ALT-803 (77.6 pM, equivalent to 1 ng/ml IL-15) for 6 days, to allow the primed NK cells to differentiate into cytokine induced memory like NK cells. Maintenance of CD25 expression and enhanced IFN-γ production following 6 hour re-stimulation with cytokines (IL-12 (10 ng/ml) and ALT-803 (50 ng/ml IL-15 equivalent)) or leukemia targets (K562 cells, 5:1 ratio), in the presence of brefeldin A and monensin, were assessed as correlates for generation of cytokine induced memory like NK cells. In all cases, priming with hIL18/IL12/TxM, compared to low dose IL-15 (77.6 pM ALT-803) as a control, resulted in enhanced levels of CD25 (FIG. 13A) and increased expression of IFN-γ following re-stimulation with both cytokines and leukemia targets (FIG. 13B).

Figure 14A:
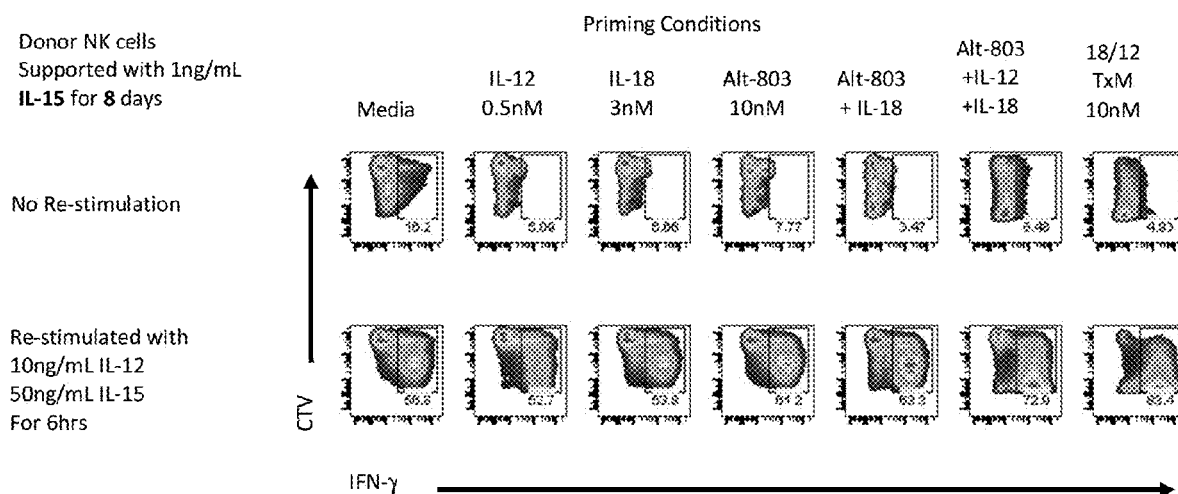
FIG. 14A show contour plots illustrating proliferation (CTV dilution) and IFN-γ expression in human CIML NK cells induced by priming with hIL18/IL12/TxM fusion protein complex, individual cytokines or IL-18+IL-12+ALT-803 followed by resting in IL-15 and restimulation with IL-12+ALT-803 compared to no restimulation.
Figure 14B:
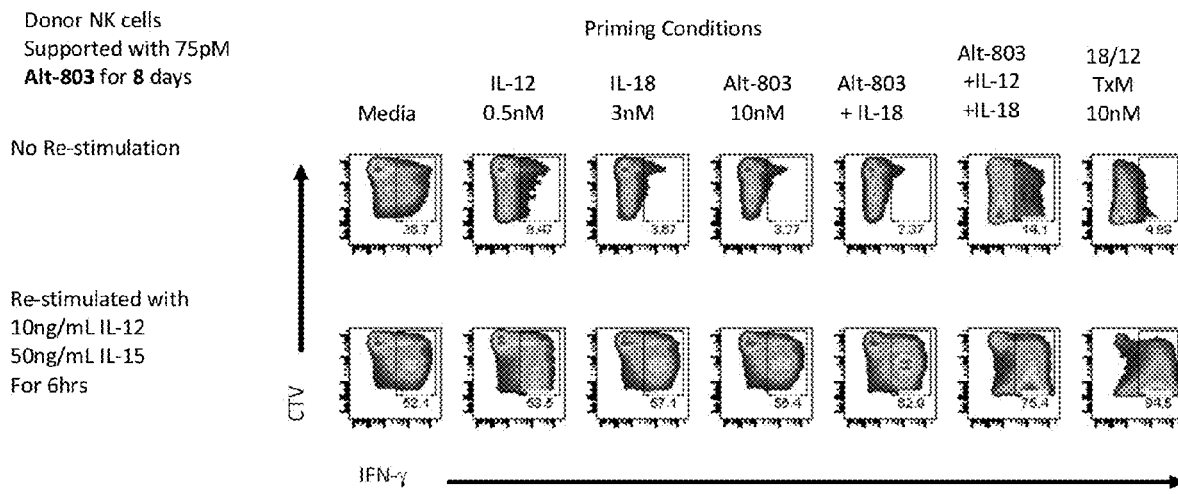
FIG. 14B show contour plots illustrating proliferation (CTV dilution) and IFN-γ expression in human CIML NK cells induced by priming with hIL18/IL12/TxM fusion protein complex, individual cytokines or IL-18+IL-12+ALT-803 followed by resting in ALT-803 and restimulation with IL-12+ALT-803 compared to no restimulation.
Figure 15:
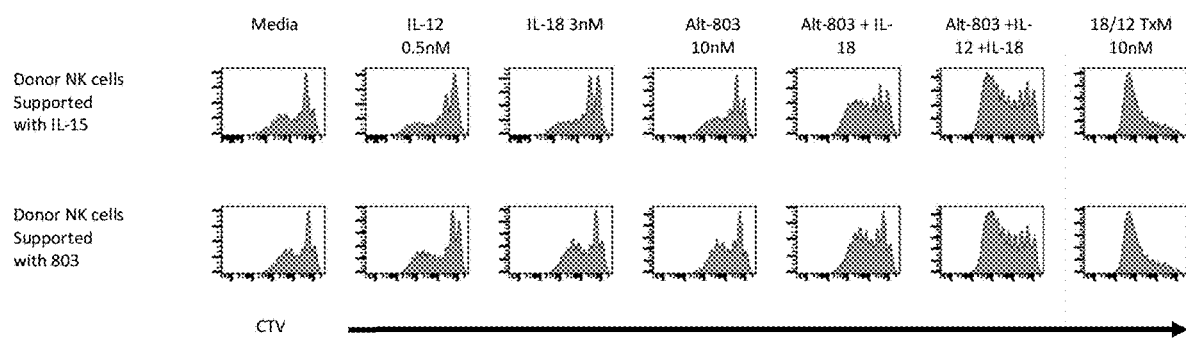
FIG. 15 show histogram plots illustrating proliferation (CTV dilution) in human CIML NK cells induced by priming with hIL18/IL12/TxM fusion protein complex, individual cytokines or IL-18+IL-12+ALT-803 followed by resting in IL-15 or ALT-803 and restimulation with IL-12+ALT-803.

Similar studies were conducted to further compare the effects of short-term priming with hIL18/IL12/TxM or different cytokine combinations on human NK cell that were subsequently rested in low dose ALT-803 or IL-15 and restimulated with IL-12 and IL-15. For these studies, proliferation and IFN-γ production of the CIML NK cells was assessed as a measure of immune activation. As shown in FIGS. 14A and B, human NK cells were labeled with CellTrace Violet and primed as above with media alone, IL-12 (0.5 nM), IL-18 (3 nM), ALT-803 (10 nM), ALT-803 (10 nM)+IL-18 (3 nM), ALT-803 (10 nM)+IL-18 (3 nM)+IL-12 (0.5 nM), or hIL18/IL12/TxM (10 nM). Following priming, the cells were washed and maintained in media containing 1 ng/mL IL-15 (FIG. 14A) or 75 pM ALT-803 (FIG. 14B) followed by no re-stimulation or restimulation with 10 ng/mL IL-12+50 ng/mL IL-15. The proliferation of the CIML NK cells was determined by dilution of the CellTrace Violet label and intracellular IFN-γ expression was determined by intracellular staining and flow cytometry. Compared to no priming or priming with individual cytokines, ALT-803+IL-18, or ALT-803+IL-18+IL-12, NK cells expressed higher levels of intracellular IFN-γ following priming with hIL18/IL12/TxM and subsequent resting in IL-15 or ALT-803 then restimulation with IL-12+IL-15. Specifically, >83% of the CIML NK cells generated by priming with hIL18/IL12/TxM were found to express IFN-γ following restimulation compared to ~74% of the NK cells primed with the standard hIL18+IL12+ALT-803 combination and 50%-60% of the NK cells primed with individual cytokines. CIML NK cells primed with hIL18/IL12/TxM also showed greater proliferation as measured by CellTrace Violet dilution than NK cells primed with hIL188+IL12+ALT-803 or the individual cytokines (FIG. 15). There results confirm that short-term priming of human NK cells with hIL18/IL12/TxM can result in an CIML NK cell (i.e., increased proliferation and immune activation (CD25, IFN-γ expression)) equivalent or better than priming with hIL18+IL12+IL-15.

Figure 16:
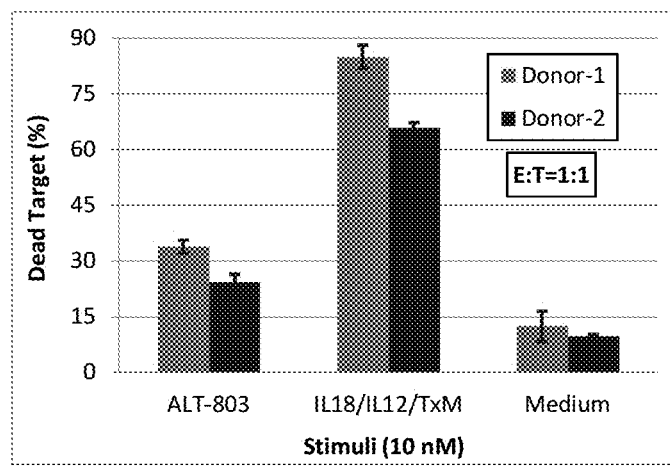
FIG. 16 is a bar chart illustrating the cytotoxicity of human NK cells against MDA-MB-231 human breast cancer cells induced by hIL18/IL12/TxM fusion protein complex or ALT-803 (IL-15N72D:IL-15R(x/Fc complex).

Additionally, the effect of hIL18/IL12/TxM fusion protein complexes on cytotoxicity of human NK cells against human tumor cells was investigated. Human breast cells (MDA-MB-231) (Celltrace violet labelled) were incubated with purified human NK cells (2 independent donors; NK1 and NK2) (E:T ratio; 1:1) in the presence of hIL18/IL12/TxM complex (10 nM) or ALT-803 (10 nM) as a control. After 2 days, the percentage of dead tumor cells (Violet$^+$ PI$^+$) was assessed by flow cytometry following staining with propidium iodide (PI). As shown in FIG. 16, hIL18/IL12/TxM induced significantly more effective human NK cell cytotoxicity against breast tumor cells than ALT-803. These results are consistent with the ability of IL-12, IL-18 and IL-15 combination treatment to enhance anti-tumor NK cell activity.

Figure 17A:
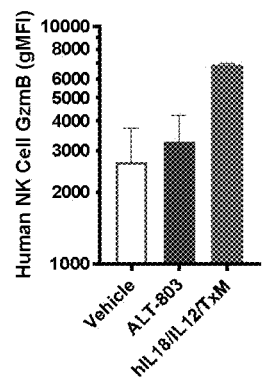
FIG. 17A is a bar graph illustrating the induction of intracellular granzyme B in human NK cells mediated by hIL18/IL12/TxM fusion protein complex compared to ALT-803 or no treatment.
Figure 17B:
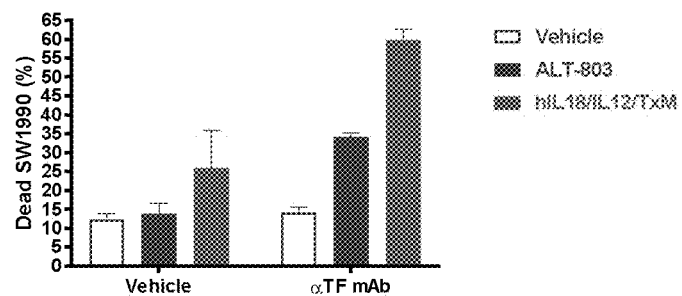
FIG. 17B is a bar graph illustrating direct cytotoxicity (vehicle bars) or antibody dependent cellular cytotoxicity (αTF Ab bars) of human NK cells against Tissue Factor-positive SW1990 human pancreatic adenocarcinoma cells following priming with hIL18/IL12/TxM fusion protein complex compared to media alone or ALT-803.
Figure 17C:
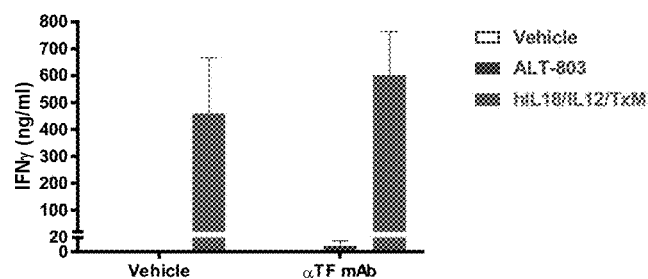
FIG. 17C is a bar graph illustrating increased expression of IFN-γ by human NK cells incubated with SW1990 human pancreatic adenocarcinoma cells with anti-TF Ab or media alone (vehicle) following priming with hIL18/IL12/TxM fusion protein complex compared to media alone or ALT-803.

The hIL18/IL12/TxM fusion protein complexes were also able to augment expression of granzyme B in human NK cells, as compared to ALT-803 or no treatment (FIG. 17A). Furthermore, these hIL18/IL12/TxM activated NK cells were also more effective in direct or antibody-mediated cytotoxicity assays against a human tumor target (FIG. 17B), including enhanced production of IFNγ (FIG. 17C). Thus, overnight incubation with hIL18/IL12/TxM can generate a phenotype associated with cytokine-induced memory-like NK cells.

Example 4: Antitumor Activities of Immune Cells Stimulated by hIL18/IL12/TxM Fusion Protein Complexes The ability of hIL18/IL12/TxM fusion protein complexes to induce cytokine induced memory like NK cells with in vivo antitumor activity will be assessed. Splenic NK cells will be isolated from mice by standard methods and stimulated at 5×10$^6$ cells/ml for 18 hours with 1 μg/ml hIL18/IL12/TxM, a combination of recombinant IL-12 (10 ng/ml), IL-18 (50 ng/ml), and ALT-803 (50 ng/ml IL-15 activity) or ALT-803 alone (50 ng/ml IL-15 activity). The cells will then be washed and adoptively transferred (1×10$^6$ cells/mouse) i.v. into C57BL/6 mice that bear subcutaneous RMA-S lymphoma and received 5 Gy of total body radiation 3 hours prior to cell transfer. Survival of mice will be monitored. Tumor-bearing mice treated with IL-12+IL-18+ALT-803-activated NK cells (CIML NK cells) are expected to survival longer that mice treated with ALT-803-activated NK cells (Ni, J, et al. J. Exp. Med. 2012 209:2351-2365). Prolonged survival of tumor-bearing mice receiving hIL18/IL12/TxM-activated NK cells will provide evidence that hIL18/IL12/TxM can serve as an ex-vivo agent to augment in vivo antitumor activity of immune cells.

Similarly, purified human NK cells will be stimulated at 5×10$^6$ cells/ml for 18 hours with 1 μg/ml hIL18/IL12/TxM, a combination of recombinant IL-12 (10 ng/ml), IL-18 (50 ng/ml), and ALT-803 (50 ng/ml IL-15 activity) or ALT-803 alone (50 ng/ml IL-15 activity). The cells will then be washed and adoptively transferred (1×10$^6$ cells/mouse) i.v. into NSG mice that bear K562 leukemia cells and received low-dose rhIL-2 post cell transfer. Survival of mice will be monitored. Tumor-bearing mice treated with IL-12+IL-18+ALT-803-activated NK cells (CIML NK cells) are expected to survival longer that mice treated with ALT-803-activated NK cells (Romee, R, et al. Sci Transl Med. 2016; 8:357ra123). Prolonged survival of tumor-bearing mice receiving hIL18/IL12/TxM-activated human NK cells will provide evidence that hIL18/IL12/TxM can serve as an ex-vivo agent to augment in vivo antitumor activity of immune cells.

For treatment of patients with malignancies such as relapsed or refractory acute myeloid leukemia (AML) (Romee, R, et al. Sci Transl Med. 2016; 8:357ra123), patients will be treated with preconditioned with cyclophosphamide and fludarabine and then treated with CIML NK cells which were generated from allogeneic haploidentical NK cells incubated ex vivo with hIL18/IL12/TxM or hIL12/IL18/TxM for 16 to 24 hours. Following cell transfer, patients may receive low dose IL-2 to support the cells in vivo. Antitumor responses (objective responses, progression free survival, overall survival, time to relapse, etc.) will be assessed and will provide evidence that hIL18/IL12/TxM or hIL12/IL18/TxM can serve as an ex-vivo agent to augment antitumor activity of human immune cells in patients with malignancies. Similar studies will be carried out in patients with other hematologic or solid tumor or infectious diseases.

In each of these studies, the persistence and functionality of the NK cells can be evaluated post transfer. For example, PBMCs could be isolated from patients 7 to 14 days post transfer and the percentage of Ki67-positive (proliferation marker) donor NK cells can be determined by flow cytometry. The NK cells can also be restimulated with tumor cells and the levels of IFN-γ production can be assessed by flow cytometry. The results of these studies will indicate if pre-transfer treatment of NK cells ex vivo with hIL18/IL12/TxM or hIL12/IL18/TxM augments their subsequent immune responses in vivo.

Figure 18A:
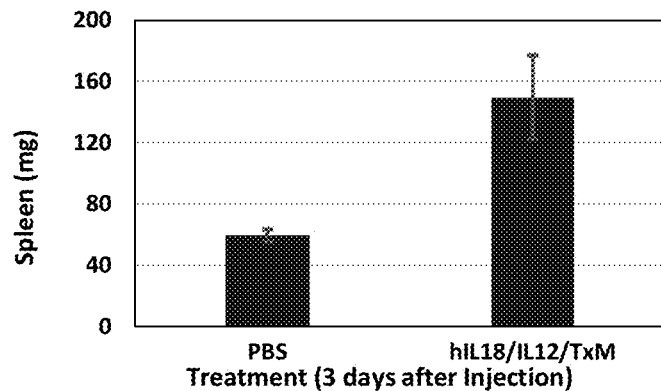
FIG. 18A is a bar graph showing changes in spleen weights following administration of hIL18/IL12/TxM (20 mg/kg) vs. PBS in C57BL/6 mice.
Figure 18B:
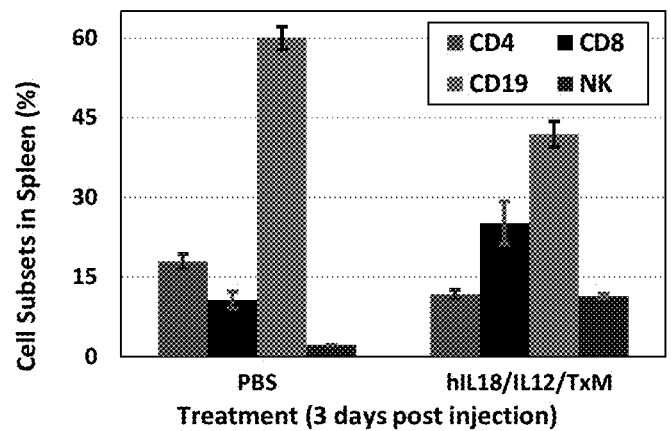
FIG. 18B is a bar graph showing changes in the percentage of CD8 T cells and NK cells in the spleen of C57BL/6 mice following administration of hIL18/IL12/TxM (20 mg/kg) compared to PBS controls.
Figure 18C:
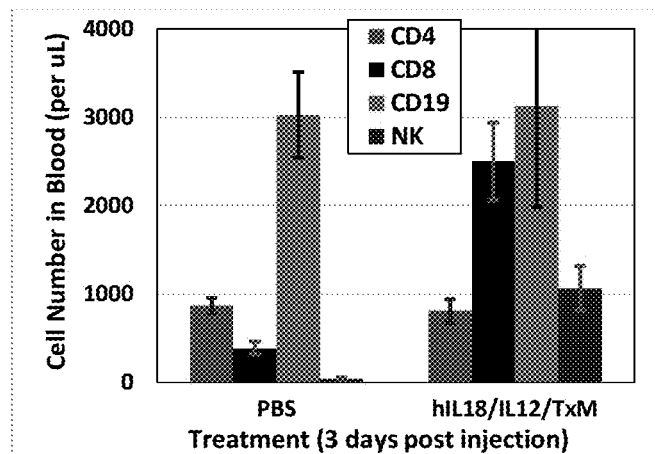
FIG. 18C is a bar graph showing changes in the absolute CD8 T cell and NK cell counts in the blood of C57BL/6 mice following administration of hIL18/IL12/TxM (20 mg/kg) compared to PBS controls.
Figure 18D:
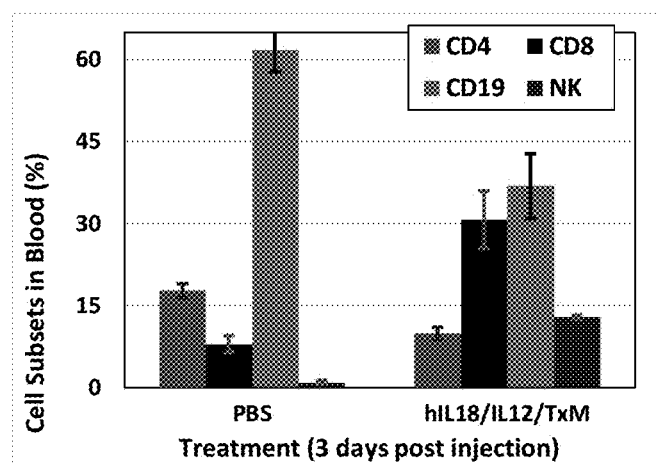
FIG. 18D is a bar graph showing changes in the percentage of CD8 T cells and NK cells in the blood of C57BL/6 mice following administration of hIL18/IL12/TxM (20 mg/kg) compared to PBS controls.

Example 5: Immunostimulatory Effects of hIL18/IL12/TxM Fusion Protein Complexes Following Administration to Mice As indicated above hIL18/IL122/TxM fusion protein complexes were highly effective at stimulating proliferation and responses of immune cells in vitro. To assess the activity of these complexes in vivo, female C57BL/6 mice were injected intraperitoneally with 20 mg/kg hIL18/IL12/TxM or PBS as a control. After 3 days, the mice were sacrificed and blood and spleen samples were taken to determine changes in immune cell subsets as measured by flow cytometry following staining with antibodies to CD8 T cells (CD8), CD4 T cells (CD4), B cells (CD19) and NK cells (NKp46). As shown in FIG. 18A, hIL18/IL12/TxM treatment resulted in a 2.5-fold increase in the weight of the spleens compared to PBS control treated mice. However, there were no signs of clinical toxicity with 20 mg/kg hIL18/IL12/TxM treatment. Administration of hIL18/IL12/TxM also resulted in a greater than 2-fold increase in the percentage of CD8 T cells and a 5.5-fold increase in the percentage of NK cells in the spleens of treated mice compared to the PBS controls (FIG. 18B). Additionally, absolute cell counts in the blood increased 6.4-fold for CD8 T cells and 23-fold for NK cells and blood cell percentages increased 3.9-fold for CD8 T cells and 13-fold for NK cells following treatment of mice with hIL18/IL12/TxM compared to PBS (FIG. 18C and FIG. 18D). The results of this study clearly indicate that administration of hIL18/IL12/TxM provided an immunostimulatory effect to immune cells, particularly CD8 T cells and NK cells, in mice without causing overt toxicity.

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. Genbank and NCBI submissions indicated by accession number cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims.

SEQUENCE LISTING

```
Sequence total quantity: 13
SEQ ID NO: 1          moltype = DNA  length = 2499
FEATURE               Location/Qualifiers
source                1..2499
                      mol_type = other DNA
                      organism = synthetic construct
SEQUENCE: 1
atgaagtggg tgaccttcat cagcctgctg ttcctgttct ccagcgccta ctccatctgg   60
gagctgaaga aagacgtgta tgtcgtggag ctggactggt atcctgacgc ccccggcgag  120
atggtggtgc tgacatgcga caccectgag gaggatggca tcacatggac cctggaccaa  180
agcagcgagg tgctgggctc cggaaagacc ctgaccatcc aggtgaagga gttcggcgac  240
gccgccagt  atacctgcca taagggaggc gaggtgctgt cccactccct gctcctgctg  300
cacaagaagg aagatggcat ctggagcacc gatattctga aggaccagaa ggagcccaag  360
aacaaaacct ttctgcggtg cgaggccaag aattattccg gcaggttcac ctgctggtgg  420
ctgaccacaa tctccaccga cctgaccttc agcgtcaaga gctccagggg atcctccgat  480
cctcagggcg tgacctgtgg agctgccacc ctgtccgctg agagggtgag gggcgacaac  540
aaggagtacg agtactccgt cgagtgtcag gaggactccg cctgccctgc tgccgaagag  600
agcctgccta tcgaagtcat ggtggacgcc gtgcacaacc tgaagtatga gaactacacc  660
agcagcttct tcatccggga cattatcaag cctgatcccc ctaagaacct ccagctcaag  720
cccctgaaga attcccggca agtcgaggtg tcctgggagt accccgacac ctggtccacc  780
cctcactcct attttagcct gaccttctgc gtgcaggtgc agggcaagag caagagggag  840
aagaaagacc gggtgttcac cgacaagacc agcgctaccg tgatctgtcg gaagaacgct  900
tccatttccg tgcgggctca ggacaggtat tactcctcct cctggtccga gtgggctagc  960
gtccctgca  gcggaggtgg cggatccgga ggtgaggtt ctggtggagg tgggagtagg  1020
aacctgcccg tggctacacc cgaccctgga atgttcccct gtctccacca cagccaaaac 1080
ctcctgcggg ccgtgtccaa catgctgcaa aaggctcggc agacactgga gttctacccc 1140
tgcaccagcg aggagatcga ccatgaggac atcacaaagg acaagacaag caccgtggag 1200
gcttgcctcc ccctggaact gaccaagaat gagtcctgcc tcaacagccg ggagacatcc 1260
ttcatcacca atggctcctg tctggcttcc cggaagacaa gcttcatgat ggcctgtgtc 1320
ctgtccagca tctatgagga cctgaagatg taccaggtcg agtttaagac catgaacgcc 1380
aagctgctga tggaccccaa gcggcaaatc ttcctggacc agaacatgct ggctgtgatc 1440
gacgagctga tgcaggctct gaacttcaac agcgagaccg tgcccagaa  gtcctccctg 1500
gaggagcctg attttacaa  gaccaaaatc aagctctgca tcctcctgca cgccttccgg 1560
atcagggccg tgaccatcga tcgggtgatg tcctacctga atgcttccat cacgtgtcct 1620
cctcctatgt ccgtggaaca cgcagacatc tgggtcaaga gctacagctt gtactccagg 1680
gagcggtaca tttgtaactc tggtttcaag cgtaaagccg gcacgtccag cctgacggag 1740
tgcgtgttga acaaggccac gaatgtcgcc cactggacaa cccccagtct caaatgcatt 1800
agagagccga aatcttgtga caaaactcac acatgcccac cgtgcccagc acctgaactc 1860
ctggggggac cgtcagtctt cctcttcccc ccaaaaccca aggacaccct catgatctcc 1920
cggacccctg aggtcacatg cgtggtggtg gacgtgagcc acgaagaccc tgaggtcaag 1980
ttcaactggt acgtggacgg cgtggaggtg cataatgcca agacaaagcc gcgggaggag 2040
cagtacaaca gcacgtaccg tgtggtcagc gtcctcaccg tcctgcacca ggactggctg 2100
aatggcaagg agtacaagtg caaggtctcc aacaaagccc tcccagcccc catcgagaaa 2160
accatctcca aagccaaagg gcagccccga gaaccacagg tgtacaccct gcccccatcc 2220
cgggatgagc tgaccaagaa ccaggtcagc ctgacctgcc tggtcaaagg cttctatccc 2280
agcgacatcg ccgtggagtg ggagagcaat gggcagccgg agaacaacta caagaccacg 2340
cctcccgtgc tggactccga cggctccttc ttcctctaca gcaagctcac cgtggacaag 2400
agcaggtggc agcagggaa  cgtcttctca tgctccgtga tgcatgaggc tctgcacaac 2460
cactacacgc agaagagcct ctccctgtct cctggtaaa                        2499

SEQ ID NO: 2          moltype = AA  length = 833
FEATURE               Location/Qualifiers
source                1..833
                      mol_type = protein
                      organism = synthetic construct
SEQUENCE: 2
MKWVTFISLL FLFSSAYSIW ELKKDVYVVE LDWYPDAPGE MVVLTCDTPE EDGITWTLDQ   60
SSEVLGSGKT LTIQVKEFGD AGQYTCHKGG EVLSHSLLLL HKKEDGIWST DILKDQKEPK  120
NKTFLRCEAK NYSGRFTCWW LTTISTDLTF SVKSSRGSSD PQGVTCGAAT LSAERVRGDN  180
KEYEYSVECQ EDSACPAAEE SLPIEVMVDA VHKLKYENYT SSFFIRDIIK PDPPKNLQLK  240
PLKNSRQVEV SWEYPDTWST PHSYFSLTFC VQVQGKSKRE KKDRVFTDKT SATVICRKNA  300
SISVRAQDRY YSSSWSEWAS VPCSGGGSG  GGGSGGGGSR NLPVATPDPG MFPCLHHSQN  360
LLRAVSNMLQ KARQTLEFYP CTSEEIDHED ITKDKTSTVE ACLPLELTKN ESCLNSRETS  420
FITNGSCLAS RKTSFMMALC LSSIYEDLKM YQVEFKTMNA KLLMDPKRQI FLDQNMLAVI  480
DELMQALNFN SETVPQKSSL EEPDFYKTKI KLCILLHAFR IRAVTIDRVM SYLNASITCP  540
```

```
PPMSVEHADI WVKSYSLYSR ERYICNSGFK RKAGTSSLTE CVLNKATNVA HWTTPSLKCI  600
REPKSCDKTH TCPPCPAPEL LGGPSVFLFP PKPKDTLMIS RTPEVTCVVV DVSHEDPEVK  660
FNWYVDGVEV HNAKTKPREE QYNSTYRVVS VLTVLHQDWL NGKEYKCKVS NKALPAPIEK  720
TISKAKGQPR EPQVYTLPPS RDELTKNQVS LTCLVKGFYP SDIAVEWESN GQPENNYKTT  780
PPVLDSDGSF FLYSKLTVDK SRWQQGNVFS CSVMHEALHN HYTQKSLSLS PGK         833

SEQ ID NO: 3           moltype = DNA  length = 867
FEATURE                Location/Qualifiers
source                 1..867
                       mol_type = other DNA
                       organism = synthetic construct
SEQUENCE: 3
atgaagtggg tgaccttcat cagcctgctg ttcctgttct ccagcgccta ctcctacttc   60
ggcaagctgg agtccaagct gtccgtgatc aggaacctga cgaccaggt gctgttcatc   120
gaccagggca acaggcccct gttcgaggac atgaccgact ccgactgcag ggacaacgcc  180
cctaggacca tcttcatcat ctccatgtat aaggacagcc agcccagggg aatggccgtg  240
accatctccg tgaagtgcga gaagatctcc accctgtcct gcgagaacaa gatcatctcc  300
ttcaaggaga tgaaccccc cgacaacatc aaggacacca gtccgacat catcttcttc   360
cagcggtccg tgcccggaca cgacaacaag atgcagttcg agtcctcctc ctacgagggc  420
tactttctgg cctgtgagaa ggagagggac ctcttcaagc tcatcctgaa gaaggaggac  480
gagctgggcg acaggtccat catgttcacc gtgcagaacg aggacaactg ggttaacgta  540
ataagtgatt tgaaaaaaat tgaagatctt attcaatcta tacattga tgctacttta   600
tatacgaaa gtgatgttca ccccagttgc aaagtaacag caatgaagtg ctttctcttg   660
gagttacaag ttatttcact tgagtccgga gatgcaagta ttcatgatac agtagaaaat  720
ctgatcatcc tagcaaacga cagttttgtc tctaatggga atgtaacaga atctggatgc  780
aaagaatgtg aggaactga ggaaaaaaat attaaagaat tttgcagag ttttgtacat    840
attgtccaaa tgttcatcaa cacttct                                       867

SEQ ID NO: 4           moltype = AA   length = 289
FEATURE                Location/Qualifiers
source                 1..289
                       mol_type = protein
                       organism = synthetic construct
SEQUENCE: 4
MKWVTFISLL FLFSSAYSYF GKLESKLSVI RNLNDQVLFI DQGNRPLFED MTDSDCRDNA   60
PRTIFIISMY KDSQPRGMAV TISVKCEKIS TLSCENKIIS FKEMNPPDNI KDTKSDIIFF  120
QRSVPGHDNK MQFESSSYEG YFLACEKERD LFKLILKKED ELGDRSIMFT VQNEDNWVNV  180
ISDLKKIEDL IQSMHIDATL YTESDVHPSC KVTAMKCFLL ELQVISLESG DASIHDTVEN  240
LIILANDSLS SNGNVTESGC KECEELEEKN IKEFLQSFVH IVQMFINTS             289

SEQ ID NO: 5           moltype = DNA  length = 1416
FEATURE                Location/Qualifiers
source                 1..1416
                       mol_type = other DNA
                       organism = synthetic construct
SEQUENCE: 5
atgaagtggg tgaccttcat cagcctgctg ttcctgttct ccagcgccta ctcctacttc   60
ggcaagctgg agtccaagct gtccgtgatc aggaacctga cgaccaggt gctgttcatc   120
gaccagggca acaggcccct gttcgaggac atgaccgact ccgactgcag ggacaacgcc  180
cctaggacca tcttcatcat ctccatgtat aaggacagcc agcccagggg aatggccgtg  240
accatctccg tgaagtgcga gaagatctcc accctgtcct gcgagaacaa gatcatctcc  300
ttcaaggaga tgaaccccc cgacaacatc aaggacacca gtccgacat catcttcttc   360
cagcggtccg tgcccggaca cgacaacaag atgcagttcg agtcctcctc ctacgagggc  420
tactttctgg cctgtgagaa ggagagggac ctcttcaagc tcatcctgaa gaaggaggac  480
gagctgggcg acaggtccat catgttcacc gtgcagaacg aggacatcac gtgtcctcc   540
cctatgtccg tggaacacgc agacatctgg gtcaagagct acagcttgta ctccaggag   600
cggtacattt gtaactctgg tttcaagcgt aaagccggca cgtccagcct gacggagtgc  660
gtgttgaaca aggccacgaa tgtcgcccac tggacaaccc ccagtctcaa atgcattaga  720
gagccgaaat cttgtgacaa aactcacaca tgcccaccgt gcccagcacc tgaactcctg  780
gggggaccgt cagtcttcct cttcccccca aaaccaagg acaccctcat gatctcccgg   840
accccctgagg tcacatgcgt ggtggtggac gtgagccacg aagaccctga ggtcaagttc  900
aactggtacg tggacggcgt ggaggtgcat aatgccaaga caaagccgcg ggaggagcag  960
tacaacagca cgtaccgtgt ggtcagcgtc ctcaccgtcc tgcaccagga ctggctgaat 1020
ggcaaggagt acaagtgcaa ggtctccaac aaagccctcc cagccccat cgagaaaacc 1080
atctccaaag ccaaagggca gccccgagaa ccacaggtgt acaccctgcc ccatcccgg  1140
gatgagctga ccaagaacca ggtcagcctg acctgcctgg tcaaaggctt ctatcccagc 1200
gacatcgccg tggagtggga gagcaatggg cagccggaga caactacaa gaccacgcct  1260
cccgtgctgg actccgacgg ctccttcttc ctctacagca agctcaccgt ggacaagagc  1320
aggtggcagc aggggaacgt cttctcatgc tccgtgatgc atgaggctct gcacaaccac  1380
tacacgcaga agagcctctc cctgtctcct ggtaaa                            1416

SEQ ID NO: 6           moltype = AA   length = 472
FEATURE                Location/Qualifiers
source                 1..472
                       mol_type = protein
                       organism = synthetic construct
SEQUENCE: 6
MKWVTFISLL FLFSSAYSYF GKLESKLSVI RNLNDQVLFI DQGNRPLFED MTDSDCRDNA   60
PRTIFIISMY KDSQPRGMAV TISVKCEKIS TLSCENKIIS FKEMNPPDNI KDTKSDIIFF  120
```

| | | | | | |
|---|---|---|---|---|---|
| QRSVPGHDNK | MQFESSSYEG | YFLACEKERD | LFKLILKKED | ELGDRSIMFT | VQNEDITCPP | 180
| PMSVEHADIW | VKSYSLYSRE | RYICNSGFKR | KAGTSSLTEC | VLNKATNVAH | WTTPSLKCIR | 240
| EPKSCDKTHT | CPPCPAPELL | GGPSVFLFPP | KPKDTLMISR | TPEVTCVVVD | VSHEDPEVKF | 300
| NWYVDGVEVH | NAKTKPREEQ | YNSTYRVVSV | LTVLHQDWLN | GKEYKCKVSN | KALPAPIEKT | 360
| ISKAKGQPRE | PQVYTLPPSR | DELTKNQVSL | TCLVKGFYPS | DIAVEWESNG | QPENNYKTTP | 420
| PVLDSDGSFF | LYSKLTVDKS | RWQQGNVFSC | SVMHEALHNH | YTQKSLSLSP | GK | 472

```
SEQ ID NO: 7           moltype = DNA   length = 1950
FEATURE                Location/Qualifiers
source                 1..1950
                       mol_type = other DNA
                       organism = synthetic construct
SEQUENCE: 7
atgaagtggg tgaccttcat cagcctgctg ttcctgttct ccagcgccta ctccatctgg   60
gagctgaaga aagacgtgta tgtcgtggag ctggactggt atcctgacgc ccccggcgag  120
atggtggtgc tgacatgcga caccoctgag gaggatggca tcacatggac cctggaccaa  180
agcagcgagg tgctgggctc cggaaagacc ctgaccatcc aggtgaagga gttcggcgac  240
gccggcgagt ataccgcca taagggaggc gaggtgctga gccactccct gctcctgctg  300
cacaagaagg aagatggcat ctggagcacc gatattctga aggaccagaa ggagcccaag  360
aacaaaacct ttctgcggtg cgaggccaag aattattccg gcaggttcac ctgctggtgg  420
ctgaccacaa tctccaccga cctgaccttc agcgtcaaga gctccagggg atcctccgat  480
cctcagggcg tgacctgtgg agctgccacc ctgtccgctg agagggtgag gggcgacaac  540
aaggagtacg agtactccgt cgagtgtcag gaggactccg cctgccctgc tgccgaagag  600
agcctgccta tcgaagtcat ggtggacgcc gtgcacaagc tgaagtatga aactacacc  660
agcagctttt tcatccggga cattatcaag cctgatcccc ctaagaacct gcagctcaag  720
cccctgaaga attcccggca agtcgaggtg tcctgggaat accccgacac ctggtctaca  780
cctcactcct atttttagcct gaccttctgc gtgcaggtgc agggcaagag caagagggag  840
aagaaagacc gggtgttcac cgacaagacc agcgctaccg tgatctgtcg gaagaacgct  900
tccatttccg tgcgggctca ggacaggtat tactcctcct cctggtccga gtgggctagc  960
gtccccctgca gcgggaggtg cggatccgga ggtggaggtt ctggtggagg tgggagtagg 1020
aacctgcccg tggctacacc cgaccctgga atgttccctt gtctccacca cagccaaaac 1080
ctcctgcggg ccgtgtccaa catgctgcaa aaggctcggc agacactgga gttctacccc 1140
tgcaccagcg aggagatcga ccatgaggac atcacaaagg acaagacaag caccgtggag 1200
gcttgcctcc cctggaact gaccaagaat gagtcctgcc tcaacagccg ggagacatcc 1260
ttcatcacca atggctctg tctggcttcc cggaagacaa gcttcatgat ggccctgtgt 1320
ctgtccagca tctatgagga cctgaagatg taccaggtcg agtttaagac catgaacgcc 1380
aagctgctga tggaccccaa gcggcaaatc ttcctggacc agaacatgct ggctgtgatc 1440
gacgagctga tgcaggctct gaacttcaac agcgagaccg tgcccagaa gtcctccctg 1500
gaggagcctg attttttacaa gaccaaaatc aagctctgca tcctcctgca cgccttccgg 1560
atcagggccg tgaccatcga tcgggtgatg tcctacctga atgcttccaa ctgggttaac 1620
gtaataagtg atttgaaaaa aattgaagat cttattcaat ctatgcatat tgatgctact 1680
ttatatacgg aaagtgatgt tcaccccagt tgcaaagtaa cagcaatgaa gtgctttctc 1740
ttggagttac aagttatttc acttgagtcc ggagatgcaa gtattcatga tacagtagaa 1800
aatctgatca tcctagcaaa cgacagtttg tcttctaatg gaatgtaac agaatctgga 1860
tgcaaagaat gtgaggaact ggaggaaaaa aatattaaag aattttttgca gagttttgta 1920
catattgtcc aaatgttcat caacacttct                                   1950

SEQ ID NO: 8           moltype = AA   length = 650
FEATURE                Location/Qualifiers
source                 1..650
                       mol_type = protein
                       organism = synthetic construct
SEQUENCE: 8
```
| | | | | | |
|---|---|---|---|---|---|
| MKWVTFISLL | FLFSSAYSIW | ELKKDVYVVE | LDWYPDAPGE | MVVLTCDTPE | EDGITWTLDQ | 60
| SSEVLGSGKT | LTIQVKEFGD | AGQYTCHKGG | EVLSHSLLLL | HKKEDGIWST | DILKDQKEPK | 120
| NKTFLRCEAK | NYSGRFTCWW | LTTISTDLTF | SVKSSRGSSD | PQGVTCGAAT | LSAERVRGDN | 180
| KEYEYSVECQ | EDSACPAAEE | SLPIEVMVDA | VHKLKYENYT | SSFFIRDIIK | PDPPKNLQLK | 240
| PLKNSRQVEV | SWEYPDTWST | PHSYFSLTFC | VQVQGKSKRE | KKDRVFTDKT | SATVICRKNA | 300
| SISVRAQDRY | YSSSWSEWAS | VPCSGGGGSG | GGSGGGGSR | NLPVATPDPG | MFPCLHHSQN | 360
| LLRAVSNMLQ | KARQTLEFYP | CTSEEIDHED | ITKDKTSTVE | ACLPLELTKN | ESCLNSRETS | 420
| FITNGSCLAS | RKTSFMMALC | LSSIYEDLKM | YQVEFKTMNA | KLLMDPKRQI | FLDQNMLAVI | 480
| DELMQALNFN | SETVPQKSSL | EEPDFYKTKI | KLCILLHAFR | IRAVTIDRVM | SYLNASNWVN | 540
| VISDLKKIED | LIQSMHIDAT | LYTESDVHPS | CKVTAMKCFL | LELQVISLES | GDASIHDTVE | 600
| NLIILANDSL | SSNGNVTESG | CKECEELEEK | NIKEFLQSFV | HIVQMFINTS | | 650

```
SEQ ID NO: 9           moltype = AA   length = 450
FEATURE                Location/Qualifiers
source                 1..450
                       mol_type = protein
                       organism = synthetic construct
SEQUENCE: 9
```
| | | | | | |
|---|---|---|---|---|---|
| METDTLLLWV | LLLWVPGSTG | NWVNVISDLK | KIEDLIQSMH | IDATLYTESD | VHPSCKVTAM | 60
| KCFLLELQVI | SLESGDASIH | DTVENLIILA | NDSLSSNGNV | TESGCKECEE | LEEKNIKEFL | 120
| QSFVHIVQMF | INTSMDRLTS | SFLLLIVPAY | VLSITCPPPM | SVEHADIVWK | SYSLYSRERY | 180
| ICNSGFKRKA | GTSSLTECVL | NKATNVAHWT | TPSLKCIREP | KSCDKTHTCP | PCPAPELLGG | 240
| PSVFLFPPKP | KDTLMISRTP | EVTCVVVDVS | HEDPEVKFNW | YVDGVEVHNA | KTKPREEQYN | 300
| STYRVVSVLT | VLHQDWLNGK | EYKCKVSNKA | LPAPIEKTIS | KAKGQPREPQ | VYTLPPSRDE | 360

```
LTKNQVSLTC LVKGFYPSDI AVEWESNGQP ENNYKTTPPV LDSDGSFFLY SKLTVDKSRW   420
QQGNVFSCSV MHEALHNHYT QKSLSLSPGK                                   450

SEQ ID NO: 10           moltype = AA   length = 6
FEATURE                 Location/Qualifiers
source                  1..6
                        mol_type = protein
                        organism = synthetic construct
SEQUENCE: 10
PELLGG                                                               6

SEQ ID NO: 11           moltype = AA   length = 6
FEATURE                 Location/Qualifiers
source                  1..6
                        mol_type = protein
                        organism = synthetic construct
SEQUENCE: 11
PEAAGG                                                               6

SEQ ID NO: 12           moltype = AA   length = 5
FEATURE                 Location/Qualifiers
source                  1..5
                        mol_type = protein
                        organism = synthetic construct
SEQUENCE: 12
KCKSL                                                                5

SEQ ID NO: 13           moltype = AA   length = 5
FEATURE                 Location/Qualifiers
source                  1..5
                        mol_type = protein
                        organism = synthetic construct
SEQUENCE: 13
KCASL                                                                5
```

What is claimed is:

1. A method of activating Natural Killer (NK) cells, the method comprising exposing NK coils to an isolated soluble fusion protein complex comprising a first soluble protein comprising an interleukin-15 (IL-15) polypeptide domain and an IL-18 polypeptide domain, and a second soluble protein comprising a soluble IL-15 receptor alpha sushi (IL-15RαSu) polypeptide domain and an IL-12 polypeptide domain, wherein the IL-15 polypeptide domain binds to the IL-15RαSu polypeptide domain to form the soluble fusion protein complex, wherein the NK cells are activated.

2. The method of claim 1, wherein the activated NK cells have increased expression of one or more activation markers, wherein the activation markers comprise CD25 and/or CD69.

3. The method of claim 1, wherein the activated NK cells have increased cytotoxicity against cancerous or virally infected cells.

4. The method of claim 3, wherein the activated NK cells have increased production of Interferon gamma (IFNγ).

5. The method of claim 1, wherein the NK cells are primary NK cells.

6. The method of claim 5, wherein the activated NK cells are comprised of Cytokine Induced Memory Like (CIML) NK cells.

7. The method of claim 1, wherein the NK cells comprise an NK cell line.

* * * * *

UNITED STATES PATENT AND TRADEMARK OFFICE
CERTIFICATE OF CORRECTION

PATENT NO. : 11,872,272 B2
APPLICATION NO. : 18/168428
DATED : January 16, 2024
INVENTOR(S) : Warren D. Marcus et al.

Page 1 of 1

It is certified that error appears in the above-identified patent and that said Letters Patent is hereby corrected as shown below:

In the Claims

In Claim 1, Column 69, Line 34 please delete "method comprising exposing NK coils to an isolated soluble" and insert -- method comprising exposing NK cells to an isolated soluble --

Signed and Sealed this
Twenty-sixth Day of November, 2024

Katherine Kelly Vidal
*Director of the United States Patent and Trademark Office*